US012751672B2

(12) United States Patent
Kovatchev et al.

(10) Patent No.: US 12,751,672 B2
(45) Date of Patent: Oct. 6, 2026

(54) METHOD FOR STRUCTURING AND CLASSIFICATION OF CONTINUOUS GLUCOSE MONITORING (CGM) PROFILES

(71) Applicant: UNIVERSITY OF VIRGINIA PATENT FOUNDATION, Charlottesville, VA (US)

(72) Inventors: Boris P. Kovatchev, Charlottesville, VA (US); Benjamin Lobo, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 950 days.

(21) Appl. No.: 17/829,754

(22) Filed: Jun. 1, 2022

(65) Prior Publication Data

US 2022/0386965 A1 Dec. 8, 2022

Related U.S. Application Data

(60) Provisional application No. 63/196,951, filed on Jun. 4, 2021.

(51) Int. Cl.
*A61B 5/00* (2006.01)
*A61B 5/145* (2006.01)
(Continued)

(52) U.S. Cl.
CPC ........ *A61B 5/7264* (2013.01); *A61B 5/14532* (2013.01); *A61B 5/7246* (2013.01);
(Continued)

(58) Field of Classification Search
CPC ............ A61B 2505/07; A61B 5/14532; A61B 5/7246; A61B 5/7253; A61B 5/7264;
(Continued)

(56) References Cited

U.S. PATENT DOCUMENTS

| | | | | |
|---|---|---|---|---|
| 2013/0297224 A1* | 11/2013 | Staib | ...................... | G09B 23/28 702/21 |
| 2017/0251980 A1* | 9/2017 | Duke | ...................... | G06F 17/16 |

(Continued)

FOREIGN PATENT DOCUMENTS

| | | |
|---|---|---|
| CN | 109791807 A | 5/2019 |
| CN | 109964281 A | 7/2019 |

(Continued)

OTHER PUBLICATIONS

International Search Report and Written Opinion of the International Searching Authority (Forms PCT/ISA/220, PCT/ISA/210 and PCT/ISA/237) issued on Sep. 28, 2022, by the European Patent Office in corresponding International Application No. PCT/US2022/032121. (13 pages).

(Continued)

*Primary Examiner* — Devin B Henson
*Assistant Examiner* — Kavya Shobana Balaji
(74) *Attorney, Agent, or Firm* — Buchanan Ingersoll & Rooney P.C.

(57) ABSTRACT

Embodiment relate to a system for developing a model to classify continuous glucose monitoring (CGM) data. The system includes a processor and computer memory having instructions stored thereon that when executed will cause the processor to determine whether two CGM profiles match based on a similarity of shapes of the two CGM profiles, each CGM profile including a data set of CGM measurements. The processor designates two matching CGM profiles as a CGM profile pair. The processor transforms the CGM profile pair into a motif. The processor labels the motif as a labelled motif based on a clinical characteristic. The processor recursively repeats the determine, designate and transform steps of a CGM profile pairing process until a finite set of motifs is created, which includes the labelled
(Continued)

motif as a classified data point. The processor monitor, analyzes, or influences a concentration of glucose levels in a fluid.

20 Claims, 50 Drawing Sheets

(51) Int. Cl.
*G16H 10/40* (2018.01)
*G16H 50/70* (2018.01)

(52) U.S. Cl.
CPC .......... *A61B 5/7253* (2013.01); *A61B 5/7275* (2013.01); *G16H 10/40* (2018.01); *G16H 50/70* (2018.01)

(58) Field of Classification Search
CPC ... A61B 5/7275; A61B 10/00; A61B 2562/00; A61B 2505/00; G16H 10/40; G16H 10/60; G16H 20/17; G16H 50/20; G16H 50/70; G16H 80/00; G16H 10/00; G16H 15/00; G16H 20/00; G16H 30/00; G16H 40/00; G16H 70/00; G16H 50/00
See application file for complete search history.

(56) References Cited

U.S. PATENT DOCUMENTS

2017/0348484 A1 12/2017 Duke et al.
2019/0274603 A1 9/2019 Ringemann
2019/0369108 A1 12/2019 Breschi et al.
2021/0361199 A1* 11/2021 Kumar .................. G16H 40/67
2022/0061710 A1* 3/2022 Hadley .................. G16H 10/40

FOREIGN PATENT DOCUMENTS

JP 2001212114 A 8/2001
WO 2020257667 A1 12/2020
WO 2021097178 A1 5/2021

OTHER PUBLICATIONS

Office Action (Communication) issued on Jan. 16, 2024, by the European Patent Office in corresponding European Patent Application No. 22740609.7. (3 pages).
International Search Report and Written Opinion of the International Searching Authority (Forms PCT/IB/373 and PCT/ISA/237) issued on Nov. 21, 2023, by the International Bureau of WIPO in corresponding International Application No. PCT/US2022/032121. (8 pages).
Office Action (Notice of Reasons for Refusal) issued on Apr. 30, 2026, by the Japanese Patent Office in corresponding Japanese Patent Application No. 2023-574782, and an English Translation of the Office Action. (6 pages).
First Office Action issued on Apr. 29, 2026, by the Chinese Patent Office in corresponding Chinese Patent Application No. 202280036195.8, and an English Translation of the Office Action. (10 pages).

* cited by examiner

METHOD FOR STRUCTURING AND CLASSIFICATION OF CONTINUOUS GLUCOSE MONITORING (CGM) PROFILES

CROSS-REFERENCE TO RELATED APPLICATIONS

This patent application is related to and claims the benefit of priority to U.S. Provisional Patent Application No. 63/196,951, filed on Jun. 4, 2021, the entire contents being incorporated herein by reference.

FIELD

Embodiments relate to systems and methods for developing and implementing a model to classify continuous glucose monitoring (CGM) data.

BACKGROUND INFORMATION

About 422 million people worldwide have type 1 diabetes (T1D) or type 2 diabetes (T2D), with the latter accounting for 90-95% of cases [World Health Organization, 2020]. In diabetes, the hormonal network which controls glucose metabolism and ensures a stable fasting blood glucose suffers from the absence of insulin secretion (T1D) or inadequate insulin secretion (T2D) [Kovatchev, 2019]. Safe and effective treatment of patients with diabetes requires frequent and accurate monitoring of their blood sugar levels. The introduction of continuous glucose monitoring (CGM) devices more than two decades ago has been gradually associated with a significant paradigm shift in the way people with diabetes, and especially people with T1D, treat their disease. The advantage of these systems comes from their ability to accurately measure the concentration of blood glucose more frequently than it is possible to by other traditional methods (e.g., by fingerstick devices), and this enables visualization of a more complete glucose profile and its associated dynamics. This information can be used by patients or their physicians in real time; this information can also be used by computer-based decision support or closed-loop systems to markedly improve the safety and efficacy of diabetes therapy [Bergenstal, 2018, Nimri et al., 2019]. The CGM-based Ambulatory Glucose Profile (AGP) report incorporated in several CGM devices includes glycemic metrics and allows for visualization of the glucose frequency distributions based on multiple daily CGM profiles. The AGP report can be considered the current "standard-of-care" personalized CGM-based management tool [Bergenstal, 2018]. The advent of CGM devices also led to several new research directions including studies in: (i) novel data-driven methods for prediction of blood glucose dynamics [Woldaregay et al., 2019b], (ii) advanced classification of different therapeutic strategies and patient populations [Kahkoska et al., 2019, Augstein et al., 2015], (iii) CGM pattern classification [Woldaregay et al., 2019a, Shah et al., 2019], and (iv) several machine-learning applications in T1D [Woldaregay et al., 2019a].

In the U.S., CGM use among T1D patients has increased from 6% in 2011 to 38% in 2018 [Foster et al., 2019] and continues to increase worldwide in both T1D and T2D. A typical CGM sensor collects a single data point every five minutes, and so a CGM time series from a single day (i.e., a daily CGM profile) contains 288 data points. A year of daily CGM data from just one individual contains over one hundred thousand data points. The CGM data however, is not fully utilized in common clinical practice and in the day-to-day treatment of diabetes. This is due in part to the limited availability of quantitative methods for analysis of the data generated by these devices. For example, CGM data is presented to the patient or to their physician as a plot of the immediate CGM history, or as multiple daily profiles plotted simultaneously and accompanied by aggregated glycemia risk metrics [Kovatchev, 2017]. The commercially available closed-loop artificial pancreas (AP) systems from Medtronic and Tandem Diabetes Care use CGM data in a more sophisticated way, but even these technologically advanced clinical applications do not take full advantage of the specificity and "richness" of the wealth of information present in the CGM data.

SUMMARY

Embodiments relate to a system for developing a model to classify continuous glucose monitoring (CGM) data. The system includes a processor and computer memory having instructions stored thereon that when executed will cause the processor to determine whether the two CGM profiles match based on a similarity of shapes of the two CGM profiles, each CGM profile including a data set of CGM measurements. The processor designates two matching CGM profiles as a CGM profile pair. The processor transforms the CGM profile pair into a motif. The processor labels the motif as a labelled motif based on a clinical characteristic. The processor recursively repeats the determine, designate and transform steps of a CGM profile pairing process until a finite set of motifs is created, which includes the labelled motif as a classified data point. The processor monitors, analyzes, or influences a concentration of glucose levels in a fluid using the labelled motif and classified data point.

Embodiments relate to a method for developing a model to classify continuous glucose monitoring (CGM) data. The method involves determining whether the two CGM profiles match based on a similarity of shapes of the two CGM profiles, each CGM profile including a data set of CGM measurements. The method involves designating two matching CGM profiles as a CGM profile pair. The method involves transforming the CGM profile pair into a motif. The method involves labeling the motif as a labelled motif based on a clinical characteristic. The method involves recursively repeating the determining, designating and transforming steps of a CGM profile pairing process until a finite set of motifs is created, which includes the labelled motif as a classified data point. The method involves monitoring, analyzing, or influencing a concentration of glucose levels in a fluid using the labelled motif and the classified data point.

Embodiments relate to a system for classifying patient continuous glucose monitoring (CGM) data. The system includes a processor, and associated memory having instructions stored thereon that when executed will cause the processor to obtain patient CGM profile including a data set of patient CGM measurements. The processor compares the patient CGM profile to a finite set of motifs, the finite set of motifs including CGM profile pairs that have been transformed into labelled motifs. The processor classifies the patient CGM profile into one or more clinical characteristics based on a match between the patient CGM profile and a CGM profile pair of a labelled motif. The processor monitors, analyzes, or influences a concentration of glucose levels in a fluid based on the classification of the patient CGM profile.

BRIEF DESCRIPTION OF THE DRAWINGS

Other features and advantages of the present disclosure will become more apparent upon reading the following detailed description in conjunction with the accompanying drawings, wherein like elements are designated by like numerals, and wherein.

DETAILED DESCRIPTION

Figure 1A:
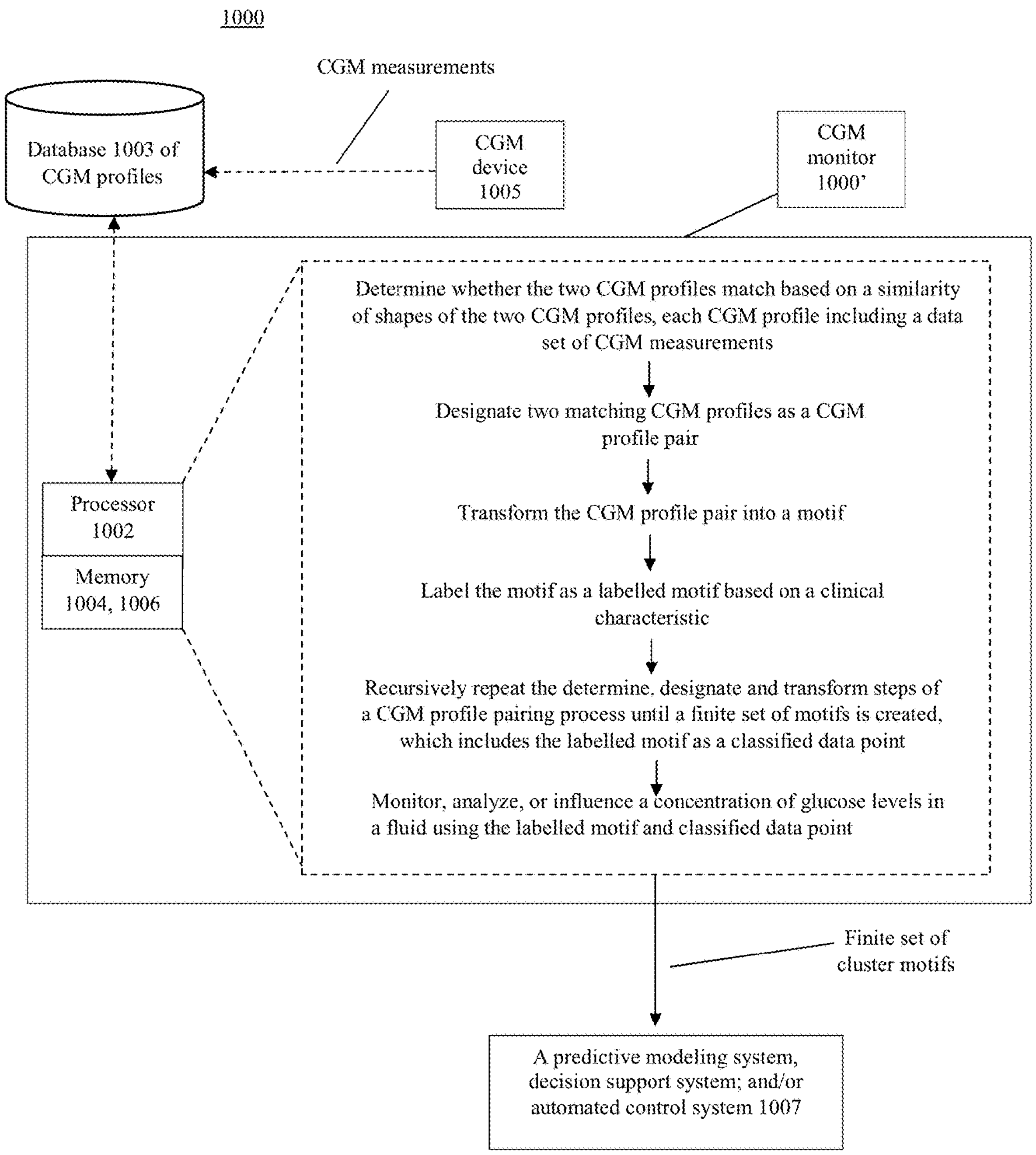
FIG. 1A shows an exemplary system diagram for developing a model to classify continuous glucose monitoring (CGM) data.

Referring to FIG. 1A, embodiments can relate to a system 1000 for developing a model to classify continuous glucose monitoring (CGM) data. The system 1000 can include a processor 1002. The system 1000 can include memory 1004, 1006, which can include computer memory. The memory 1004, 1006 can be associated with the processor 1002. The memory 1004, 1006 can have instructions 1024 stored thereon that when executed will cause the processor 1002 to execute algorithmic steps for developing a model to classify CGM data.

The processor 1002 can be any of the processors 1002 disclosed herein. The processor 1002 can be part of or in communication with a machine 1000' (logic, one or more components, circuits (e.g., modules), or mechanisms). The processor 1002 can be hardware (e.g., processor, integrated circuit, central processing unit, microprocessor, core processor, computer device, etc.), firmware, software, etc. configured to perform operations by execution of instructions embodied in algorithms, data processing program logic, artificial intelligence programming, automated reasoning programming, etc. It should be noted that use of processors 1002 herein can include any one or combination of a Graphics Processing Unit (GPU), a Field Programmable Gate Array (FPGA), a Central Processing Unit (CPU), etc. The processor 1002 can include one or more processing modules. A processing module can be a software or firmware operating module configured to implement any of the method steps disclosed herein. The processing module can be embodied as software and stored in memory, the memory being operatively associated with the processor 1002. A processing module can be embodied as a web application, a desktop application, a console application, etc. Exemplary embodiments of the processor 1002 and the machine 1000' are discussed later.

The processor 1002 can include or be associated with a computer or machine readable medium 1022. As discussed in more detail later, the computer or machine readable medium 1022 can include memory. Any of the memory discussed herein can be computer readable memory configured to store data. The memory can include a volatile or non-volatile, transitory or non-transitory memory, and be embodied as an in-memory, an active memory, a cloud memory, etc. Embodiments of the memory can include a processor module and other circuitry to allow for the transfer of data to and from the memory, which can include to and from other components of a communication system. This transfer can be via hardwire or wireless transmission. The communication system can include transceivers, which can be used in combination with switches, receivers, transmitters, routers, gateways, wave-guides, etc. to facilitate communications via a communication approach or protocol for controlled and coordinated signal transmission and processing to any other component or combination of components of the communication system. The transmission can be via a communication link. The communication link can be electronic-based, optical-based, opto-electronic-based, quantum-based, etc.

The computer or machine readable medium 1022 can be configured to store one or more instructions 1024 thereon. The instructions 1024 can be in the form of algorithms, program logic, etc. that cause the processor 1002 to build and implement embodiment of the model.

The processor 1002 can be in communication with other processors of other devices 1007 (e.g., a glycemic state monitoring device, a glucose management system, an insulin recommendation system, an insulin delivery device, etc.). Any of those other devices 1007 can include any of the exemplary processors disclosed herein. Any of the processors can have transceivers or other communication devices/ circuitry to facilitate transmission and reception of wireless signals. Any of the processors can include an Application Programming Interface (API) as a software intermediary that allows two applications to talk to each other. Use of an API can allow software of the processor 1002 of the system 1000 to communicate with software of the processor of the other device(s) 1007, if the processor 1002 of the system 1000 is not the same processor of the device 1007.

The instructions 1024 can cause the processor 1002 to determine whether the two CGM profiles match based on a similarity of shapes of the two CGM profiles. Each CGM profile includes a data set of CGM measurements. It is contemplated for each CGM profile to include a data set of CGM measurements from a patient and for a period of time. It is contemplated for the period of time to be 24 hours, but other periods of time can be used (e.g., 1 hour, 6 hours, 48 hours, 168 hours, etc.). The CGM data can be sampled data at a predetermined sample rate (e.g., every 1 second, every 5 seconds, every 60 seconds, etc.). The compilation of CGM data samples over the period of time is the CGM profile. It is contemplated for the period of time and sample rate for one CGM profile to be the same as for the period of time and sample rate for another CGM profile, but it need not be. The processor 1002 can obtain the CGM data and/or the CGM profiles from a database 1003. For instance, the processor 1002 can obtain CGM data from a database 1003 and create CGM profiles or obtain CGM profiles from a database 1003 that had already been created. The CGM data and/or CGM profiles obtained by the processor 1002 can be stored in memory 1004, 1006 for later processing. Obtaining the CGM data and/or CGM profiles can be via a pull operation (e.g., the processor 1002 can pull the data from the database 1003) or a push operation (e.g., the data can be pushed from the database 1003 to the processor 1002).

The instructions 1024 can cause the processor 1002 to designate two matching CGM profiles as a CGM profile pair. Matching can be determined by a degree of similarity between the two CGM profiles. The degree of similarity can be set by a threshold. For instance, a quantitative measure can be used to determine similarity of two CGM profiles and a threshold can be set to determine whether two CGM profiles are similar enough to be designated as a pair. An exemplary quantitative measure can be measuring a distance (e.g., Euclidean distance, root mean square error, etc.) between two CGM profiles. Other examples can include or statistical distances, such as Fisher Information Distance, Kullback-Leibler divergence, Kolmogorov-Smirnov distance between the data distributions of the two profiles, etc. Thresholds of determining similarity can be set to determine how close the shapes of each CGM profile are and/or how close in location each CGM profile is relative to each other. Each CGM profile pair can be saved in memory 1004, 1006 for later processing.

The instructions 1024 can cause the processor 1002 to transform the CGM profile pair into a motif. The transformation can involve a mathematical operation that generates a value to represent the CGM profile pair. An exemplary transformation can be averaging the two CGM profiles of the CGM profile pair. The averaging can involve using direct mean calculation, risk-weighted average placing more emphasis on hypo- or hyperglycemia, principal component approach, mean squares, etc. Each motif can be save in memory 1004, 1006 for later processing. Each CGM profile includes plural CGM data points. For instance, if CGM data is sampled every 5 minutes, a CGM profile can include 288 data points. Transforming a CGM profile pair to a motif allows the system 1000 to build a model based on a single motif data point representing the 288 data points of the CGM profile (or the 576 data points of the CGM profile pair). As will be explained in detail later, the model can then be used for classifying patient CGM data by comparing patient CGM data to a motif as opposed to comparing patient CGM data to 288 data points of a CGM profile. For instance, after the model is built with the motifs, new patient CGM data can be compared to a set of motifs of the model, the comparison being used to classify the patient CGM data. Comparing the new patient CGM data to a set of motifs as opposed to a set of stored CGM profiles reduces computational resources, improves accuracy, and adds functionality to the system 1000.

The instructions 1024 can cause the processor 1002 to label the motif as a labelled motif based on a clinical characteristic. For instance, each motif can be indexed. This indexing can involve indexing the motifs in an order in which the motifs are created or identified; however, it is understood that other indexing schemes can be used. It is also understood that the motifs can be re-indexed after being indexed. The index allows the motif to be identified and labelled. Because each motif is a time series of CGM values, it is possible to calculate clinical characteristics (e.g., standard glycemic metrics) which are associated with the motif. The motif can then be labelled in accordance with the clinical characteristic. As a non-limiting example, a time in range measure in which a predetermined number of blood glucose values of a CGM profile is within a predetermined range can be calculated, which can then be used as a clinical characteristic. The value of this clinical characteristic metric can be used to define the clinical characteristic of the motif and be stored in memory 1004, 1006. This can be used to label the motif based on the clinical characteristic associated with it.

The instructions 1024 can cause the processor 1002 to recursively repeat the determine, designate and transform steps of a CGM profile pairing process until a finite set of motifs is created, which includes the labelled motif as a classified data point.

The instructions 1024 can cause the processor 1002 to monitor, analyze, or influence a concentration of glucose levels in a fluid using the labelled motif and classified data point.

It is contemplated for the model to generate plural motifs from plural CGM profiles so as to generate a set of motifs for the model. The CGM profiles, at the model building stage, can be obtained from a database 1003. For instance, the CGM profiles can be previously generated CGM profiles that are stored in the database 1003. The CGM profiles can comprise CGM data/measurements obtained from one or more CGM devices 1005. The CGM profiles can be CGM data collected via the CGM device(s) 1005 from a single patient, multiple patients, patients with type 1 diabetes, patients with type 2 diabetes, etc. In this regard, the instructions 1024 can cause the processor 1002 to designate plural CGM profile pairs by comparing plural CGM profiles. Each matching CGM profile can be designated as a CGM profile pair.

The instructions 1024 can cause the processor 1002 to transform the plural CGM profile pairs into one or more motifs. This can involve transforming each CGM profile pair into a separate motif, any one or combination of CGM profile pairs into a single motif, any one or combination of CGM profile pairs into multiple motifs, etc.

The instructions 1024 can cause the processor 1002 to label the one or more motifs with one or more labels. This can involve labeling the one or more motifs based on a clinical characteristic. This can involve labelling each motif with a separate label, labeling any one or combination of motifs with a single label, labelling any one or combination of CGM profile pairs with multiple labels, etc.

The instructions 1024 can cause the processor 1002 to create the finite set of motifs which includes each individually labelled motif as a data point.

As noted above, the data point that is the labelled motif can be used for monitoring, analyzing, or influencing a concentration of glucose levels in fluid. This fluid can be blood, interstitial fluid, etc. For instance, the model can be used for classifying CGM data that is obtained from blood samples of a patient. The CGM data of the blood samples can be compared to one or more motifs of the set of motifs.

The instructions 1024 can cause the processor 1002 to obtain any one or combination of CGM profiles from a database 1003 of CGM profiles. Any one or combination of the CGM data/measurements generating the CGM profiles can be obtained from a CGM device 1005. Any one or combination of the CGM profiles can be a daily CGM profile of CGM data/measurements pertaining to a 24 hours period. For instance, the CGM profile can comprise CGM data/measurements from a patient for a period of time that is 24 hours. As noted above, other time periods can be used. The database 1003 of CGM profiles can include more than one CGM profile for a patient, which can include multiple time periods of CGM data. For instance, a patient can have a CGM profile-1 for day 1, a CGM profile-2 for day 2, etc. It is contemplated for the time period for CGM profile-1 to be the same as the time period for CGM profile-2, but it need not be. As noted above, the CGM data can be measurements taken as a predetermined sample rate. It is contemplated for the sample rate for CGM profile-1 to be the same as the time period for CGM profile-2, but it need not be. The database 1003 of CGM profiles can include one or more CGM profiles from any number of patients. The patients can be human or any other animal.

The instructions 1024 can cause the processor 1002 to perform linear interpolation, cubic splines, backward propagation, and/or forward propagation when a CGM profile includes a number of CGM measurements that is less than a predetermined number. For instance, a predetermined number of CGM data points for a CGM profile can be set. If that CGM profile comprises a number of CGM data points that is less than the predetermined number, estimation methods can be used to estimate one or more CGM data points so as to generate a CGM profile having the predetermined number of CGM data points. The estimation method can include linear interpolation, cubic splines, backward propagation, forward propagation, moving average, autoregression, etc. The predetermined number can be set based on optimization (e.g., weighing factors such as accuracy, reduction of computational resources, etc.). It is contemplated for each CGM profile to include CGM data that has been taken over the same period of time and at the same sample rate. For instance, for a daily CGM profile, each CGM profile can include 288 data points (e.g., CGM measurement taken every 5 minutes for 24 hours=288 data points). It is understood that some CGM profiles may have less than 288 data points due to a sensor reading error for example. For these CGM profiles, estimation methods can be used to generate a proxy CGM profile. That proxy CGM profile can be generated by the processor 1002 and: a) can be used by the processor 1002 instead of the CGM profile having the missing data point; b) can be sent back to the database 1003 to replace the CGM profile having the missing data point; c) stored in memory 1004, 1006 for later processing, etc. In the alternative, another processor can be used to process the CGM profiles in the database 1003 to perform such operations and generate the proxy CGM profiles so that the CGM profiles transmitted to the processor 1002 can receive CGM profiles that either have the requisite number of data points or have proxy CGM profiles that have estimated data points.

As noted above, the instructions 1024 can cause the processor 1002 to determine whether the two CGM profiles match by calculating a distance between two CGM profiles. This can involve determine whether the two CGM profiles match by calculating a distance in risk space between two the CGM profiles. For instance, the Euclidean distance can be defined over a glucose risk-space, which can make the metric specific to diabetes. Equations (1) and (7) (discussed later in the application) provides an example for defining Euclidean distance in risk-space.

The instructions 1024 can cause the processor 1002 to calculate the distance in risk space between two CGM profiles by calculating a root mean squared (RMSE) between two CGM profiles. Specific examples of calculating distance in risk space using RMSE are discussed later.

Any one or combination of motifs can be labelled in accordance with any one or combination of clinical characteristics associated with that motif. The clinical characteristic for a motif can include at least one or more of: 1) a time in range measure in which a predetermined number of blood glucose values of a CGM profile (a CGM profile of the two CGM profile pair forming the motif) is within a predetermined range; 2) a time above range measure in which a predetermined number of blood glucose values of a CGM profile (a CGM profile of the two CGM profile pair forming the motif) is greater than a predetermined value; 3) a time below range measure in which a predetermined number of blood glucose values of a CGM profile (a CGM profile of the two CGM profile pair forming the motif) is less than a predetermined value; 3) a coefficient of variability measure of blood glucose values of a CGM profile (a CGM profile of the two CGM profile pair forming the motif); and/or 4) a standard deviation measure of blood glucose values of a CGM profile (a CGM profile of the two CGM profile pair forming the motif). It is understood that other clinical characteristics can be used. Examples of other clinical characteristics can be appreciated from "*Metrics for glycaemic control—from HbA*1*c to continuous glucose monitoring*", Kovatchev, et al. Nature Reviews Endrocrinology, 2017, the entire contents of which is incorporated herein by reference.

The processor 1002 can be configured to be a component of, used in combination with, or in communication with another device/system 1007—e.g., his can include the processor 1002 being part of the device/system 1007, the device/system 1007 being part of the processor 1002, the processor 1002 in communication with the device/system 1007, etc. "Being part of" can include being on a same substrate or integrated circuit. For instance, the processor 1002 can be a component of, used in combination with, or in communication with a predictive modeling system (e.g., a system for predicting risk of hypo- or hyper-glycemia), a decision support system (e.g., a system for assisting with medical triage), and/or an automated control system (e.g., an artificial pancreas). The processor 1002 can use the model or provide the model to the device/system 1007 to assist with or augment the performance of these devices/systems 1007. For instance, the model can be used for classifying CGM data that is obtained from a patient. The CGM data from the patient can be classified based on a comparison of the data to the set of motifs so as to identify clinical characteristics associated with the CGM patient data. This can provide a quick and accurate assessment of the patient CGM patient data to determine whether it has a clinical characteristic associated with time in range, time above range, time below range, etc. The patient CGM data can be classified based on this assessment, wherein the classification can be used by the device/system 1007. The classification of the patient CGM data can be used by the device/system 1007 to assist with or augment predicting or reacting to aspects of glycemic states, or assist with or augment determining or modifying insulin administration therapies.

As an example, the device/system 1007 can be a glycemic state monitoring device, a glucose management system, an insulin recommendation system, etc. The device/system 1007 can be embodied as a computer device, a laptop, a cellphone, a smartphone, etc. As a non-limiting example, the processor 1002, or the device/system 1007 if the device/system 1007 is using the model for classification, can be configured to generate a signal to inform the device/system 1007 about hypo- or hyper-glycemia risk based on the classification of patient CGM data. For instance, the processor 1102, or the device/system 1007 if the device/system 1007 is using the model for classification, can generate a signal that includes a notification communication recommending, based on the classification of patient CGM data, at least one or more of: risk of hypo- or hyper-glycemia, change in risk of hypo- or hyper-glycemia, check patient glucose level, modification of insulin dosage, modification of basal insulin, modification of basal insulin rate, modification of insulin infusion rate, and/or modification of patient nutritional administration. The type of signal, frequency (how often it is generated), the number of signals, etc. can depend on set thresholds and the risk of hypo- or hyper-glycemia, change in risk of hypo- or hyper-glycemia, etc. The notification signal can be an email, short message service (SMS), a textual or graphical display, pager, etc.

In addition, or in the alternative, the system 1000 can be the processor 1002 in combination with a device/system 1007 that is an insulin delivery device. As a non-limiting example, the processor 1002, or the device/system 1007 if the device/system 1007 is using the model for classification, can be configured to generate a signal to inform the insulin delivery device about hypo- or hyper-glycemia risk based on the classification of patient CGM data. For instance, the processor 1002, or the device/system 1007 if the device/system 1007 is using the model for classification, can generate a signal that includes a command signal requiring, based on the classification of patient CGM data, at least one or more of: risk of hypo- or hyper-glycemia, change in risk of hypo- or hyper-glycemia, check patient glucose level, modification of insulin dosage, modification of basal insulin, modification of basal insulin rate, modification of insulin infusion rate, and/or modification of patient nutritional administration. The type of signal, frequency (how often it is generated), the number of signals, etc. can depend on set thresholds and the risk of hypo- or hyper-glycemia, change in risk of hypo- or hyper-glycemia, etc.

Embodiments can relate to a method for developing a model to classify CGM data. The method can involve determining whether the two CGM profiles match based on a similarity of shapes of the two CGM profiles, each CGM profile including a data set of CGM measurements. The method can involve designating two matching CGM profiles as a CGM profile pair. The method can involve transforming the CGM profile pair into a motif. The method can involve labeling the motif as a labelled motif based on a clinical characteristic. The method can involve recursively repeating the determining, designating and transforming steps of a CGM profile pairing process until a finite set of motifs is created, which includes the labelled motif as a classified data point. The method can involve monitoring, analyzing, or influencing a concentration of glucose levels in a fluid using the labelled motif and classified data point.

The method can involve designating plural CGM profile pairs, transforming the plural CGM profile pairs to form one or more motifs, labelling the one or more motifs with one or more labels, and creating the finite set of motifs which includes each individual labelled motif as a data point.

The method can involve monitoring, analyzing, or influencing a concentration of glucose levels in blood based on the data point.

Determining whether the two CGM profiles match can involve calculating a distance in risk space between two CGM profiles.

The clinical characteristic can include at least one or more of: 1) a time in range measure in which a predetermined number of blood glucose values of a CGM profile is within a predetermined range; 2) a time above range measure in which a predetermined number of blood glucose values of a CGM profile is greater than a predetermined value; 3) a time below range measure in which a predetermined number of blood glucose values of a CGM profile is less than a predetermined value; 4) a coefficient of variability measure of blood glucose values of a CGM profile; and/or 4) a standard deviation measure of blood glucose values of a CGM profile. It is understood that other clinical characteristics can be used. Examples of other clinical characteristics can be appreciated from "*Metrics for glycaemic control—from HbA1c to continuous glucose monitoring*", Kovatchev, et al. Nature Reviews Endrocrinology, 2017, the entire contents of which is incorporated herein by reference.

Figure 1B:
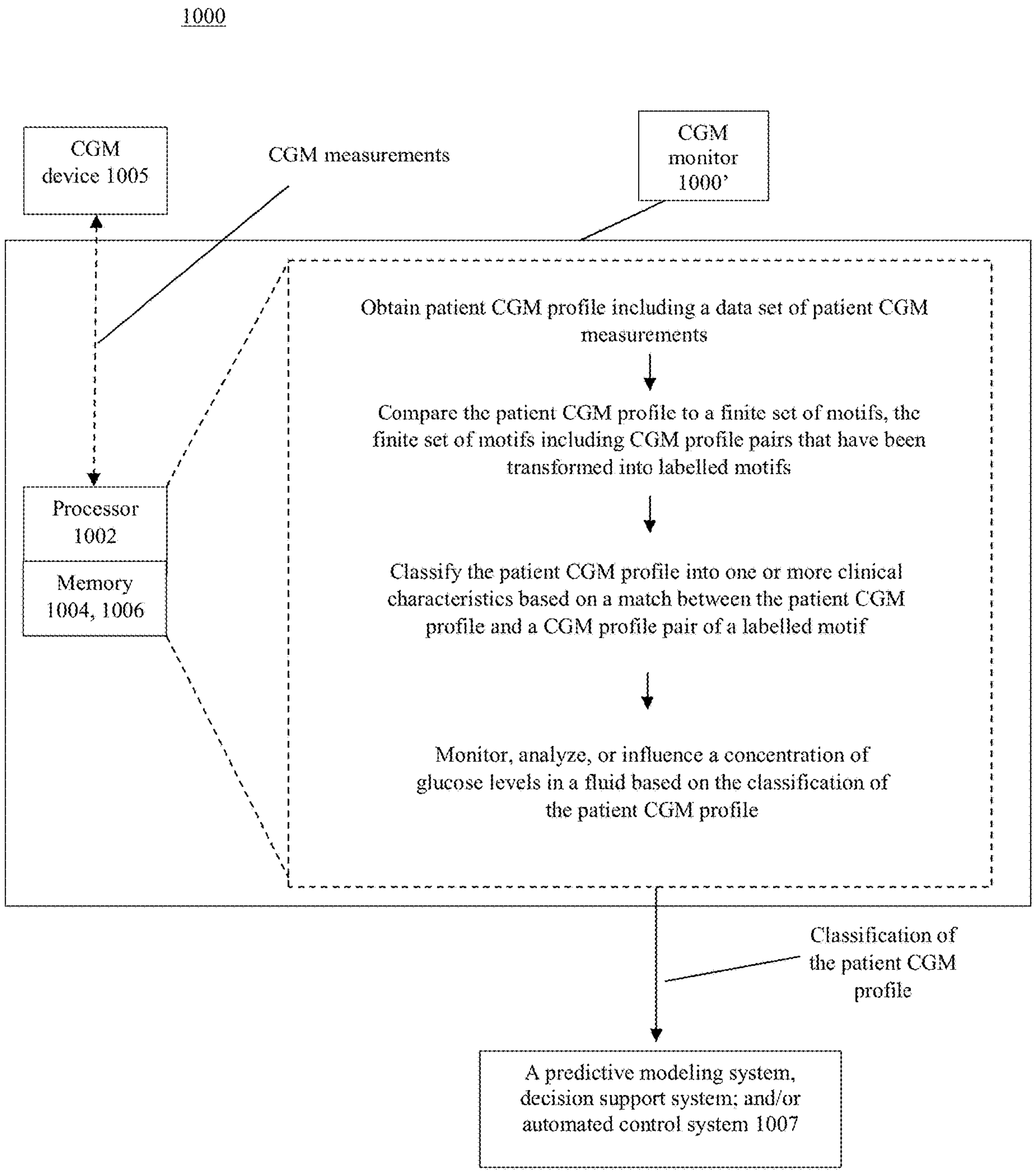
FIG. 1B shows an exemplary system diagram for classifying patient CGM data.

Referring to FIG. 1B, embodiments can relate to a system 1000 for classifying patient CGM data. The system 1000 can include a processor 1002. The system 1000 can include memory 1004, 1006. The memory 1004, 1006 can be associated with the processor 1002. The memory 1004, 1006 can have instructions 1024 stored thereon that when executed will cause the processor 1002 to execute algorithmic steps for classifying patient CGM data.

It should be noted that the processor 1002 for developing a model to classify CGM data can be the same processor or a different processor than the processor used for classifying patient CGM data. In addition, the system 1000 for developing a model to classify CGM data can be the same system or a different system than the system used for classifying patient CGM data.

The instructions 1024 can cause the processor 1002 to obtain one or more patient CGM profiles, each including a data set of patient CGM measurements. Any one or combination of the CGM data/measurements can be obtained from a CGM device 1005. This can be via a push or pull operation.

Any of the CGM devices 1005 disclosed herein can include a processor and sensor (e.g., electrochemical implant sensor) configured for monitoring of certain analytes or agents (e.g., glucose or lactate in fluids) from out readings of the sensor. The CGM device 1005 can be configured to monitor (obtain sensor readings and/or process sensor readings) in real-time, at periodic rates, or by some other scheme. The processor 1002 can be configured to be a component of, used in combination with, or in communication with the CGM device 1005. This can allow the processor 1002 to obtain output from the CGM device 1005 directly. In addition, or in the alternative, the CGM device 1005 can be in communication with a data store (e.g., a database 1003 or some other memory) and transmit its output to the data store. The processor 1002 can be configured to be in communication with the data store and retrieve the CGM data from the data store.

The instructions 1024 can cause the processor 1002 to compare the patient CGM profile to a finite set of motifs, the finite set of motifs including CGM profile pairs that have been transformed into labelled motifs. It is contemplated for each patient CGM profile to include CGM data points obtained over a predetermined time period and at a predetermined sample rate. It is further contemplated that each patient CGM profile is compared with a motif that was formed by CGM profile pairs that also had the same predetermined time period and at a predetermined sample rate.

The instructions 1024 can cause the processor 1002 to classify one or more patient CGM profiles into one or more clinical characteristics based on a match between the patient CGM profile and a CGM profile pair of a labelled motif. Matching can be determined by a degree of similarity between a patient CGM profile and a CGM profile pair of the motif. Exemplary matching operations were described above and more details regarding algorithmic steps of the matching are discussed below. For instance, identifying a match between a patient CGM profile and a CGM profile pair of a labelled motif can be based on a similarity of shapes of the patient CGM profile and the CGM profile pair of the labelled motif.

The instructions 1024 can cause the processor 1002 to monitor, analyze, or influence a concentration of glucose levels in a fluid based on the classification of the patient CGM profile.

The instructions 1024 can cause the processor 1002 to obtain the patient CGM profile from a CGM device 1005 and obtain the finite set of motifs from a database 1003. For instance, and as a non-limiting example, the patient CGM profile can be obtained directly from a CGM device 1005 (which may be real-time data). The finite set of motifs can be obtained from a database 1003, the finite set of motifs are motifs that were created from previously obtained CGM profiles.

The processor 1002 can be configured to be a component of, used in combination with, or in communication with another device/system 1007—e.g., his can include the processor 1002 being part of the device/system 1007, the device/system 1007 being part of the processor 1002, the processor 1002 in communication with the device/system 1007, etc. Being part of can include being on a same substrate or integrated circuit. For instance, the processor 1002 can be a component of, used in combination with, or in communication with a predictive modeling system (e.g., a system for predicting risk of hypo- or hyper-glycemia), a decision support system (e.g., a system for assisting with medical triage), and/or an automated control system (e.g., an artificial pancreas). The processor 1002 can provide the classification of one or more patient CGM profiles to assist with or augment the performance of these devices/systems 1007. For instance, the classification of one or more patient CGM profiles can provide a quick and accurate assessment of the patient CGM patient data to determine whether it has a clinical characteristic associated with time in range, time above range, time below range, etc. The classification of the patient CGM data can be used by the device/system 1007 to assist with or augment predicting or reacting to aspects of glycemic states, or assist with or augment determining or modifying insulin administration therapies.

Examples

As can be appreciated from the disclosure, 99.0% of CGM profiles (if not more) can be classified under a finite set of "motifs" (which may be referred to as representative daily profiles). For instance, studies have confirmed that 42,595 CGM profiles are able to be classified under a finite set of 483 motifs (the 483 motifs being identified from a training data set of 9,471 daily CGM profiles). The robustness of the set of motifs is established by using it to classify 99.0% (n=42,595) daily CGM profiles in a testing data set. The training and testing data sets are generated using the daily CGM profiles from six different studies (including the iDCL Protocol 3 and DIaMonD studies) which involved both type 1 and type 2 participants using a variety of treatment modes including MDI, pump therapy, and AID systems. Only 430 profiles could not be classified (matched to) one of the 483 motifs; the primary cause of the failure to match is the high percentage of out-of-range sensor readings in the unclassified daily CGM profiles. The 483 motifs are also grouped based on clinical characteristics including yime in Range, time above range, time below range, coefficient of variability, and standard deviation, which allows daily CGM profiles to be classified into an even smaller subset of prespecified groups with similar clinical characteristics.

Clinical guidance, decision support, and predictive modeling can be built around the motif profiles to make actionable insights easy to glean from a patient's CGM profile. This can expand the use of CGM in primary care spaces, as decision support tools for primary care providers can be created for gathering clinically actionable insights from patients' CGM profiles. Storing CGM daily profiles as a single data point representing the motif rather than 288 glucose readings per day is also be valuable in data compression to reduce data storage and transmission needs, which is increasingly important as more and more patient data is collected and stored.

Embodiments of the method can involve three steps: (i) Constructing and then fixing, a set of representative daily profiles, with the property that for any other daily CGM profile there is a representative daily profile that approximates the daily CGM profile, thereby preserving key clinically-relevant characteristics of the data. The set can be defined in terms of a radius around each representative daily profile, which can be varied until the set of representative daily profiles covers sufficiently well all possible daily CGM profiles; (ii) Approximation of any daily CGM profile by a representative daily profile, which involves computing a similarity metric (e.g. Euclidean distance in risk space) between the candidate daily CGM profile and each of the representative daily profiles, and selecting the single representative daily profile which best satisfies a threshold criterion; and (iii) Stratification of the set of representative daily profiles into subsets corresponding to health, pre-diabetes, or different variants of diabetes, e.g. type 1, variants of type 2, gestational diabetes. The threshold criterion can define the degree of fidelity between the daily CGM profile and the representative daily profile.

When these steps are accomplished, any daily CGM profile can be mapped to a representative daily profile, which can then be used as a surrogate for the original daily CGM profile. Potential applications of embodiments the method can include: (i) Structuring and dimensionality reduction—the nearly-infinite multitude of all possible daily CGM profiles can be reduced to a finite set of representative daily profiles which can be used as input to clinical and automated treatment algorithms; (ii) Indexing of a database to store daily CGM profiles with the subsets of the representative set of daily profiles; (iii) Classification and assessment/prediction of sub-types of diabetes (e.g. type 1, variants of type 2, gestational diabetes), based on the relative placing of an observed daily CGM profile into a subset of the representative set of daily profiles; and/or (iv) Compression/encryption of daily CGM profiles—instead of transmitting a daily CGM profile (typically 288 data points), a single number can be transmitted, which identifies the representative daily profile closest to the original daily CGM profile. At the receiving end, a decoder equipped with the set of representative daily profiles can reconstruct the daily CGM profile with a fidelity equal to the threshold criterion, preserving the key clinically-relevant characteristics of the original daily CGM profile.

Embodiments of the method can be adapted to work with daily CGM profiles having data points that are greater or lesser then 288, so long as the data points are equally spaced during the 24 hour time period. In addition, by adjusting the threshold criterion a larger or smaller set of representative daily profiles can be defined, and the degree of fidelity between candidate daily CGM profiles and the representative daily profiles can be managed.

One way to more fully leverage the information contained in the CGM data being collected can involve classifying daily CGM profiles. These classified profiles can then be used in predictive modeling, decision support and automated control systems (the latter known as the AP). For example, if intra-patient variability can be captured by differences in the sequence of daily CGM profiles that a patient moves through, then classification of each daily CGM profile is a prerequisite to modeling this phenomenon. While the average daily CGM profile over a couple of weeks, e.g., Ambulatory Glucose Profile (AGP), is a new paradigm for visualizing and quantifying the progress of the therapy of patients with diabetes, compared to the wealth of information carried by CGM time series and daily profiles, the information typically extracted from AGP is minute and based on rather primitive analytics, e.g. time in ranges (TIRs) [Battelino et al, 2019]. Thus, the field is wide open for new data retrieval applications using both contemporary data science and classic algebraic and statistical methods. One of the goals of the inventive method disclosed herein is to introduce advanced structuring and classification of CGM daily profiles, test with as many data sets as possible, and establish a quantitative framework for use by applications assisting analysis, treatment optimization, visualization, compression, and encryption of CGM data that will work in both type 1 and type 2 diabetes, for each individual patient.

Mathematically, embodiments of the method provides for a data-driven method to determine a set, Ω, which is a finite set of representative daily profiles such that almost any daily CGM profile generated by a patient can be matched to one of the representative daily profiles in Ω. In general, clustering is a typically unsupervised technique used to group data that is similar (according to some measure) into homogeneous groups (see Han et al. [2011, Chapter 10] for more details). Time series clustering applies the ideas behind clustering to time series, where a single piece of data to be clustered can be an entire time series or sub-sequences of a longer time series. The methods disclosed herein focus on pattern discovery (one of the four main applications of time series clustering [Aghabozorgi et al., 2015]) using data-based methods (see Liao [2005] for more details) to establish a finite set of representative daily CGM profiles. This choice is clinically relevant and motivated by the naturally occurring diurnal cycles in behavior, environment, physiology, etc.

There are a few examples in the literature of CGM time series data being used to perform clustering and classification. Hall et al. 2018 use spectral clustering to classify CGM patterns in CGM time series data that is 2.5 hours in length. The clustering produces 3 classes of glucose patterns (low, moderate, and severe variability over the 2.5 hour period), and they then use the patterns to assign a label to patients (i.e., group the patients). Kahkoska et al. [2019] use self-organizing maps to cluster eight features derived from CGM data. They are able to identify 3 clusters (groups of patients) in their demographic (youth with T1D and elevated hemoglobin A1c). Hall et al., 2018 use a data-driven approach they use 2.5 hour chunks of the CGM data, whereas the inventive method uses data from the entire day when performing the classification. In contrast, the work of Kahkoska et al., 2019 differs from the inventive method because Kahkoska et al. use the feature-based approach to time series clustering. Other examples of pattern discovery and anomaly detection can be found in the review by Woldaregay et al. 2019a, which reviews classification of specific CGM time series events (e.g., hypoglycemia, hyperglycemia) using a variety of machine learning methods. However, all published approaches, use clusters to define classes/groups of patients, whereas the inventive method focuses on classifying a single day of CGM data, and tracks the daily classification of profiles over time, for an individual patient.

Conceptually, the inventive method builds on ideas found in Yeh et al. 2016 and Kamgar et al. 2019. Yeh et al. 2016 contains the concept of a time series motif while Kamgar et al. 2019 contains the ideas behind finding conserved patterns. The inventive method, however, builds a set of representative daily profiles which can be used to classify almost any daily CGM profile generated by a patient. When this is accomplished, any daily CGM profile can be mapped to a representative daily profile, which can then be used as a surrogate for the original daily CGM profile.

The following discussion includes exemplary implementations for developing a model to classify continuous glucose monitoring (CGM) data and for classifying patient CGM data.

Structuring and Classification of Daily CGM Profiles

Embodiments of the method can include three steps: (i) Constructing and then fixing, a set of representative daily profiles representative daily profiles; (ii) Approximation of any daily CGM profile by a representative daily profile; and (iii) Stratification of the set of representative daily profiles into subsets.

Defining a Distance Metric Between a Pair of Daily CGM Profiles

Two daily CGM profiles match each other well if:

1. Their shapes match, and
2. Their relative location matches up.

As an extreme example, assume a pair of daily CGM profiles where one profile is a constant blood glucose value of 40 mg/dL all day and the second profile is a constant blood glucose value of 400 mg/dL all day. These should have the worst score (although they may be both horizontal lines parallel to the x-axis, the y-axis locations of each profile at each time point would be as different as is possible given the sensor range). At the other extreme, a pair of daily CGM profiles where both profiles have the same value over the entire day should have the best possible score (both the shape and relative location match exactly). Although there can be at least 27 similarity measures that can be used in time series clustering (see Table 3 of Aghabozorgi et al. 2015), Euclidean distance may be preferred. The Euclidean distance can be defined over a glucose risk-space, which can make the metric specific to diabetes. Measuring distance between daily CGM profiles may be achieved in risk space (defined in Kovatchev et al, 1997 and elaborated further in Kovatchev, 2017)—an approach that enhances the clinical resolution of the metric as the data digress into hypoglycemia, thereby equalizing the sensitivity (e.g., clinical sensitivity) of the metric over the entire glucose space. Thus, mathematically, the score between a pair of daily CGM profiles can be calculated as the Euclidean distance between the two profiles after each daily CGM profile had been transformed from blood glucose space to risk space [Kovatchev, 2017]. An exemplary formula for doing so can be $$f(x_i) = \ln(x_i)^{1.084} - 5.381 \tag{1}$$

where $x_i$ is a blood glucose value in mg/dL.

With this exemplary scoring system, the minimum score is 0 and the maximum score is 48.32. With this example, the maximum score is achieved when $x_i=-1.265$ and $y_i=1.583$ for i=1, . . . , 288, where −1.265 is the risk space equivalent of 40 mg/dL and 1.583 is the risk space equivalent of 400 mg/dL, the minimum and maximum sensor values respectively. There is a weighting effect of the transformation which places more weight on periods of hypoglycemia and less weight on periods of hyperglycemia.

Algorithmic Base for Defining the Set of Representative Daily Profiles

The algorithm identifies a degree of match between pairs of daily CGM profiles. The quality of the match can be quantified by the score (e.g., Euclidean distance) between the two profiles. The distance metric encodes how well the general shape and relative location of two daily CGM profiles match. When plotted on a graph (which is discussed in further detail and illustrated later), a good match occurs when two daily CGM profiles are almost on top of each other and have a very low distance score, and a bad match occurs when two daily CGM profiles do not have similar shapes and are not in the same relative location (e.g., have a very high distance score).

Thus, the inventive method can involve an initial step of computing the distances for every pair of daily CGM profiles in a data set. Subsequent steps can involve clustering the daily CGM profiles and define representative daily profiles.

Exemplary Single_Cluster Algorithm

Let $f(dp_j,dp_k)$ denote the score (Euclidean distance in risk space) between a pair of daily CGM profiles $dp_j$ and $dp_k$. Given a set of daily profiles $\phi$ that have yet to be assigned to a cluster, the following single_cluster algorithm can be used to define a single cluster $C_i$:

1. Find the pair of daily CGM profiles, say $dp_x$ and $dp_y$, such that $$f(dp_x, dp_y) \le f(dp_j, dp_k) \tag{2}$$

for all j, $k \in \phi$. That is $f(dp_x,dp_y)$ is the minimum score among all pairs of daily CGM profiles in $\phi$.

2. For each daily CGM profile $dp_j \in \phi dp_x$, $dp_y$, assign $dp_j$ to $C_i$ if and only if $$f(dp_x, dp_j) \le f(dp_x, dp_y) + r$$

or $$f(dp_y, dp_j) \le f(dp_x, dp_y) + r,$$

where r is the Cluster Radius—a tolerance value describing how close the match between $dp_j$ and one of $dp_x$ or $dp_y$ must be for $dp_i$ to be included in the cluster defined by $dp_x$ and $dp_y$.

Exemplary All_Clusters Algorithm

The following all_clusters algorithm can be used to define all the clusters (a clustering C) in a set of daily CGM profiles $\phi$:

1. Apply the single_cluster algorithm to $\phi$ to obtain the newest cluster $C_i$.
2. Update $\phi$ by removing all daily CGM profiles in $C_i$. If $\phi \equiv \emptyset$, all clusters have been obtained; otherwise return to Step 1.

As defined, the all_clusters algorithm will terminate when all daily CGM profiles have been assigned to a cluster. In practice this means that a cluster could consists of just two daily CGM profiles which are not very well matched (have a large score). To avoid this a threshold criterion $\gamma$ can be used so that if $f(dp_x, dp_y) > \gamma$ in Equation (2) of the single_cluster algorithm, the all_clusters algorithm will terminate. For example, the value of $\gamma$ can be set to 8.89, the $20^{th}$ percentile of all scores between pairs of daily CGM profiles in a DCLP1 data set.

Exemplary Classify_Profile Algorithm

For a cluster $C_i$, the set of two daily profiles $M_i=\{dp_x,dp_y\}$ that satisfy Equation (2) of the single_cluster algorithm define the cluster motif, the prototypical daily CGM profile that should belong to cluster $C_i$, denoted as $dp_{m_i}$. The cluster motif can be defined so that its value during the j-th time interval is simply the average of the two blood glucose values for the j-th time interval in $dp_x$ and $dp_y$. Because single_cluster may be a greedy algorithm, once the |C| clusters have been defined using the all_clusters algorithm, it may be beneficial to determine whether any daily CGM profiles assigned to a cluster can or should be reassigned. This can be accomplished using the classify_profile algorithm to assign each daily CGM profile $dp_k$ to the cluster $C_i$ where $$\min_{i=1,\ldots,|C|} f(dp_{m_i}, dp_k) \tag{3}$$

and $$f(dp_{m_i}, dp_k) \le f(dp_x, dp_y) + r \tag{4}$$

for $dp_x$, $dp_y \in M_i$, and where r is the same tolerance value used in Equation (2). Applying the classify_profile algorithm described above produces the final clustering. The end result is $\Omega$, which is a finite set of representative daily profiles such that almost any daily CGM profile generated by a patient can be matched, up to a threshold, to one of the representative daily profiles in $\Omega$. The set $$\{dp_{m_i} | i = 1, \ldots, |C|\}$$

is such a set.

Thus, a set of representative daily profiles can be constructed, with the property that for any other daily CGM profile there is a representative daily profile that approximates the daily CGM profile, thereby preserving key clinically-relevant characteristics of the data. The set can be defined in terms of a cluster radius around each representative daily profile, which can be varied until the set of representative daily profiles covers sufficiently well all possible daily CGM profiles.

Training and Test Data

For exemplary purposes, let us assume four data sets are used: one training data set and three testing data sets. A training data (DCLP1) can be used to construct the set of representative daily profiles, after which the representative daily profiles is fixed and used without further changes in test data sets (DCLP3, DIA1, and DIA2). With this strategy, the method can be developed and fixed in one data set and then applied prospectively to three different independent data sets, which ensures the method's validity across type 1 (DCLP3, DIA1) and type 2 diabetes (DIA2).

As a non-limiting example, DCLP1 can be a data set from a 3-month parallel group, multi-center, randomized unblinded trial where patients with T1D are assigned to receive treatment with a mobile closed-loop control (CLC) system or a sensor-augmented pump (SAP). DCLP1 can be taken to be the "the set of all possible daily CGM profiles" and can play the role of the training data set. DCLP3 can be a data set from a 6-month randomized, multi-center trial where patients with T1D are assigned in a 2:1 ratio to receive treatment with a CLC system or a SAP. DCLP3 can play the role of a testing set and can be used to make sure that the set of representative daily CGM profiles can be used to successfully classify a set of daily CGM profiles generated by T1D patients. DIA1 can be a data set from a randomized clinical trial that includes adults with T1D who used multiple daily insulin injections. DIA1 can play the role of a more general T1D testing set. DIA2 can be a data set from a randomized clinical trial of patients with T2D who received multiple daily insulin injections. DIA2 can play the role of a more general testing set.

The CGM sensors used in the four different studies (DCLP1, DCLP3, DIA1, and DIA2) can be configured to collect a blood glucose value (e.g., range [40, 400] mg/dL) approximately once every 5 minutes. With this exemplary implementation, a single daily CGM profile should include 288 data points (blood glucose values).

The possibility of missing data occurring in a single daily CGM profile is contemplated. Missing data in a single daily CGM profile can be interpolated using cubic splines, for example. However, because interpolation via cubic splines may require a data point on either end of the missing data interval, if the missing data interval included the first or last 5 minute interval in the 24 hour daily CGM profile, the method of interpolation can be backward or forward propagation of the next or last known value using the fillna function in Pandas.

Constructing a Set of Representative Daily Profiles Using the Training Data

Applying the all_clusters and classify_profile algorithms to the DCLP1 data set can be done to obtain Ω, the set of representative daily CGM profiles. The radius r in Equation (4) serves as a tolerance value that controls the size of the cluster $C_i$ by specifying how closely a daily CGM profile must match the cluster motif $dp_{m_i}$. In general, for a given data set, an increase in r will lead to an increase in the size of clusters obtained and consequently a decrease in the number of clusters obtained.

The optimal radius for use in the single_cluster and classify_profile algorithms is the radius r that minimizes the number of clusters and maximizes the quality of the clustering obtained. The Silhouette Coefficient [Rousseeuw, 1987], the Calinski-Harabasz index [Calinski and Harabasz, 1974], and the Davies-Bouldin index [Davies and Bouldin, 1979] are three metrics commonly used to measure the quality of a clustering. They all measure how homogeneous each cluster in the clustering is, and how well separated the clusters in the clustering are. However, these measures do not work well when the number of clusters are in the hundreds (for example the Silhouette Coefficient is commonly recommended as the method to find the optimal value of k in k-means clustering, where k is typically less than 10). Thus, another measure of the quality of the clustering may be desired.

For each cluster $C_i \in C$, the individual cluster residual sum of squares ($cRSS_i$) can be calculated as $$\sum_{dp_k \in C_i} \sum_{j=1}^{288} (dp_{m_i j} - dp_{kj})^2, \tag{5}$$

where $dp_{m_i j}$ and $dp_{kj}$ denote the risk space blood glucose value of the j-th time interval for the cluster motif and the k-th daily CGM profile in cluster $C_i$ respectively. Because clusters can be different sizes, the total clustering residual sum of squares (CRSS) can be calculated as the weighted sum of the individual cluster residual sum of squares, i.e., $$\sum_{i=1, \ldots, |C|} cRSS_i * \frac{|C_i|}{N} \tag{6}$$

where N is the total number of daily CGM profiles in the clustering ($\Sigma_{C_i \in C}|C_i|$). The lower the clustering residual sum of squares is, the better the clustering.

Assume the radius that minimizes the number of clusters and maximizes the quality of the clustering obtained is r=2.50. As such, the set of representative daily CGM profiles, Ω, is defined by the clustering obtained using the all_clusters and classify_profile algorithms described in relation to the DCLP1 data set, where r=2.50 in the single_cluster and classify_profile algorithm. Assume the clustering obtained using r=2.50 has 226 clusters, |Ω|=226 since Ω is composed of the motifs from each of the 226 clusters.

Thus, the set of representative daily profiles, Ω, has been constructed on the training DCLP1 data and is fixed thereafter for prospective application and validation in the test data sets DCLP3, DIA1, and DIA2.

Approximation of any Daily CGM Profile by a Representative Daily Profile

If Ω is truly robust, it should be able to approximate and classify almost any daily CGM profile presented to it, regardless of the patient who generated the profile (i.e., they could be a T1D or T2D patient, they could be using a pump or not, etc.). The robustness and representativeness of Ω is then established by using Ω and the classify_profile algorithm to classify any daily CGM profile. Further, when a daily CGM profile is approximated by a representative daily profile from Ω, the clinical metrics representing the glycemic state of the person on that day should be close between the original daily CGM profile and its corresponding representative daily profile. These two properties can be tested using Ω as fixed in the training DCLP1 data and then applied without modification to the independent data sets DCLP3, DIA1, and DIA2.

Robustness of the Set of Representative Daily Profiles

The robustness of Ω can be established by using Ω and the classify_profile algorithm to classify each daily CGM profile $dp_k$ in the three different testing sets (DCLP3, DIA1, and DIA2). Note that if Equation (3) and Equation (4) of the classify_profile algorithm are not satisfied for a particular daily CGM profile $dp_k$, then that daily CGM profile cannot be classified.

Extreme Cases of Approximation Failure

When the blood glucose value lies outside of the range of the sensor (40 mg/dL to 400 mg/dL for the example provided above), the sensor may report a placeholder value indicating this. For example, a value of 39 mg/dL can be reported if the blood glucose value is below the sensor range while a value of 401 mg/dL can be reported if the blood glucose value is above the sensor range. An analysis of the daily CGM profiles left unclassified reveals that, regardless of data set, the percentage of CGM sensor readings equal to 39 or 401 in unclassified daily CGM profiles is substantially larger than the percentage of CGM sensor readings equal to 39 or 401 in classified daily CGM profiles. Given the striking differences in percentage of CGM sensor readings equal to either 39 or 401 between the 226 motifs and the unclassified daily CGM profiles, it can be concluded that, when present in a daily CGM profile, these sensor error codes are the main factor for failure of the approximation with a representative daily profile from Ω.

Approximation of Clinical Metrics of Glycemic Control

The following metrics (see Table 1 of Kovatchev [2017] for their clinical relevance) can be calculated for each representative daily profile using each of the four data sets (DCLP1, DCLP3, DIA1, and DIA2)

1. The mean blood glucose (BG) value,
2. The Time in Range (TIR, the percentage of 5-minute intervals over the 24-hour period in which the blood glucose value is greater than or equal to 70 mg/dL but less than on equal to 180 mg/dL),
3. The Time Above Range (TAR, the percentage of 5-minute intervals over the 24-hour period in which the blood glucose value is strictly greater than 180 mg/dL),
4. The Time Below Range (TBR, the percentage of 5-minute intervals over the 24-hour period in which the blood glucose value is strictly less than 70 mg/dL),
5. The Low Blood Glucose Index (LBGI, a measure of the risk of hypoglycemia where a higher value indicates greater and more frequent hypoglycemic excursions), and
6. The High Blood Glucose Index (HBGI, a measure of the risk of hyperglycemia where a higher value indicates greater and more frequent hyperglycemic excursions).

The metrics, which represent the glycemic state of the person on a given day, can be used to assess the similarity between the representative daily profile and the average daily CGM profile placed in the cluster defined by the representative daily profile. Ideally, these cluster-specific metrics should be "agnostic" to the patient population, treatment, or level of disease progression of the patients who generated the daily CGM profiles. Scatterplots can be made for the four different data sets: DCLP1 (Training) and DCLP3, DIA1, DIA2 (Testing). FIGS. 11A, 11B, 11C, 11D, 11E, and 11F show correlation scatter plots for Representative Daily Profiles in Ω versus the daily CGM profiles in DCLP1, for six clinically relevant metrics. FIGS. 12A, 12B, 12C, 12D, 12E, and 12F show correlation scatter plots for Representative Daily Profiles in Ω versus the daily CGM profiles in DCLP3, for six clinically relevant metrics. FIGS. 13A, 13B, 13C, 13D, 13E, and 13F show correlation scatter plots for Representative Daily Profiles in f versus the daily CGM profiles in DIA1, for six clinically relevant metrics. FIGS. 14A, 14B, 14C, 14D, 14E, and 14F show correlation scatter plots for Representative Daily Profiles in Ω versus the daily CGM profiles in DIA2, for six clinically relevant metrics. Each point on a scatterplot is $(x_j, y_{jk})$ where $x_j$ is the value of the metric for the j-th representative daily profile from Ω and $y_{jk}$ is the mean value of the metric for all daily CGM profiles from data set k∈{DCLP1, DCLP3, DIA1, DIA2} which are assigned to the cluster defined by the j-th representative daily profile, where j={1, . . . , 226}. As will be discussed in more detail and illustrated later, the plots show a high degree of correlation regardless of the data set being considered.

A more detailed explanation of the algorithms and exemplary implementation of the method follows.

Scoring the Match Between Two Daily CGM Profiles

A daily CGM profile can defined as the 24-hour CGM time series from 12:00:00 am to 11:59:59 pm. Assuming that a glucose data point is recorded every 5 minutes, a daily CGM profile is a time series with 288 data points. Two daily CGM profiles match each other well if 1) Their shapes match, and 2) Their relative locations in blood glucose space match.

As noted above, at one extreme, a pair of daily CGM profiles where one profile is a constant blood glucose value of 40 mg/dL all day and the second profile is a constant blood glucose value of 400 mg/Dl all day should have the worst score (although they are both horizontal lines parallel to the x-axis, the y-axis locations of each profile at each time point is as different as is possible given the sensor range). At the other extreme, a pair of daily CGM profiles where both profiles have the same value at each time point over the entire day should have the best possible score (both the shape and relative location match exactly).

Although there are at least 27 similarity measures that are used in time series clustering, root mean squared error (RMSE), a version of Euclidean distance, is selected with this exemplary implementation because the methods used in this work are derived from the approaches by Yeh et al. who used Euclidean distance. As shown below, RMSE meets the 2 criteria outlined above. The advantage of RMSE over simple Euclidean distance is that RMSE normalizes the Euclidean distance by incorporating the number of data points used in the computation, and this allows two scores to be compared even if all the daily CGM profiles used to compute the two scores have a different number of data points. A daily CGM profile having less than 288 data points commonly can arise when a sensor fails to record data or the data recorded does not get uploaded, if the sampling resolution of the sensor is greater than 5 minutes, etc.

Prior to calculating the RMSE between a pair of daily CGM profiles, each daily CGM profile is first transformed from blood glucose space to risk space using the following formula, first defined in 1997 by Kovatchev et al. and further elaborated in 2017 by Kovatchev:

$$g(x_t) = \ln(x_t)^{1.084} - 5.381 \qquad (7)$$

Figure 2A:
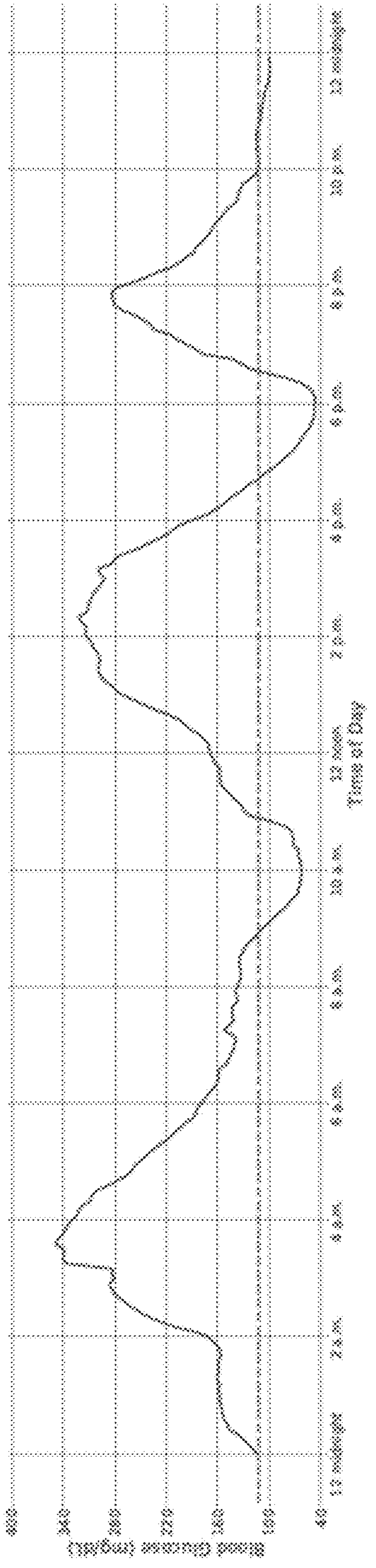
FIGS. 2A and 2B illustrate how periods of hypoglycemia that occur in a daily CGM profile plotted in blood glucose space (FIG. 2A) are weighted by the risk space transformation of the daily CGM profile (FIG. 2B), wherein the horizontal dotted line marks the "clinical center" of the scale at 112.5 mg/dL in FIG. 2A and 0 in FIG. 2B.
Figure 2B:
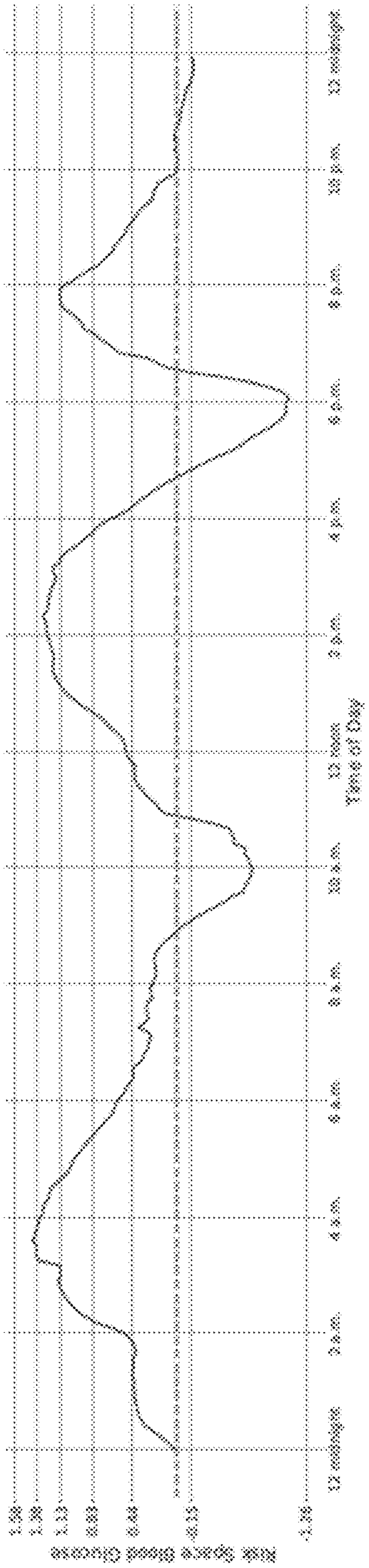

$x_t$ is a blood glucose value in mg/dL. This transformation enhances the clinical resolution of the metric as the data digress into hypoglycemia, thereby equalizing the (clinical) sensitivity of the metric over the entire glucose space. The two plots shown in FIGS. 2A and 2B illustrate the weighting effect of the transformation which places more weight on periods of hypoglycemia and less weight on periods of hyperglycemia. FIG. 2A displays the daily CGM profile in blood glucose space; the distance between the hyperglycemic peak at 3:38 am and the horizontal line is 236.5 mg/dL, and the distance between the hypoglycemic nadir at 6:08 pm and the horizontal line is 66.5 g/dL, a ratio of 3.55. FIG. 2B displays the daily CGM profile in risk space; in risk space the distances are 1.41 and 1.10 respectively, resulting in a ratio of 1.29.

Let $f(dp_j, dp_k)$ denote the score between a pair of daily CGM profiles $dp_j$ and $dp_k$. Then $$f(dp_j, dp_k) = 10 \cdot \sqrt{\frac{\sum_{t=1}^{N} \left(g(dp_{jt}) - g(dp_{kt})\right)^2}{N}}, \tag{8}$$

Figure 3A:
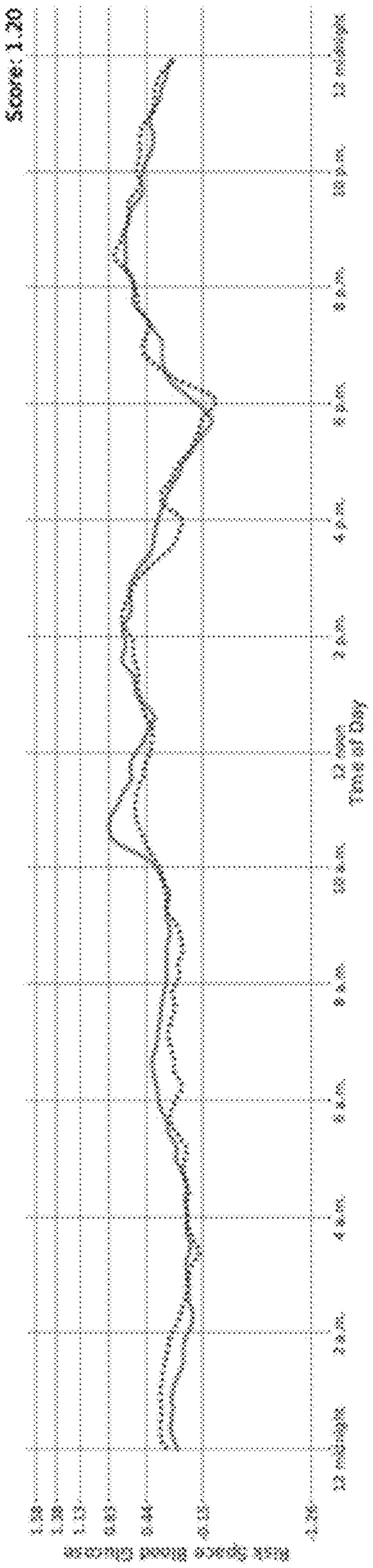
FIGS. 3A and 3B show a good match (FIG. 3A) and bad match (FIG. 3B) between pairs of daily CGM profiles, wherein in each case the quality of the match is apparent visually and quantified by the score between the two profiles.
Figure 3B:
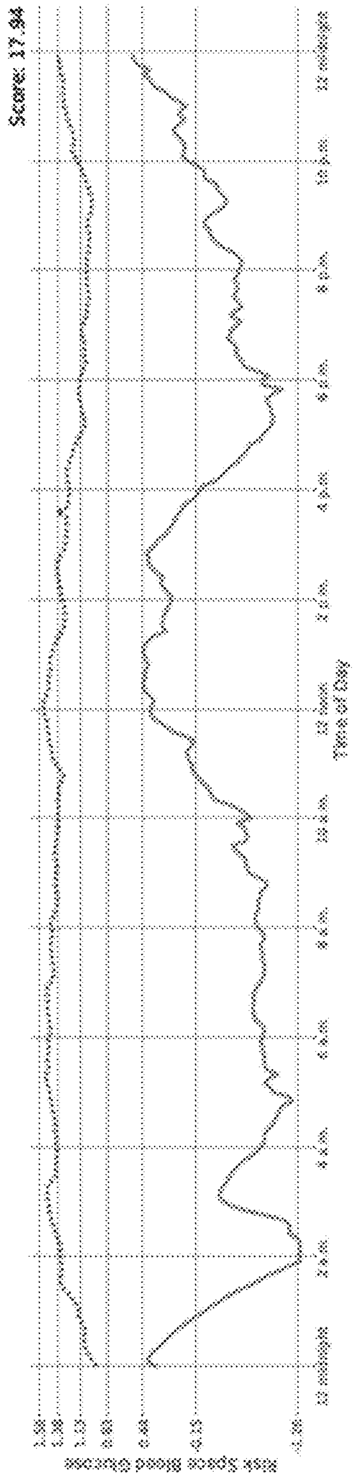

Scoring the match between two daily CGM profile where N (≤288) is the number of time points where both $dp_j$ and $dp_k$ have data, and where the RMSE is multiplied by 10 for tractability of the resulting score. The maximum score of 28.47 is achieved when $g(x_t)=g(40)=-1.265$ and $g(y_t)=g(400)=1.583$ for all t, where 40 mg/dL and 400 mg/dL are the minimum and maximum sensor values respectively. FIGS. 3A and 3B indicate that the scoring system encodes how well the general shape and relative location of two daily CGM profiles match up: FIG. 3A where the two daily CGM profiles are almost on top of each other has a very low score of 1.20, while FIG. 3B where the two daily CGM profiles do not have similar shapes and are not in the same relative location has a much higher score of 17.94.

Determining the Set of Representative Daily Profile.

Given a set of daily profiles p that have yet to be assigned to a cluster, the following single_motif algorithm is used to define a single cluster $C_i$ and its associated motif $m_i$:

1) Find the pair of daily CGM profiles, say $dp_x$ and $dp_y$, such that $$f(dp_x, dp_y) \le f(dp_j, dp_k) \tag{9}$$

for all $j, k \in \rho$. That is $f(dp_x, dp_y)$ is the minimum score among all pairs of daily CGM profiles in ρ.

2) For each daily CGM profile $dp_j \in \rho \setminus \{dp_x, dp_y\}$, assign $dp_j$ to $C_i$ if and only if $$f(dp_x, dp_j) \le f(dp_x, dp_y) + \tau$$

or $$f(dp_y, dp_j) \le f(dp_x, dp_y) + \tau,$$

where τ is a tolerance value describing how close the match between $dp_j$ and one of $dp_x$ or $dp_y$ must be for $dp_j$ to be included in the cluster defined by $dp_x$ and $dp_y$.

For a cluster $C_i$, the set of two daily profiles $M_i=\{dp_x, dp_y\}$ that satisfy Equation (9) define the cluster motif pair. The cluster motif $m_i$ is a single daily profile defined so that its value during the j-th time interval is simply the average of the two blood glucose values for the j-th time interval in $dp_x$ and $dp_y$. The cluster motif $m_i$ is the prototype of the daily CGM profile that should be in cluster $C_i$.

The following all_motifs algorithm is used to define all the clusters (a clustering C) in a set of daily CGM profiles ρ.

1) Apply the single_motif algorithm to ρ to obtain the newest cluster $C_i$.

2) Update ρ by removing all daily CGM profiles in $C_i$. If $\rho \equiv \emptyset$, all clusters have been obtained; otherwise return to Step 1.

As defined, the all_motifs algorithm will terminate when all daily CGM profiles in ρ have been assigned to a cluster. In practice this means that a cluster motif could be defined by two daily CGM profiles that are not very well matched. To avoid this scenario a threshold criterion γ is used so that if $f(dp_x; dp_y) > \gamma$ in Equation (9) of the single_motif algorithm, the all_motifs algorithm will terminate. Because γ represents the maximum possible score between two daily CGM profiles that will form a motif pair, γ should be chosen so that having a motif pair with a score of γ is acceptable.

The all_motifs algorithm defines a procedure which can be used on a data set of "all possible daily CGM profiles" to determine a finite set of motifs. This finite set of motifs $$\{m_i \mid i = 1, \ldots, |C|\}$$

is a finite set of representative daily profiles such that almost any daily CGM profile generated by a patient can be matched to one of the representative daily profiles in this set, and finding such a set is the main purpose of this research.

Classifying a Daily CGM Profile

The classify_profile algorithm assigns the label l to a daily CGM profile $dp_k$ where $$l = \min_{i=1,\ldots,|C|} f(m_i, dp_k) \tag{10}$$

and $$f(m_l, dp_k) \le f(dp_x, dp_y) + \tau \tag{11}$$

for $dp_x, dp_y \in M_l$, and where τ is the same tolerance value used in Equation (9). Note that if Equation (10) and Equation (11) of the classify_profile algorithm are not satisfied for a particular daily CGM profile $dp_k$, then $dp_k$ cannot be classified using.

When the classify_profile algorithm is applied to a data set of daily CGM profiles, the resulting classification can be thought of as a clustering, where a daily CGM profile $dp_k$ which best matches a motif $m_l$ is assigned to the cluster $C_l$ of all daily CGM profiles in the data set which which are assigned the label l by the classify_profile algorithm. Note that the clustering obtained using the procedure outlined in this section is a clustering which results from the classification of daily CGM profiles in a data set and is separate from the clustering of daily CGM profiles, which is a clustering of the set of "all possible daily CGM profiles" that is used to define Ω, the set of representative daily profiles.

Data

There are six different data sets used in this exemplary implementation:

1) DCLP1 is a data set from a 3-month parallel group, multi-center, randomized un-blinded trial (The International Diabetes Closed Loop (iDCL) Trial: Protocol 1; NCT02985866) where patients with T1D are assigned to receive treatment with a mobile closed-loop control (CLC) system or a sensor-augmented pump (SAP). The trial had 125 patients with 64 assigned to the CLC group, and there are 8,980 days post-randomization with at least one CGM data point.

2) DCLP3 is a data set from a 6-month randomized, multi-center trial (iDCL Protocol 3: Acceptance of the Artificial Pancreas; NCT03563313) where patients with T1D are assigned in a 2:1 ratio to receive treatment with a CLC system or a SAP. The trial had 168 patients with 112 assigned to the CLC group, and there are 30,657 days post-randomization with at least one CGM data point.

3) DIA1 is a data set from a randomized clinical trial (Multiple Daily Injections and Continuous Glucose Monitoring in Diabetes [DIaMonD]; NCT02282397) that included 158 adults with T1D who are using multiple daily insulin injections, with 105 patients assigned to the group using CGM, and there are 20,753 days with at least one CGM data point. Although the patients in the DIA1 data set also have T1D, the patients in DIA1 do not use a pump like the patients in the DCLP1 and DCLP3 data sets.

4) DIA2 is a data set from a randomized clinical trial (DIaMonD; NCT02282397) of 158 patients with T2D who are receiving multiple daily insulin injections (MDI), with 79 assigned to the group using CGM, and there are 11,136 days with at least one CGM data point.

5) DSS1 is a data set from a randomized clinical trial (Diabetes Support System; NCT03093636) of 80 patients with T1D who are receiving MDI. There are 6,691 days with at least one CGM data point.

6) NTLT is a data set from a randomized crossover clinical trial (Nightlight; NCT02679287) of 80 patients with T1D, who underwent one of two sequences of four 8-week treatment sessions involving CLC and SAP. There are 17,527 days with at least one CGM data point.

The six different data sets contained de-identified data from the published studies referenced above. Table I shows pertinent patient information for each data set.

The data from these six different data sets is divided into three different sets: a training data set (15%), a validation data set (25%), and a testing data set (65%). The training data set is used to determine the set of representative daily profiles $\Omega_\tau$ for $\tau \in \gamma' \Upsilon = \{0.50, 0.75, \ldots, 2.00, 2.25\}$. The daily CGM profiles in the validation data set are then classified using each set of representative daily CGM profiles $\Omega_\tau$, and the results are used to select the final value of $\tau$ to select $\Omega$. Finally, the performance of $\Omega$ is evaluated by using it to classify the (unseen) daily CGM profiles in the testing data set.

Each patient from each arm of each trial of the 6 data sets is randomly assigned to one of the training, validation, and testing sets. For example, in the DCLP3 trial patients are assigned 2:1 to the trial arm. In this case, the proportion of DCLP3 trial arm patients to DCLP3 control arm patients in the training, validation, and testing sets is also approximately 2:1.

The CGM sensors used in the six different studies collect a blood glucose value (range [40, 400] mg/dL) approximately once every 5 minutes; thus in a single daily CGM profile there should be 288 data points (blood glucose values). In order to maximize the number of daily CGM profiles with usable data, two sets of criteria are developed:

1) "As-Is" criteria:
   a) Strictly less than a 50 mg/dL change in blood glucose value from one 5-minute interval to the next, and
   b) A maximum missing data interval of length 10 minutes and at most 50% of the data missing (144 data points), or
   A maximum missing data interval of length 15 minutes and at most 33.3% of the data missing (96 data points), or
   A maximum missing data interval of length 20 minutes and at most 25% of the data missing (72 data points), or
   A maximum missing data interval of length 60 minutes and at most 12.5% of the data missing (36 data points).
2) "Interpolate" criteria:
   a) Strictly less than a 50 mg/dL change in blood glucose value from one 5-minute interval to the next, and
   b) A maximum missing data interval of length 20 minutes and at most 10% of the data missing (28 data points).

For each of the six data sets, the number of daily CGM profiles which satisfy the "As-Is" set of criteria and the "Interpolate" set of criteria are shown in Table II. The daily CGM profiles which satisfy the "As-Is" criteria are daily profiles for which there is enough data to attempt to classify the daily CGM profile. The daily CGM profiles which satisfy the "Interpolate" criteria are daily CGM profiles for which interpolation makes sense. Missing data in a single daily CGM profile is interpolated:

1) Using cubic splines (via the CubicSpline function in SciPy) if there are at least two data points on either end of the missing data interval,
2) Using linear interpolation if there is only a single data point on either end of the missing data interval, or
3) Using backward or forward propagation of the next or last known value (via the fillna function in Pandas) if the missing data interval included the first or last 5 minute interval in the 24 hour daily CGM profile.

The training data set is composed solely of daily CGM profiles which satisfied the "Interpolate" criteria, while the validation and testing sets are composed of daily CGM profiles which satisfy either the "As-Is" criteria or the "Interpolate" criteria. Because each patient has a variable number of daily CGM profiles, although patients are randomly assigned to the training, validation, and testing sets in a 15%, 20%, and 65% split, the training data set ended up with 9,741 daily CGM profiles (14.6%), the validation data set with 14,175 daily CGM profiles (21.3%), and the testing data set with 42,595 daily CGM profiles (64.0%).

Results

This section presents the results of using the all_motifs and classify_profile algorithms together with the training and validation data sets to obtain $\Omega$, the set of representative daily profiles. The robustness and representative-ness of $\Omega$ is then established by using $\Omega$ and the classify_profile algorithm to classify the daily CGM profiles in the testing data set. Finally, the last part of this section explores the sensitivity of the distribution of daily CGM profiles to clusters defined by the motifs in $\Omega$ when patients with different sub-types of diabetes generate the daily CGM profiles.

TABLE I

Data set characteristics for the data sets used in this paper.

| | DCLP1 | DCLP3 | DIA1 | DIA2 | DSS1 | NTLT |
|---|---|---|---|---|---|---|
| Diabetes type | T1D | T1D | T1D | T2D | T1D | T1D |
| Therapy | SAP, CLC | SAP, CLC | MDI | MDI | MDI | SAP, CLC |
| Number of patients (Exp. Group) | 125 (64) | 168 (112) | 158 (105) | 158 (79) | 80 (57) | 80 (40) |
| Age, years | | | | | | |
| Mean | 32.5 | 33.0 | 47.7 | 60.0 | 35.3 | 42.3 |
| Range | 14-75 | NR | 26-73 | 35-79 | NR | NR |
| Sex, % female | 47 | 50 | 44 | 56 | 56 | 66 |
| Race, % white | 87 | 89 | NR | 63 | 81 | NR |
| BMI, mean | NR | NR | 27.5 | 36.0 | 27.3 | NR |
| HbA1c, mean, % | 7.4 | 7.4 | 8.6 | 8.5 | 7.5 | 7.4 |
| Weight, mean, kg | NR | NR | 82.5 | 101.5 | NR | NR |

Abbreviations:
BMI, body mass index;
CLC, closed-loop control;
MDI, multiple daily injections;
NR, not reported;
SAP, sensor-augmented pump,
T1D, type one diabetes;
T2D, type two diabetes.

TABLE II

Number of daily CGM profiles in each of the 6 data sets with at least 1 data point, and which satisfy the "As-Is" and "Interpolate" sets of criteria.

| | At Least 1 Data Point | Satisfy "As-Is" Criteria | Satisfy "Interpolate" Criteria |
|---|---|---|---|
| DCLP1 | 8,980 | 5,542 (62%) | 4,891 (54%) |
| DCLP3 | 30,657 | 24,787 (81%) | 22,738 (74%) |
| DIA1 | 20,753 | 13,125 (63%) | 11,374 (55%) |
| DIA2 | 11,136 | 7,408 (67%) | 6548 (59%) |
| DSS1 | 6,691 | 4,335 (65%) | 4,062 (61%) |
| NTLT | 17,527 | 12,577 (72%) | 11,166 (64%) |

Finding Ω

In Equation (9) of the single_motif algorithm, the value γ is the maximum possible score between two daily CGM profiles that will form a motif pair. In the results that follow, γ is set to 5.26, which corresponds to the $20^{th}$ percentile of scores between all pairs of 9,741 daily CGM profiles in the training data set. Values of γ=4.64 and γ=4.98, corresponding to the $10^{th}$ and $15^{th}$ percentiles of scores respectively, are explored and while the results remain largely the same, for a given tolerance τ the number of unclassified daily CGM profiles tended to increase as γ decreased. This is an undesirable effect given that the main aim of this research is to find a set Ω such that almost all daily CGM profiles can be classified, and motivated the choice of γ=5.26.

In general, for a given data set an increase in τ will lead to a decrease in the number of clusters obtained and an increase in the average size of clusters obtained. Let $\Omega_\tau$ be the set of representative daily profiles obtained by applying the all_motifs algorithm with tolerance τ to the training data set. Eight different sets of representative daily profiles are generated using $\tau \in \Upsilon = \{0.50, 0.75, \ldots 2.00, 2.25\}$. Each set $\Omega_\tau$ is used to classify the daily CGM profiles in the validation data set using the classify_profile algorithm, and the statistics describing the clustering obtained for each tolerance $\tau \in \Upsilon$ are presented in Table III. The results indicate that as the tolerance increases, The number of clusters in the clustering obtained decreases (i.e., the number of motifs in $\Omega_\tau$ decreases), The average size of the cluster increases, and The total number of daily CGM profiles in the validation data set that are classified decreases.

TABLE III

Characteristics of each clustering obtained by applying the classify_profile algorithm to the validation data set (14,175 daily CGM profiles) using $\Omega_\tau$, the set of representative daily profiles obtained using tolerance $\tau \in \gamma$.

| τ | No. of Clusters | Unclassified Profiles (%) | Cluster Size Mean (Stdev) | Max. Cluster Size |
|---|---|---|---|---|
| 0.50 | 1781 | 347 (2.4) | 7.76 (6.61) | 48 |
| 0.75 | 1098 | 260 (1.8) | 12.67 (10.47) | 71 |
| 1.00 | 719 | 206 (1.5) | 19.43 (18.01) | 167 |
| 1.25 | 483 | 132 (0.9) | 29.07 (30.76) | 219 |
| 1.50 | 356 | 81 (0.6) | 39.59 (49.90) | 381 |
| 1.75 | 272 | 43 (0.3) | 51.96 (71.01) | 576 |
| 2.00 | 200 | 70 (0.5) | 70.53 (103.78) | 837 |
| 2.25 | 183 | 25 (0.2) | 77.32 (127.81) | 902 |

Figure 4A:
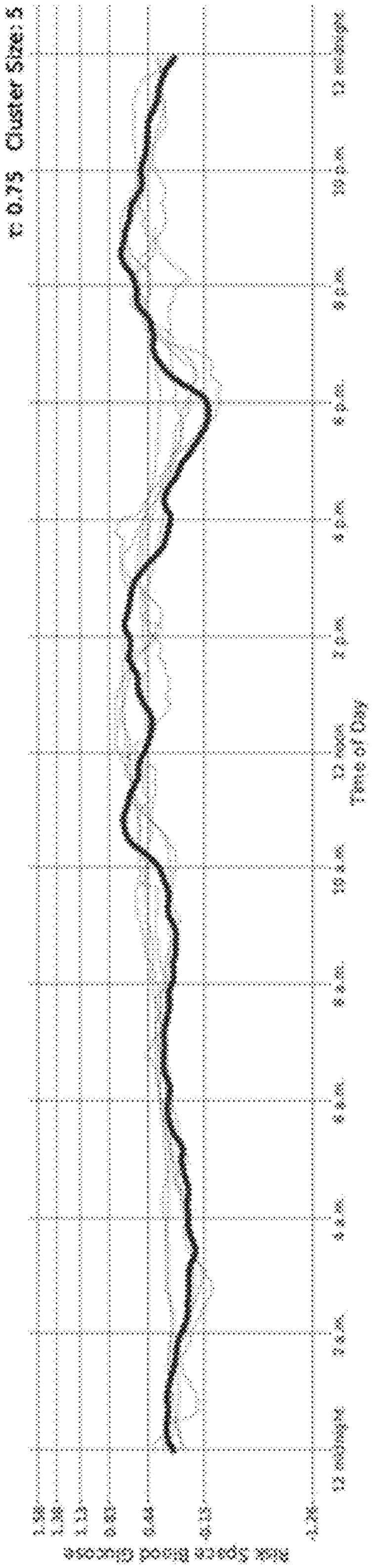
FIGS. 4A, 4B, 4C, and 4D shows composition of the cluster obtained for motif m E when using 1 and the classify_profile algorithm to classify daily CGM profiles from the validation data set, wherein $\tau$=0.75 (FIG. 4A), 1.25 (FIG. 4B), 1.75 (FIG. 4C), and 2.25 (FIG. 4D).
Figure 4B:
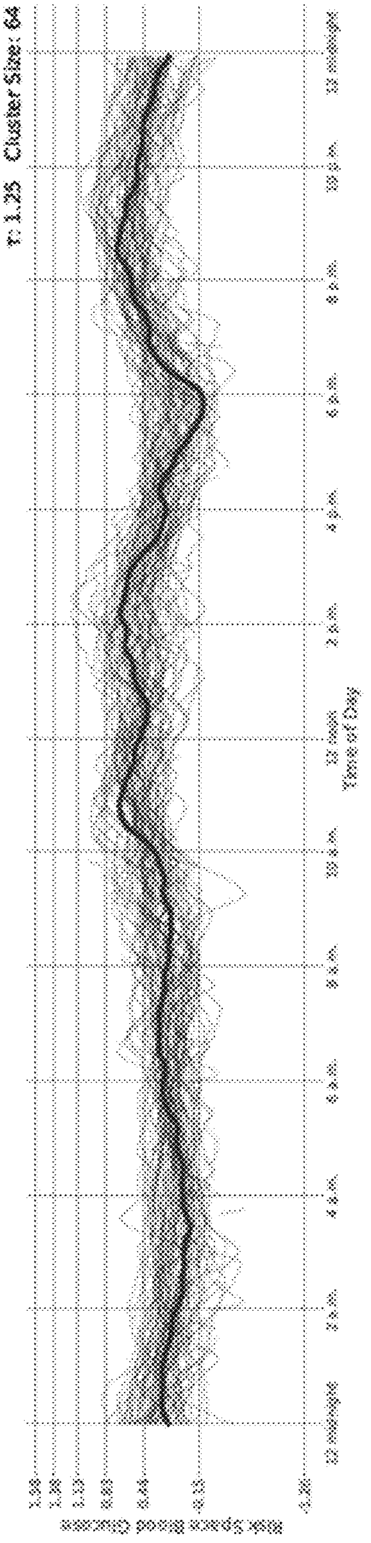
Figure 4C:
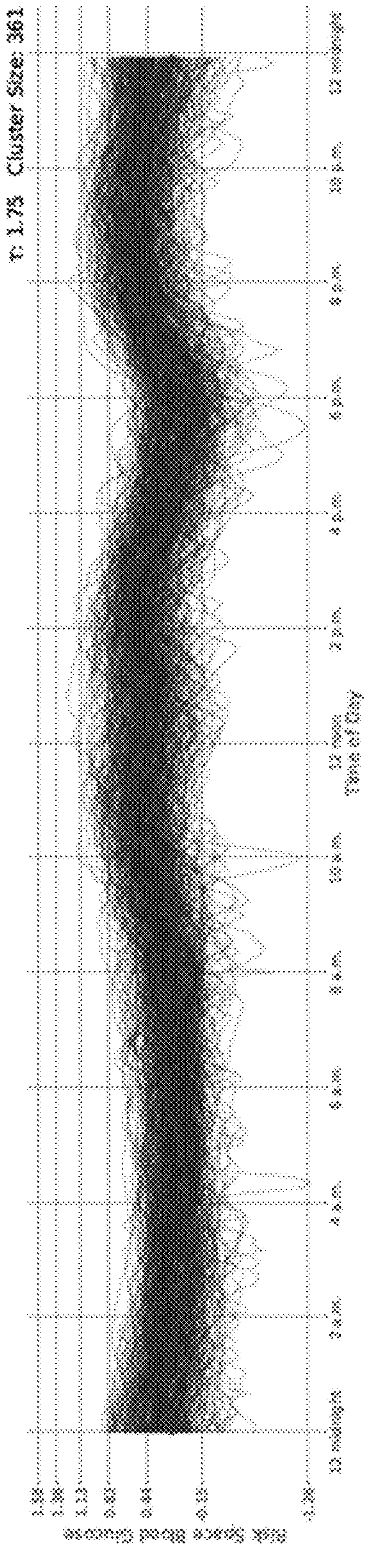
Figure 4D:
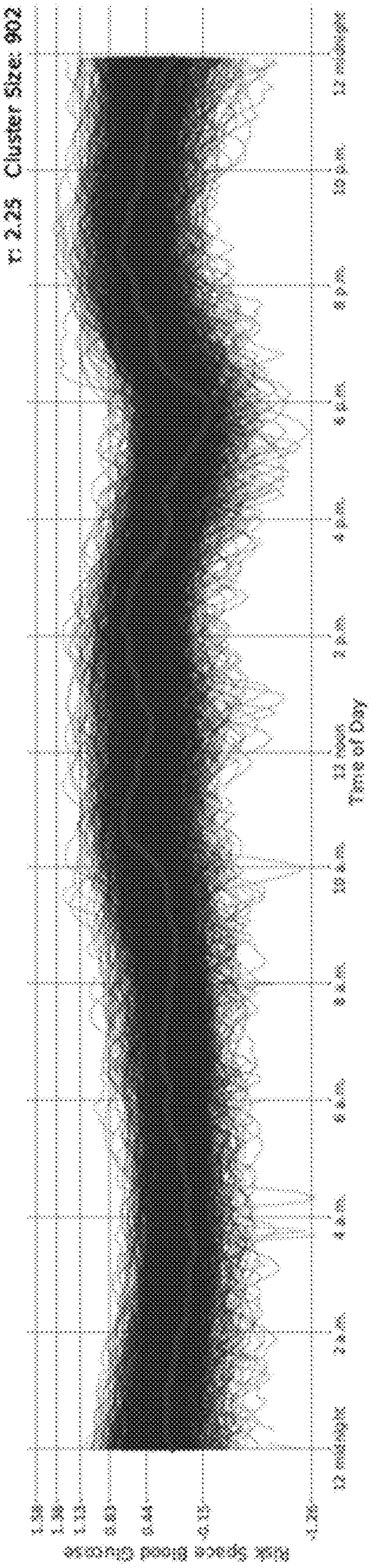
Figure 5A:
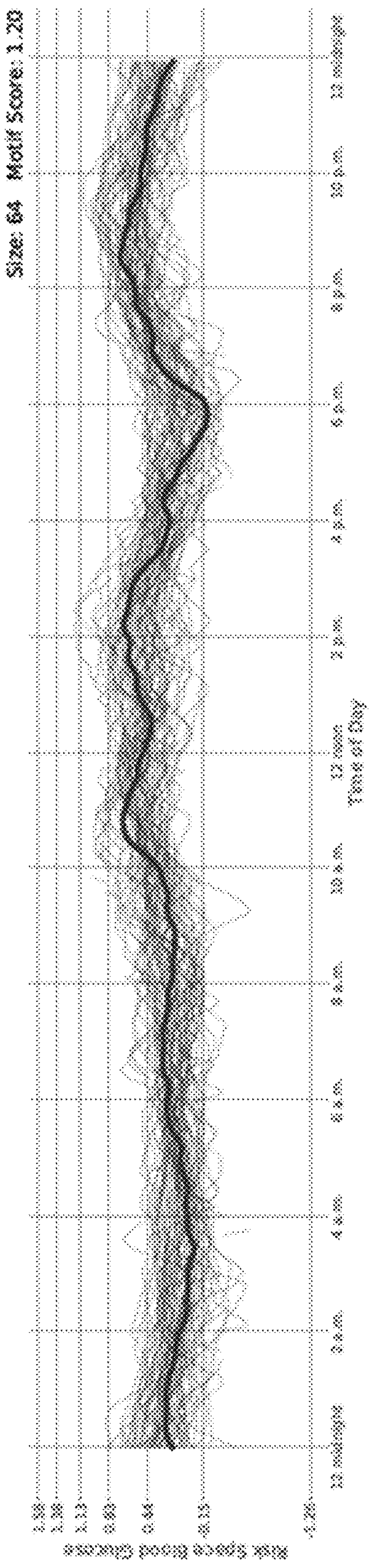
FIGS. 5A, 5B, 5C, and 5D show composition of cluster $C_i$ for (from top to bottom) $i \in \{1, 200, 400, 483\}$ obtained by using the single_motif algorithm with $\tau$=1.25, to classify daily CGM profiles from the validation data set.
Figure 5B:
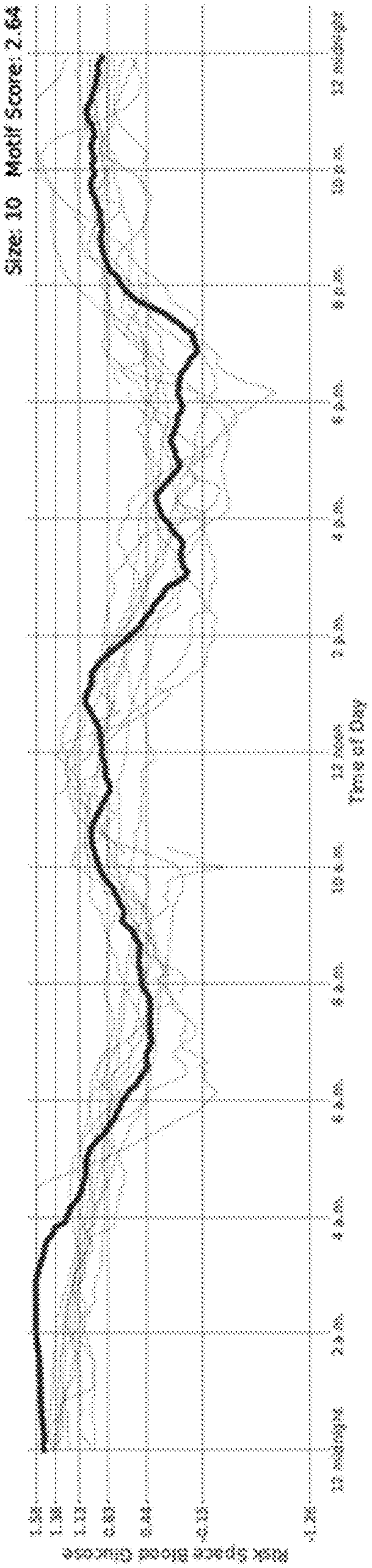
Figure 5C:
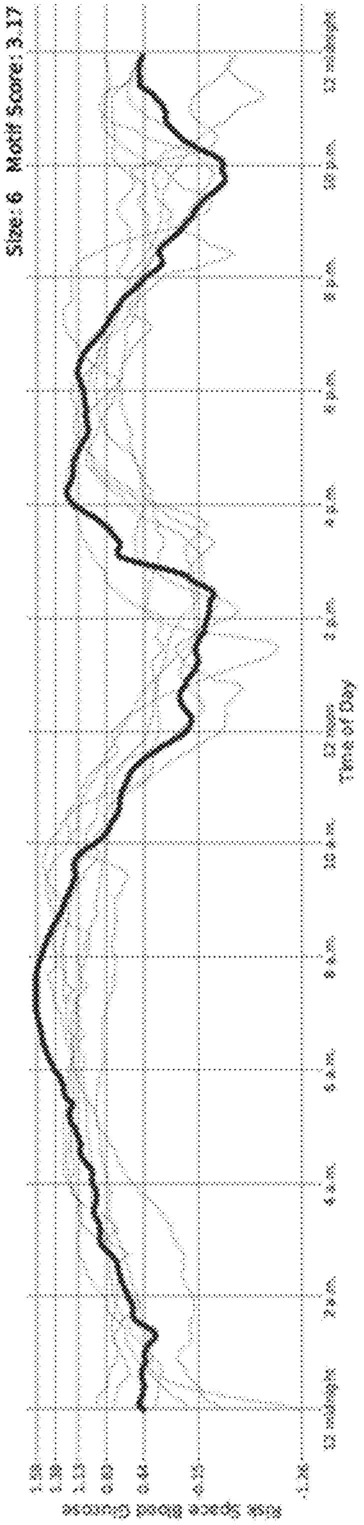
Figure 5D:
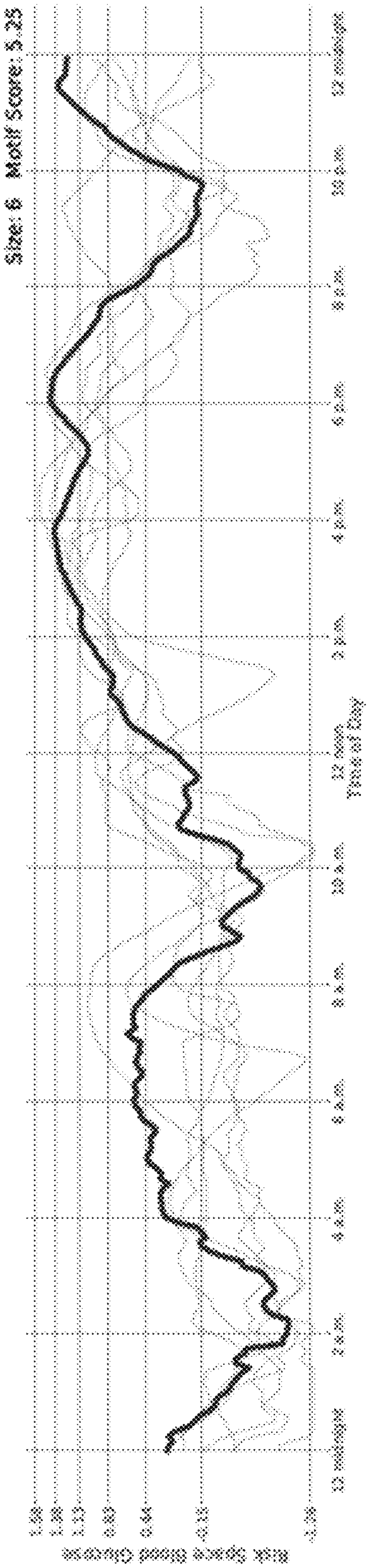

FIGS. 4A, 4B, 4C, and 4D shows composition of the cluster obtained for motif $m \in \Omega_\tau$ when using $\Omega_\tau$ and the classify_profile algorithm to classify daily CGM profiles from the validation data set, wherein τ=0.75 (FIG. 4A), 1.25 (FIG. 4B), 1.75 (FIG. 4C), and 2.25 (FIG. 4D). Note that motif m is the same regardless of τ. FIGS. 4A, 4B, 4C, and 4D show the clusters obtained for the same motif m which is found in $\Omega_T$ for $\tau \in \{0.75, 1.25, 1.75, 2.25\}$, and these plots confirm the observations made above.

FIGS. 5A, 5B, 5C, and 5D show composition of cluster $C_i$ for (from top to bottom) $i \in \{1, 200, 400, 483\}$ obtained by using the single_motif algorithm with τ=1.25, to classify daily CGM profiles from the validation data set. Similar results are obtained when classifying daily CGM profiles from the testing data set.

Due to the definition of the single_motif algorithm, the maximum possible score that will allow inclusion in the first cluster found is less than or equal to the maximum possible score that will allow inclusion in the last cluster found. The effect of this on the composition of each cluster is shown in FIGS. 5A, 5B, 5C, and 5D which show the daily CGM profiles from the validation data set assigned to clusters 1, 200, 300, and 483 (the last cluster) as found when τ=1.25.

Figure 6:
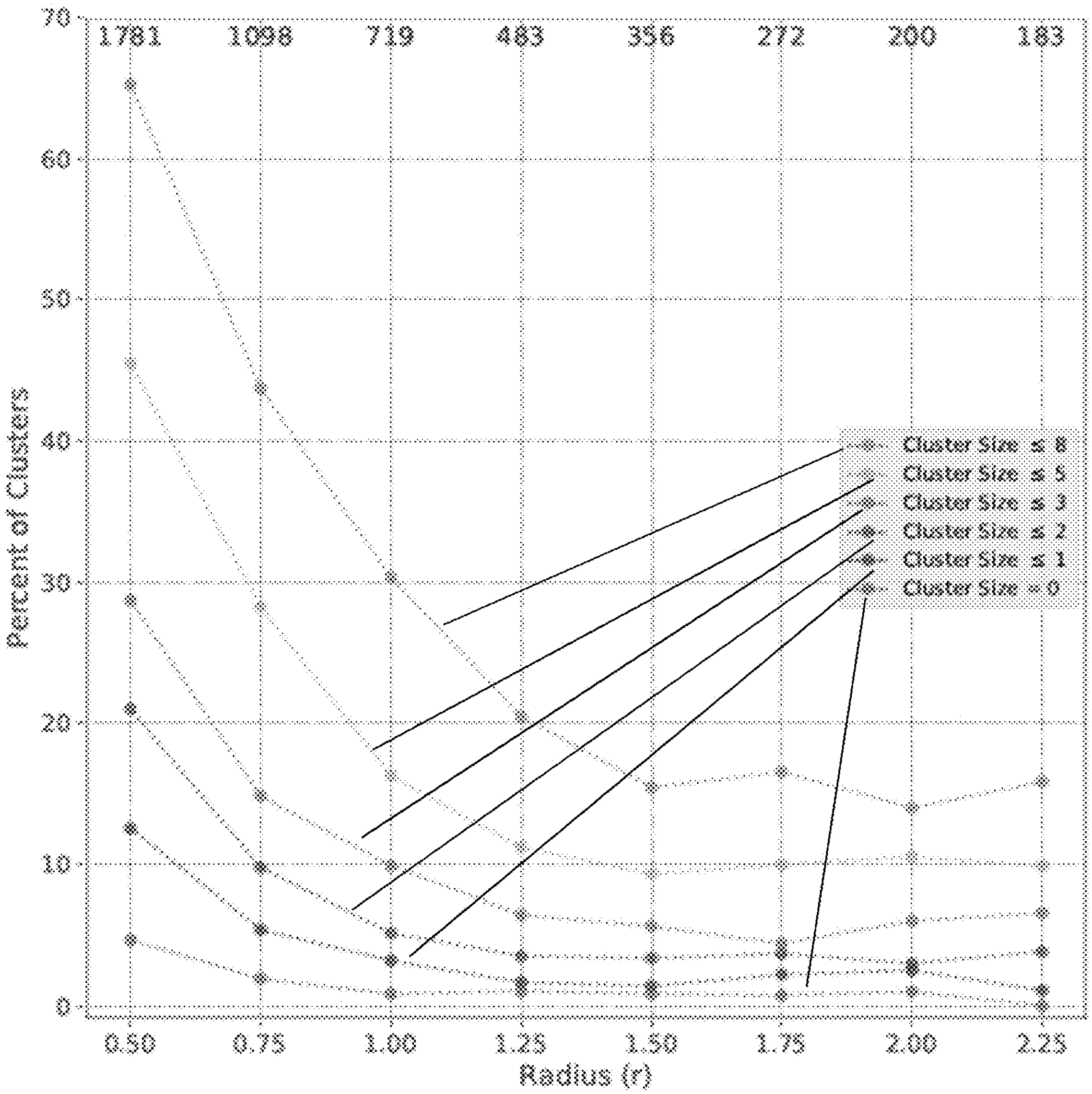
FIG. 6 shows percent of clusters in each clustering of the validation data set where the cluster size is less than or equal to a fixed size p for each of the 8 different tolerance $\tau$ values used.
Figure 7A:
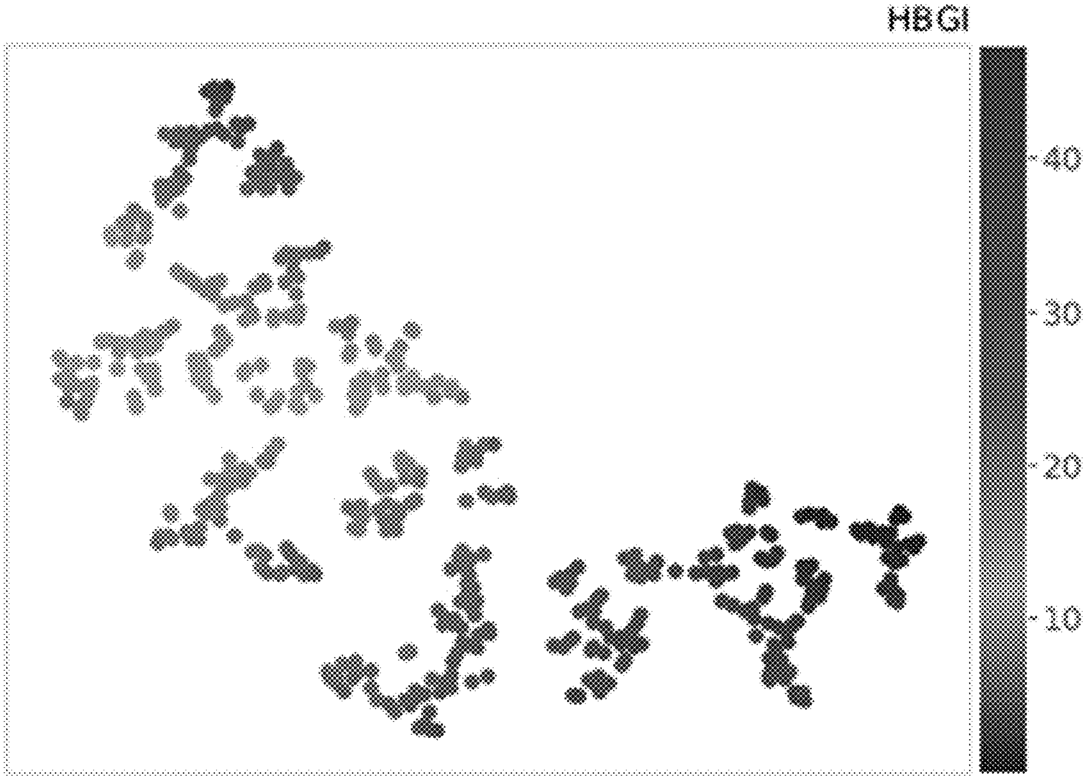
FIGS. 7A, 7B, 7C, 7D, 7E, 7F, 7G, and 7H shows 2-dimensional t-distributed stochastic neighbor embedding (t-SNE) of 483 representative daily profiles (motifs) in $\Omega$ using 8 clinical metrics of the motifs.
Figure 7B:
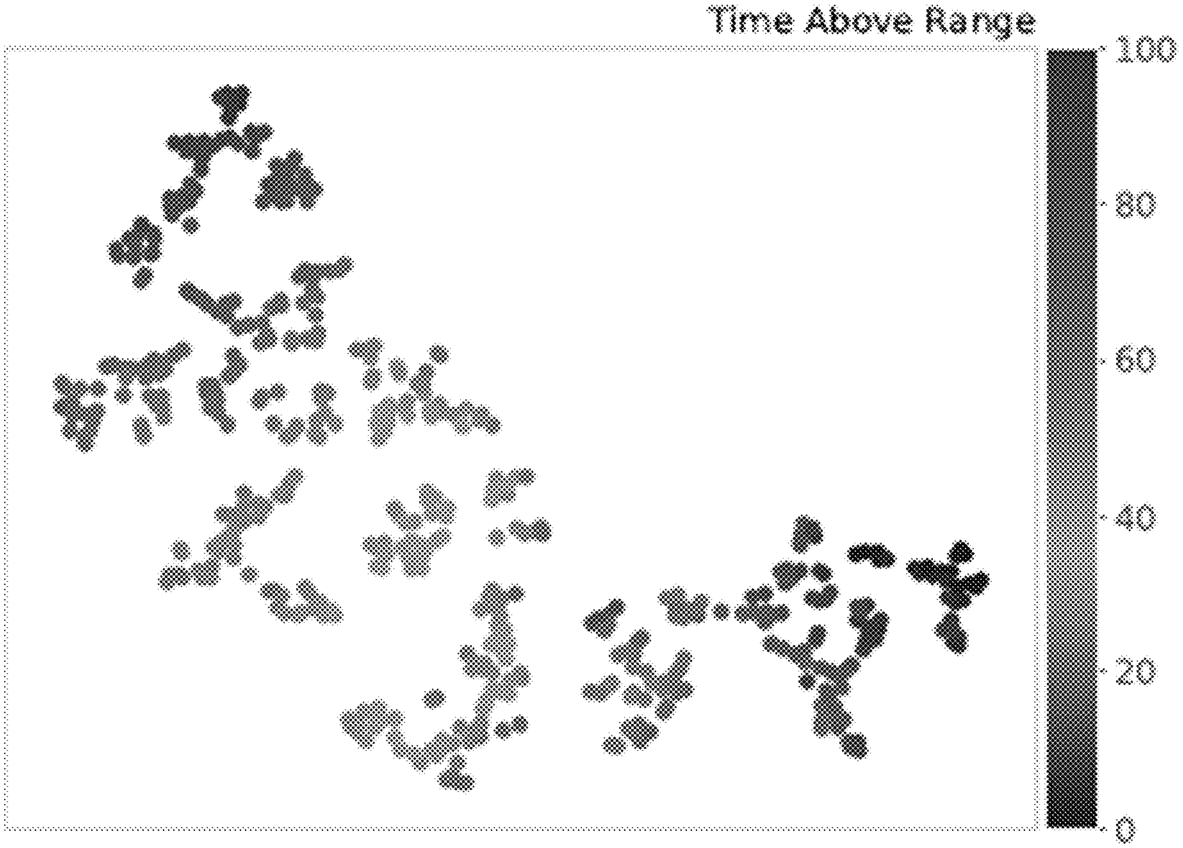
Figure 7C:
Figure 7D:
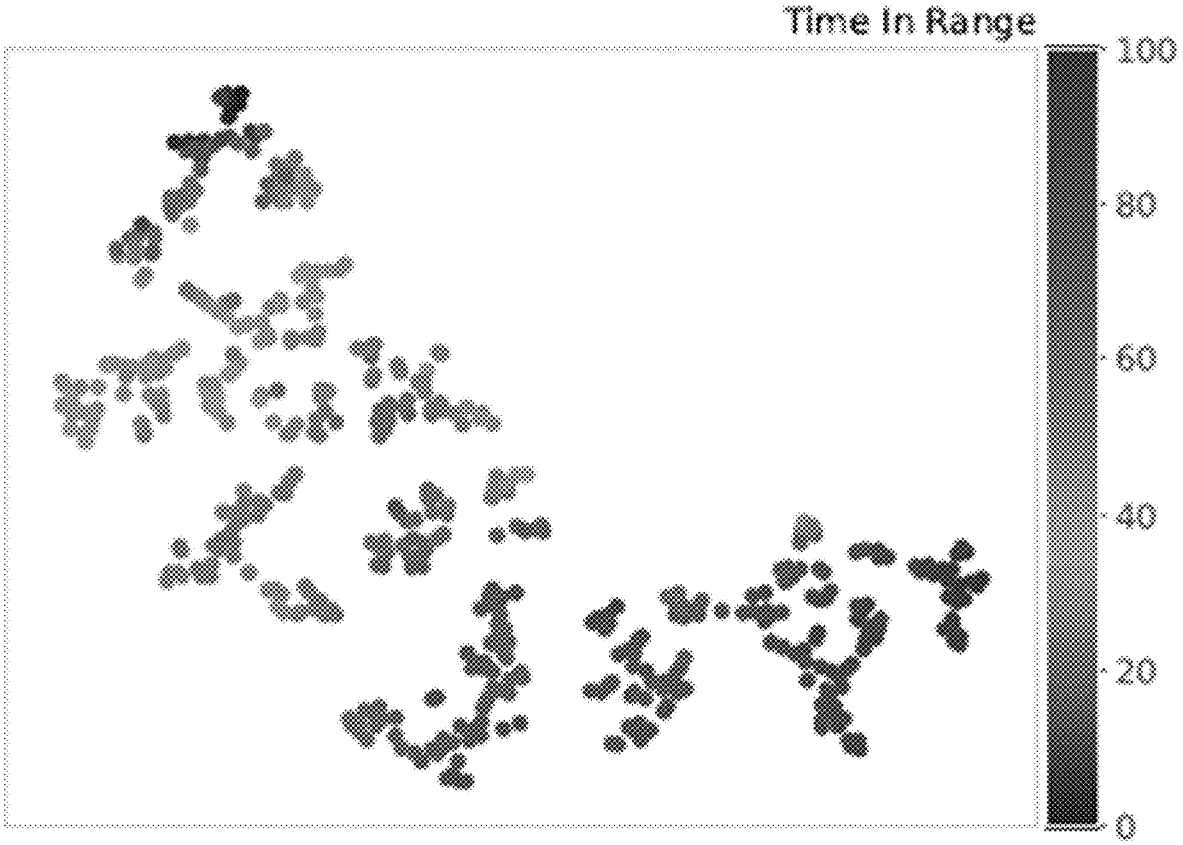
Figure 7E:
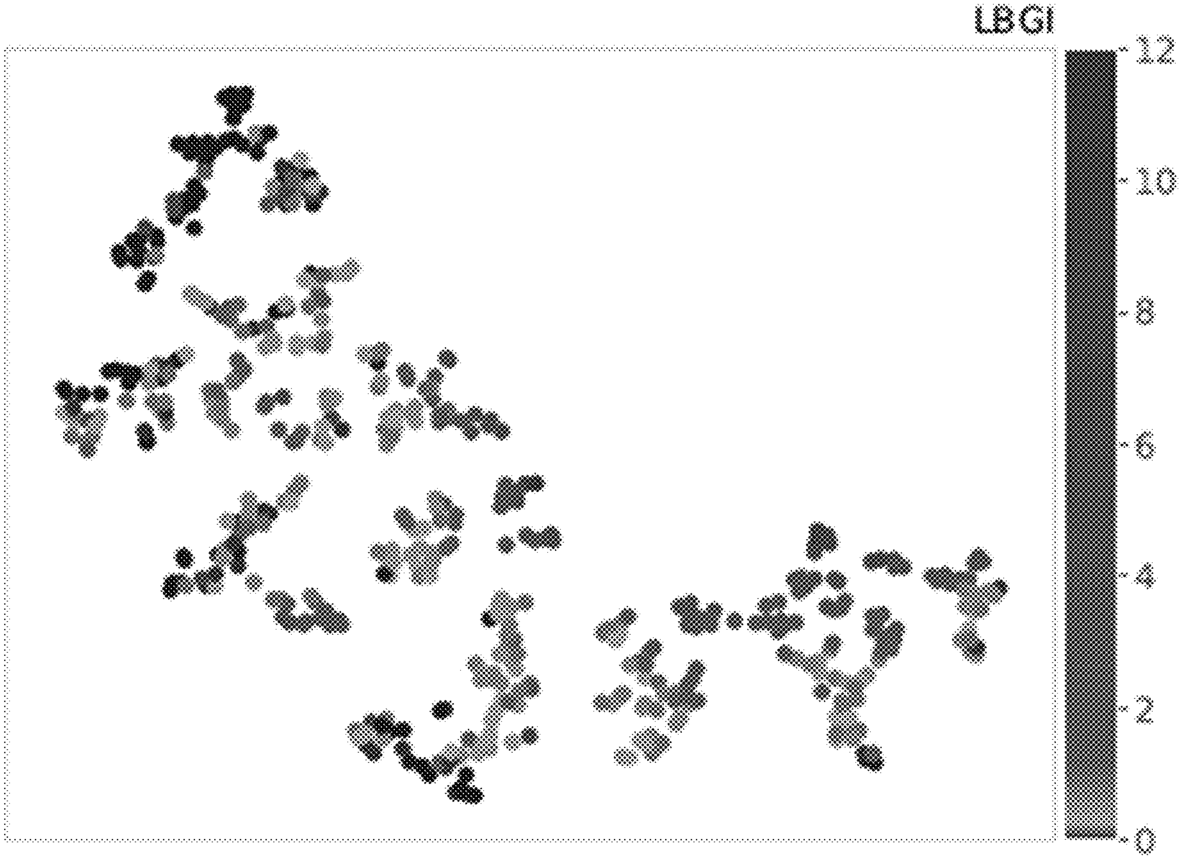
Figure 7F:
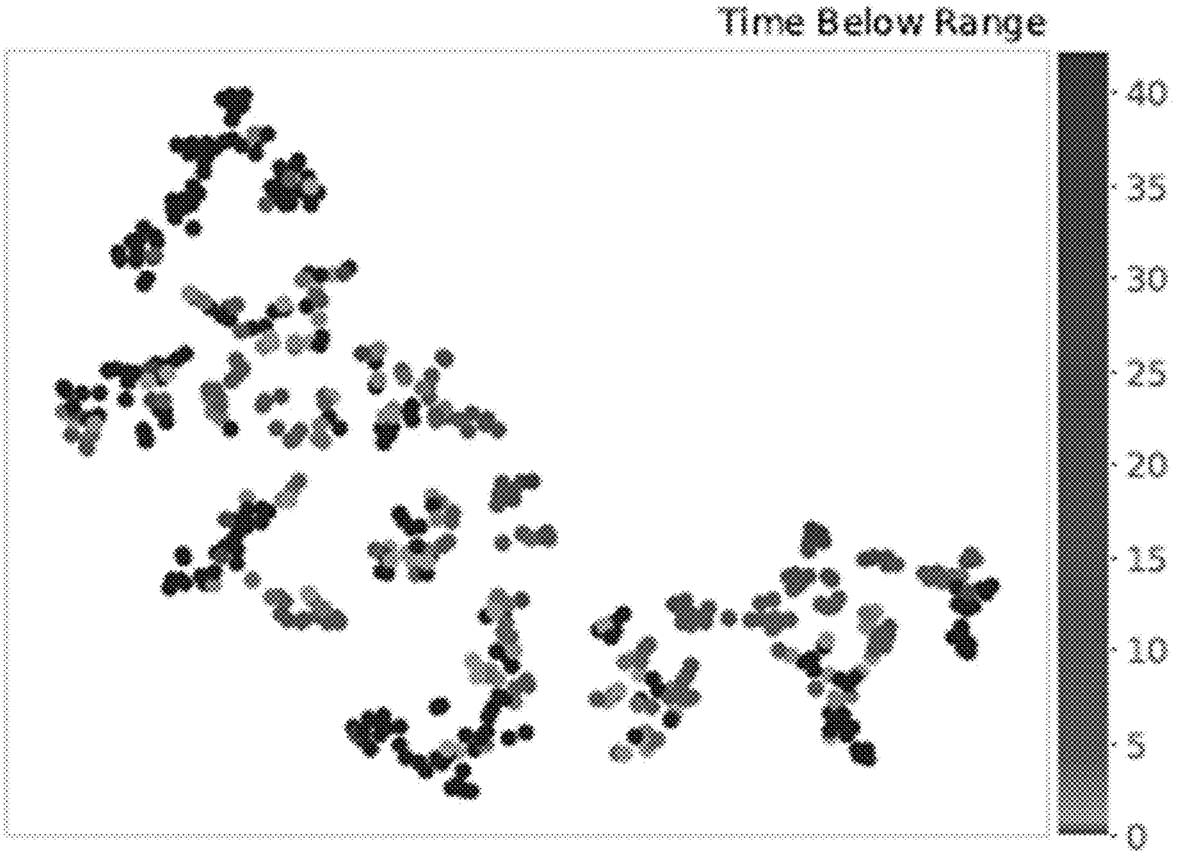
Figure 7G:
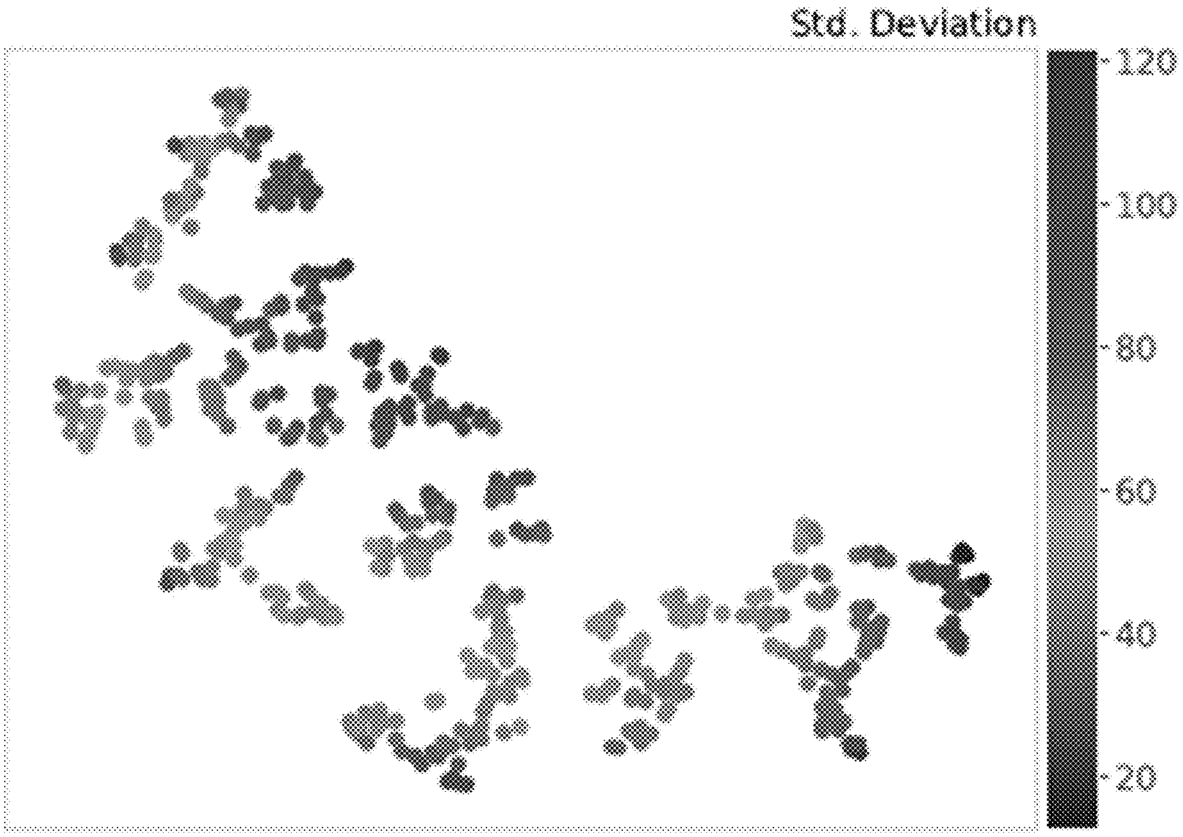
Figure 7H:
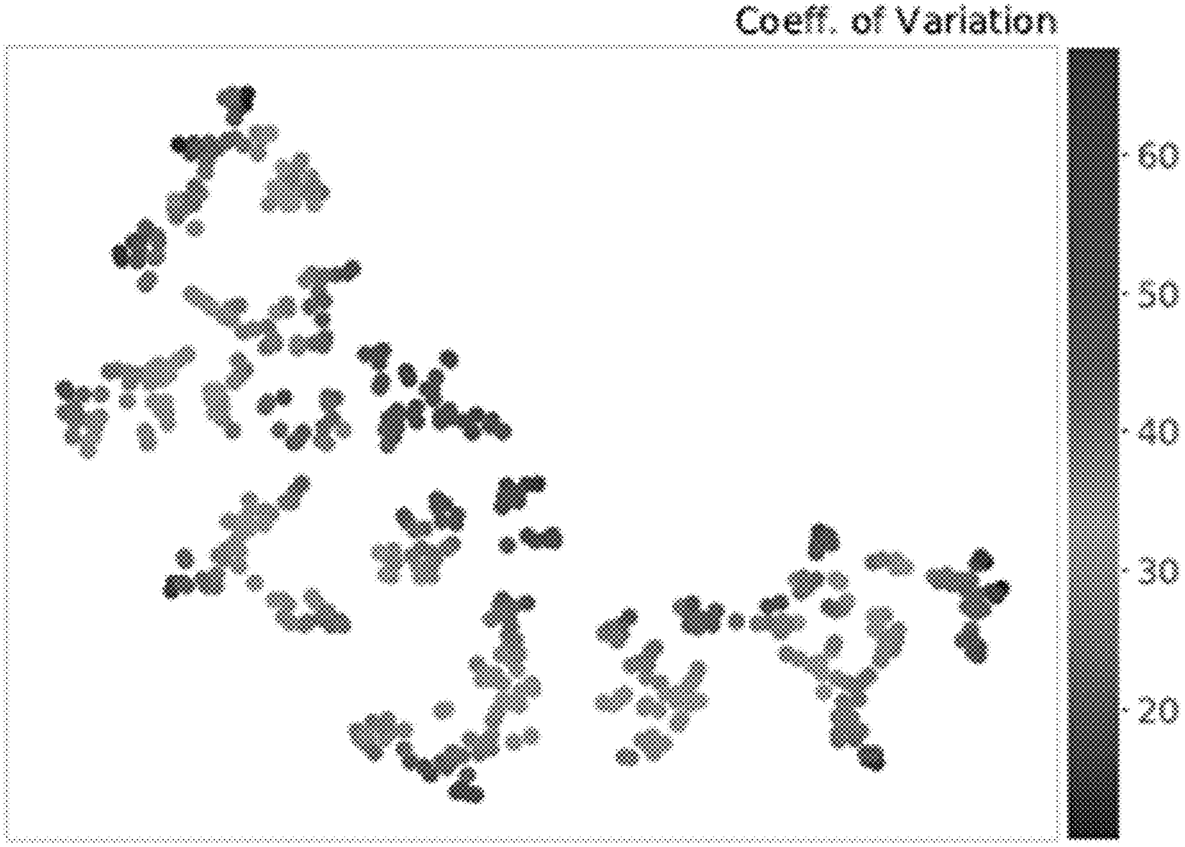

The choice of the tolerance τ is motivated by the main goal of this research: to identify a finite set of representative daily profiles such that almost any daily CGM profile can be matched to one of the representative daily profiles. As mentioned previously, for a given data set, a decrease in the tolerance τ results in an increase in the number of motifs found and therefore clusters in the clustering. FIG. 6 displays, for each of the 8 different tolerance τ values considered, the percent of clusters in each clustering of the validation data set where the cluster size is less than or equal to a fixed size $\rho \in \{0, 1, 2, 3, 5, 8\}$.

FIG. 6 shows percent of clusters in each clustering of the validation data set where the cluster size is less than or equal to a fixed size ρ for each of the 8 different tolerance τ values used The numbers at the top of the plot indicate the number of clusters in the clustering by tolerance. FIG. 6 shows that as the tolerance τ decreases and the number of motifs increases, the percent of clusters with very few (≤5) daily CGM profiles assigned to them is quite stable until tolerance τ=1.25, at which point the percent of clusters with very few (≤5) daily CGM profiles assigned to them increases dramatically. This behavior is indicative of overfitting to the training data set, where many of the motifs are so specific to the training data set that they are unlikely to match to daily CGM profiles in other (as yet unseen) data sets. Diversity of motifs is encouraged, but motifs that are so specific to the training data set and will not generalize are to be avoided, and this informs the choice of τ=1.25 which is the tolerance value which results in the most diverse set of motifs which are not overfit to the training data set.

Thus, the set of representative daily profiles, Ω, is defined as the set of representative daily profiles obtained by using the all_motifs algorithm with τ=1.25 on the daily CGM profiles in the training data set. Therefore $\Omega=\Omega_{1.25}$, $|\Omega|=\Omega_{1.25}|=$483.

Robustness of Ω

If Ω is truly robust, it should be able to classify almost any daily CGM profile presented to it, regardless of the patient who generated the profile—they could be a T1D or T2D patient, they could be using a pump or not, etc. The robustness of Ω is established by using Ω and the classify_profile algorithm to classify each of the 42,595 daily CGM profiles in the testing data set. Using the classification procedure outlined above, 42,165 daily CGM profiles (99.0%) are successfully classified, while just 430 daily CGM profiles (1.0%) remained unclassified. This result is in line with the results obtained on the validation data set where 0.9% of the validation data set daily CGM profiles are unclassified (see Table III).

When the blood glucose value lies outside of the range of the sensor (40 mg/dL to 400 mg/dL), the sensor will report a placeholder value indicating this. A value of 39 mg/dL is reported if the blood glucose value is below the sensor range while a value of 401 mg/dL is reported if the blood glucose value is above the sensor range. An analysis of the daily CGM profiles left unclassified revealed that the average percentage of CGM sensor readings equal to 39 or 401 in unclassified daily CGM profiles is substantially larger than the average percentage of CGM sensor readings equal to 39 or 401 in classified daily CGM profiles. In particular, in the testing data set the average percentage of CGM sensor readings equal to either 39 or 401 is 0.5% for classified daily CGM profiles and 7.2% for unclassified daily CGM profiles. For the 483 motifs in Ω the average percentage of CGM sensor readings equal to either 39 or 401 is 0.3%. Given the striking differences in the average percentage of CGM sensor readings equal to either 39 or 401 between the 483 motifs and the unclassified daily CGM profiles, it is not particularly surprising that these daily CGM profiles are not classified using Ω.

The following eight metrics are calculated for each motif in Ω

1) The mean blood glucose (BG) value,
2) The Time in Range (TIR, the percentage of 5-minute intervals over the 24-hour period in which the blood glucose value is greater than or equal to 70 mg/dL but less than on equal to 180 mg/dL),
3) The Time Above Range (TAR, the percentage of 5-minute intervals over the 24-hour period in which the blood glucose value is strictly greater than 180 mg/dL),
4) The Time Below Range (TBR, the percentage of 5-minute intervals over the 24-hour period in which the blood glucose value is strictly less than 70 mg/dL),
5) The Low Blood Glucose Index (LBGI, a measure of the risk of hypoglycemia where a higher value indicates greater and more frequent hypoglycemic excursions),
6) The High Blood Glucose Index (HBGI, a measure of the risk of hyperglycemia where a higher value indicates greater and more frequent hyperglycemic excursions),
7) The standard deviation (SD) of the BG value, and
8) The coefficient of variation (CV) of the BG value.

FIGS. 7A, 7B, 7C, 7D, 7E, 7F, 7G, and 7H shows 2-dimensional t-distributed stochastic neighbor embedding (t-SNE) of 483 representative daily profiles (motifs) in Ω using 8 clinical metrics of the motifs. Each t-SNE plot is color-coded using clinical metric value of the motif represented by the embedded point. The metrics are then used as input to the sklearn.manifold.TSNE function of Scikit-learn to generate a 2-dimensional t-distributed stochastic neighbor embedding (t-SNE) plot. These figures display the t-distributed stochastic neighbor embedding with the value of the clinical metric for a given motif encoded by the color of the point which represents the motif in the embedding. There is definite group structure which emerges from this plot: points representing motifs with similar clinical characteristics are embedded more closely to each other than points representing motifs with disparate clinical characteristics. From these figures it is evident that the orange group corresponds to motifs which have high HBGI, TAR, and mean BG values, and low TIR, LBGI, TBR, and CV values. However, the SD values of the motifs are not consistent across the orange group.

Figure 8:
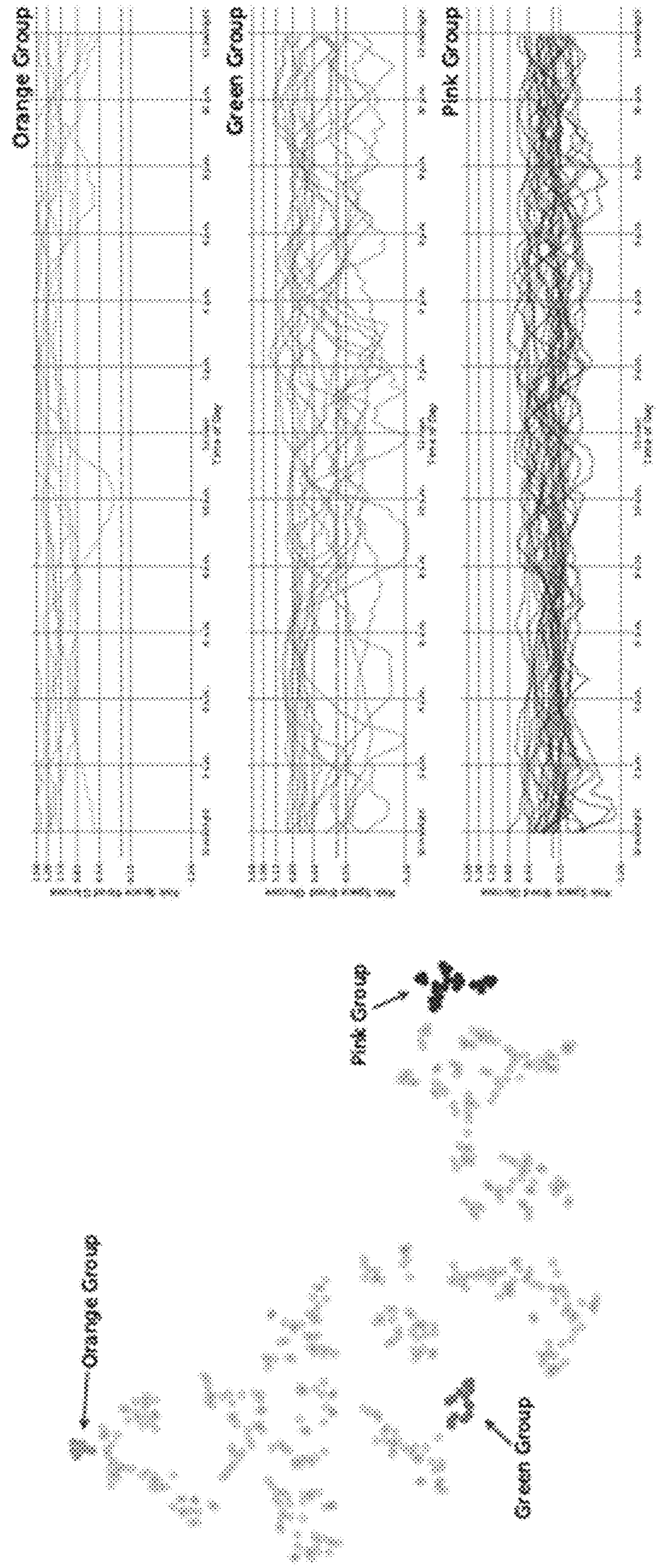
FIG. 8 is an illustration of 3 groups of motifs which are located in close proximity in the t-distributed stochastic neighbor embedding, wherein the motifs in each group are similar in both shape and location in risk space, while the motifs in different groups differ in shape, location in risk space, or both.

All of the above observations are also evident in FIG. 8 in the plot of the motifs corresponding to the orange group. Similar types of observations can be made about the green and pink groups in FIG. 8. FIG. 8 is an illustration of 3 groups of motifs which are located in close proximity in the t-distributed stochastic neighbor embedding. The motifs in each group are similar in both shape and location in risk space, while the motifs in different groups differ in shape, location in risk space, or both. This is especially apparent in FIG. 8 which highlights three different groups of points on the embedding and plots the motifs corresponding to each group of points highlighted on the embedding. Finally, while all the motifs in a given group are similar in shape and location in risk space, while the shape of the motifs in the pink and orange groups are similar, their location in risk space is very different. Similar kinds of observations hold when comparing the three groups of motifs.

Sub-Types of Diabetes

The distribution of daily CGM profiles in a given data set to clusters defined by the motifs in Ω differs based on the sub-type of diabetes of the patients who generated the daily CGM profiles. This sensitivity can be seen in FIG. 9 which compares the composition of clusters formed by daily CGM profiles generated by T1D patients in the testing data set with the composition of clusters formed by daily CGM profiles generated by T2D patients in the testing data set.

Each bar plots $Pct_{C_i}$, the percent of daily CGM profiles assigned to cluster $C_i$ for all $i \in \{1, \ldots, 483\}$. The top plot shows the distribution of daily CGM profiles generated by T1D patients to the clusters defined by the motifs in Ω, while the bottom plot shows the distribution of daily CGM profiles generated by T2D patients to the clusters defined by the motifs in Ω. There are 37,758 daily CGM profiles generated by T1D patients in the testing data set, with 37,349 (98.9%) classified and 409 (1.1%) unclassified. There are 4,837 daily CGM profiles generated by T2D patients in the testing data set, with 4,816 (99.6%) classified and 21 (0.4%) unclassified. Although it is visually clear that these are two different distributions, a Wilcoxon signed-rank test (via the scipy.stats.wilcoxon function in SciPy) is used to test the hypothesis that the set $\{Pct_{C_i} | i \in \{1, \ldots, 483\}\}$ defined by daily CGM profiles generated by T1D patients and the set $\{Pct_{C_i} | i \in \{1, \ldots, 483\}\}$ defined by daily CGM profiles generated by T2D patients came from the same distribution. The test statistic is 38926 with a p-value $<0.001$, allowing us to reject the null hypothesis and conclude that the two sets came from different distributions, reinforcing that the distribution of daily CGM profiles to clusters defined by the motifs in Ω is sensitive to the sub-type of diabetes of the patients who generated the daily CGM profiles The growing prevalence of CGM has given rise to the need for ways to classify daily CGM profiles so that information contained in the profiles can be leveraged in predictive modeling, decision support, and automated control systems like the artificial pancreas. This paper outlines an effort to find Ω, a finite set of representative daily profiles such that almost any daily CGM profile be matched to one of the profiles in Ω. We do not claim that this set is minimal or optimal—for the applications outlined below, and those we have in mind, optimality is not needed and could be counterproductive because any optimal solution would be associated with additional loss of information.

Figure 9:
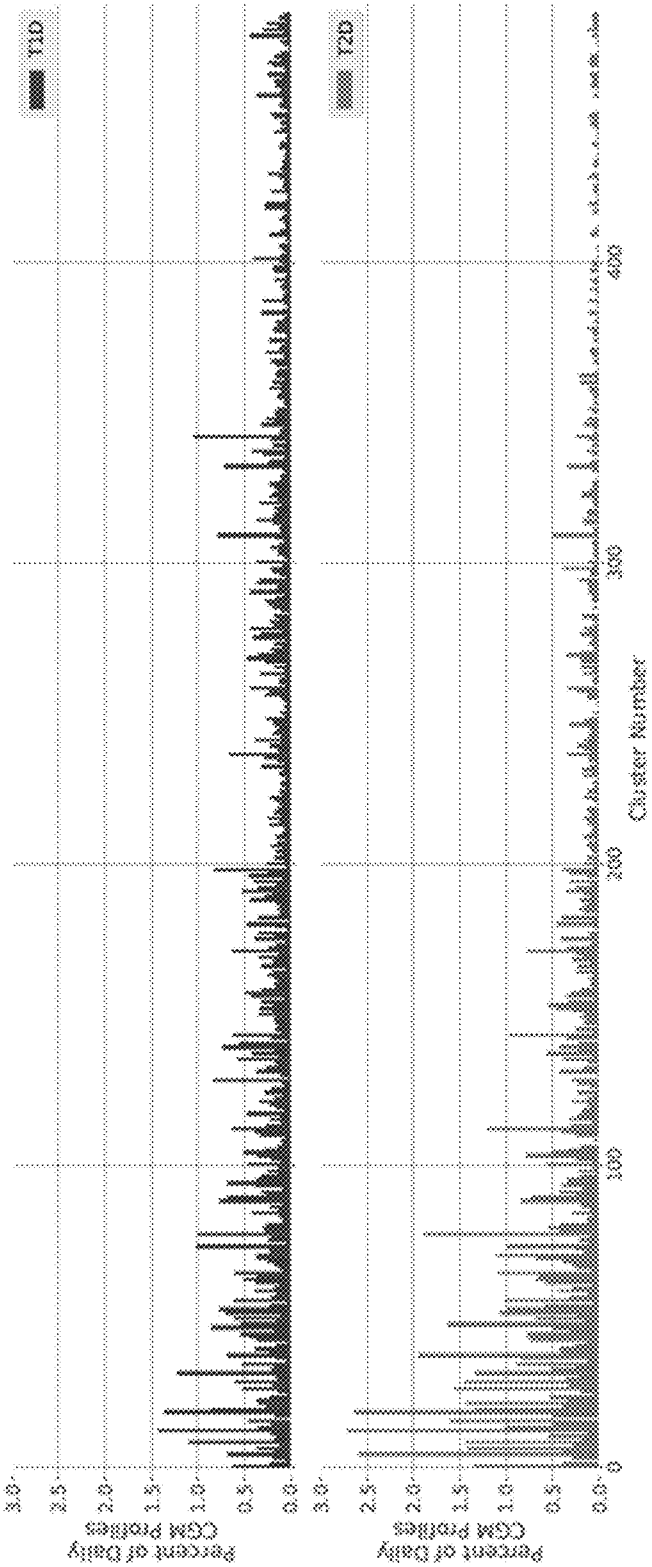
FIG. 9 is a distribution of the daily CGM profiles assigned to each cluster for daily CGM profiles generated by T1D patients (top) and T2D patients (bottom) DIA1 and DIA2 data sets.

FIG. 9 is a distribution of the daily CGM profiles assigned to each cluster for daily CGM profiles generated by T1D patients (top) and T2D patients (bottom) DIA1 and DIA2 data sets. The methods disclosed herein focus on clustering the daily CGM profiles and using the clustering and clusters to identify representative daily profiles (motifs) which belong to Ω. The robustness of Ω is established by using it to successfully classify over 98.8% of 39,916 daily CGM profiles contained in three different data sets. The daily profiles in the three data sets are collected from both T1D and T2D patients using a variety of treatment modes—daily insulin injections, insulin pumps, or artificial pancreas. The experimental results also established that the distribution of matches between the daily CGM profiles in a data set and the motifs in Ω is sensitive to the sub-type of diabetes of the patients who generated the data set of daily CGM profiles which can then be used as input to clinical and automated treatment algorithms.

Given that the above methods enable a daily CGM profile (typically 288 data points) to be reduced to a single integer, say i, which identifies the representative daily profile which best matches the daily CGM profile of interest, examples of applications of this work include:

- Dimensionality reduction: the near infinite multitude of all possible daily CGM profiles are reduced to a finite set
- Compression of daily CGM profiles: the typically 288 data points which define the daily CGM profile are reduced to a single integer i, a huge savings in data storage needs.
- Compression and encryption of daily CGM profiles: instead of transmitting the typical 288 data points in a daily CGM profile a single integer i is all that needs to be transmitted, a huge savings in data transmission needs.

It should be noted that, since a daily CGM profile is being matched to a representative daily profile, there is information loss that occurs, as is typical with data compression. In particular the notion of meals, over and under bolusing of insulin, exercising, and diurnal variations present in a daily CGM profile may not be retained in the motif representation of the daily CGM profile.

Given that just 68.3% of the daily profiles in each of the six data sets satisfied the "As-Is" criteria, over 30% of the daily profiles in the data sets are not even considered for classification, primarily because these daily CGM profiles did not have enough data points for a consistent pattern to be identified. Fortunately, contemporary CGM devices are becoming more reliable and easier to use, continually minimizing the gaps in the data. For example, in a recent database analysis of 1-year use of an AP system (Control-IQ, Tandem Diabetes Care) by over 9,000 users, the system is active and receiving data 95% of the time. A future step in this research is to investigate the possibility of grouping the motifs in Ω such that motifs with the same or very similar clinical interpretations are grouped together. This step would engender clinical meaningfulness to the groups of motifs obtained, and may greatly reduce the state space of a model, decision support tool, or automated control system.

Figure 10:
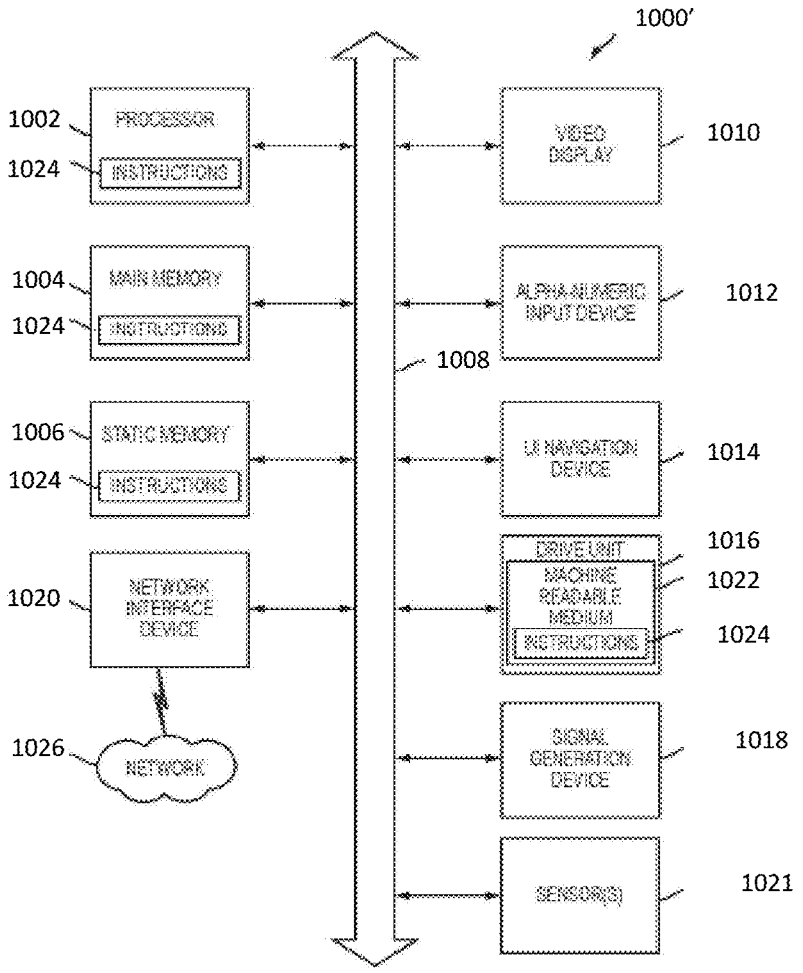
FIG. 10 is a block diagram illustrating an example of a machine upon which one or more aspects of embodiments of the present invention can be implemented.
Figure 11A:
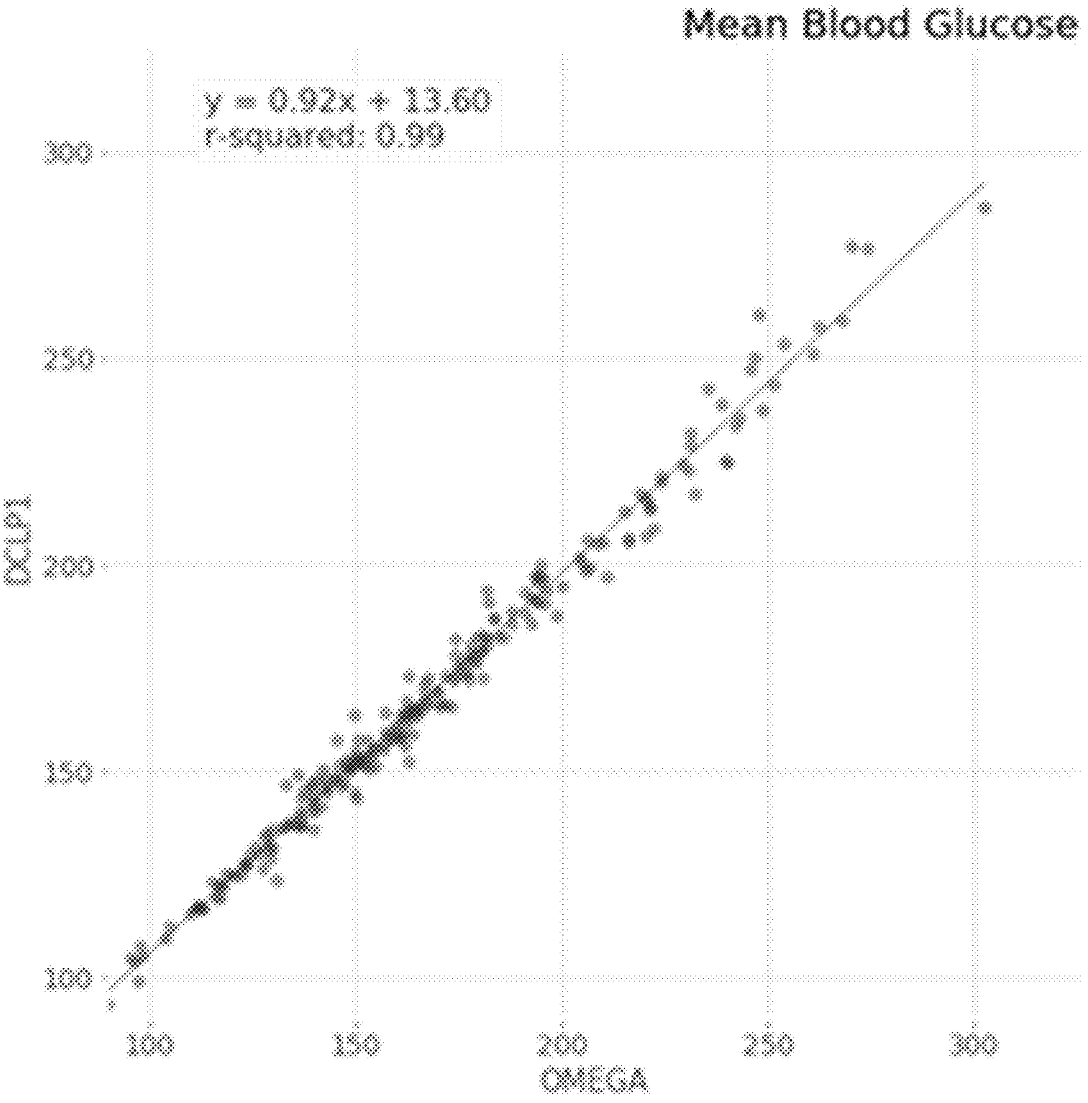
FIGS. 11A, 11B, 11C, 11D, 11E, and 11F show correlation scatter plots for Representative Daily Profiles in $\Omega$ versus the daily CGM profiles in DCLP1, for six clinically relevant metrics.
Figure 11B:
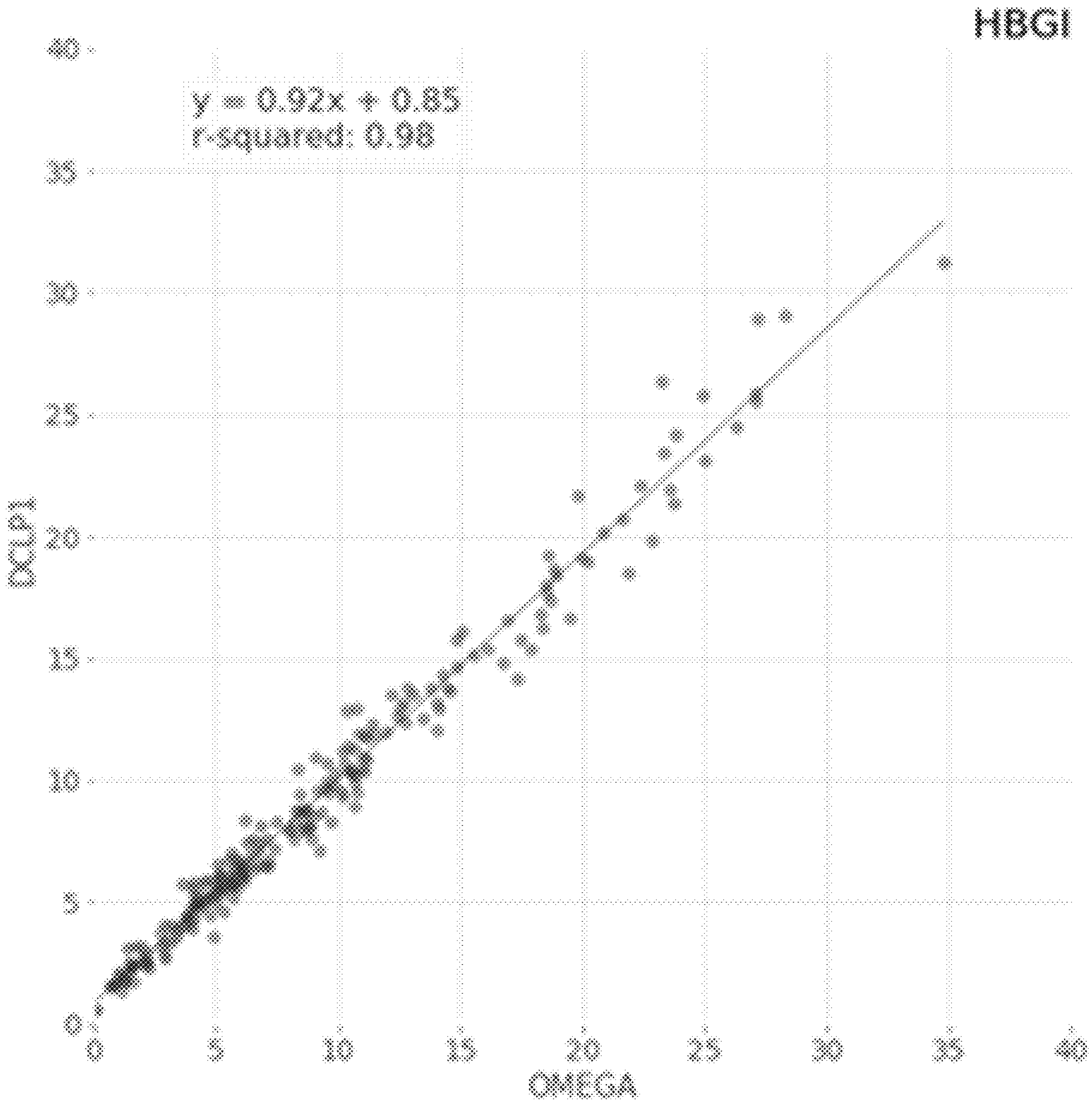
Figure 11C:
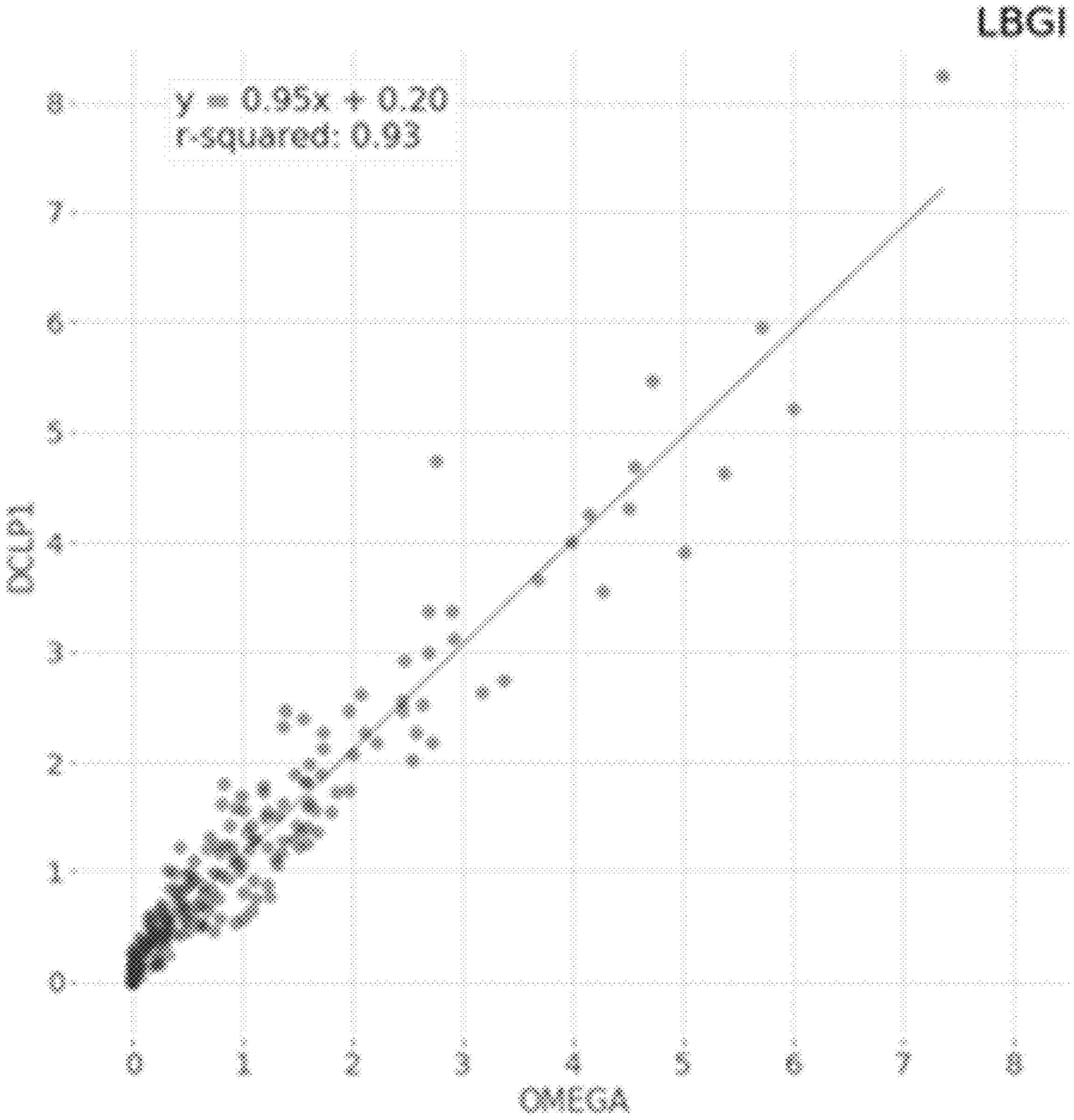
Figure 11D:
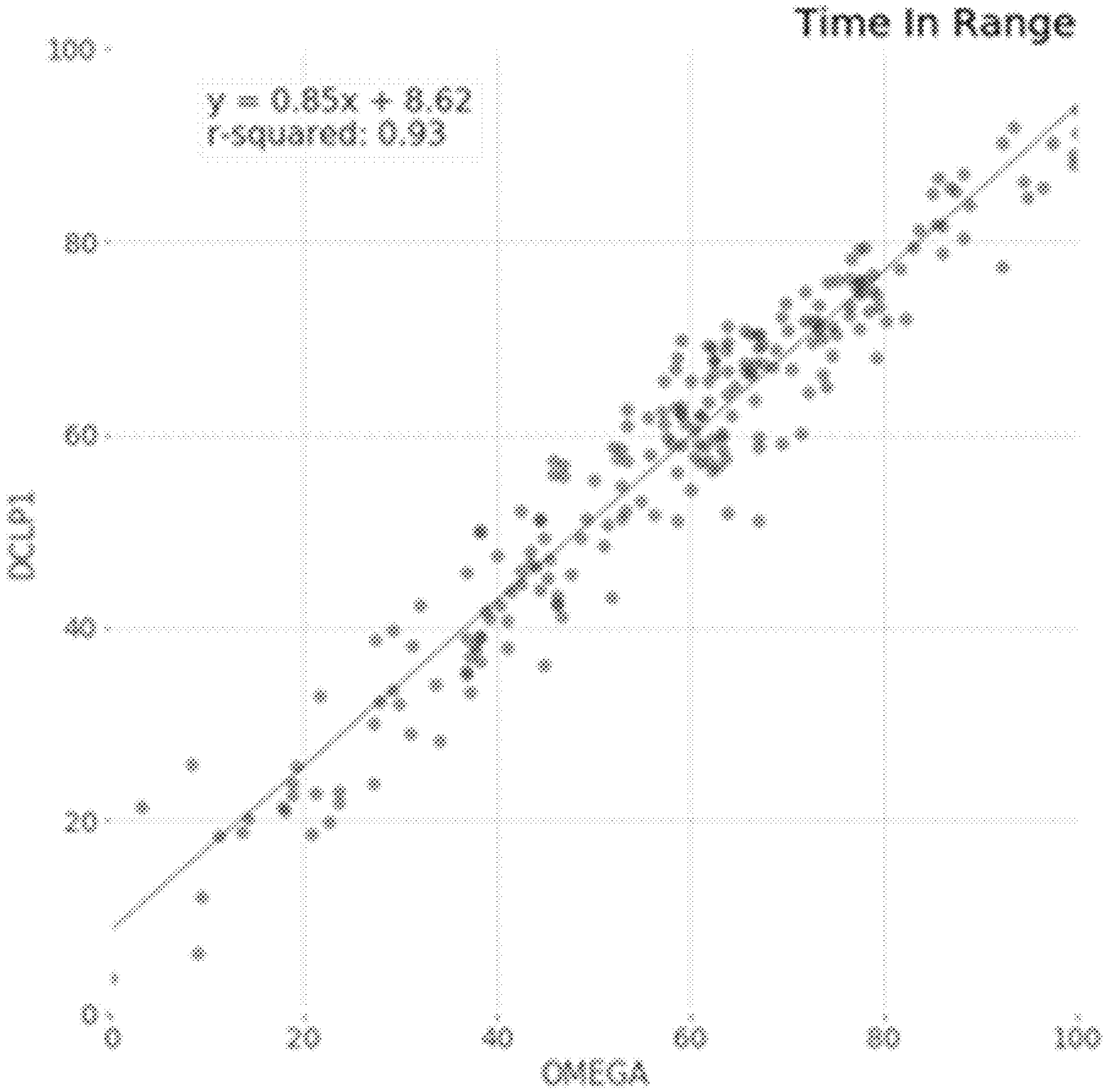
Figure 11E:
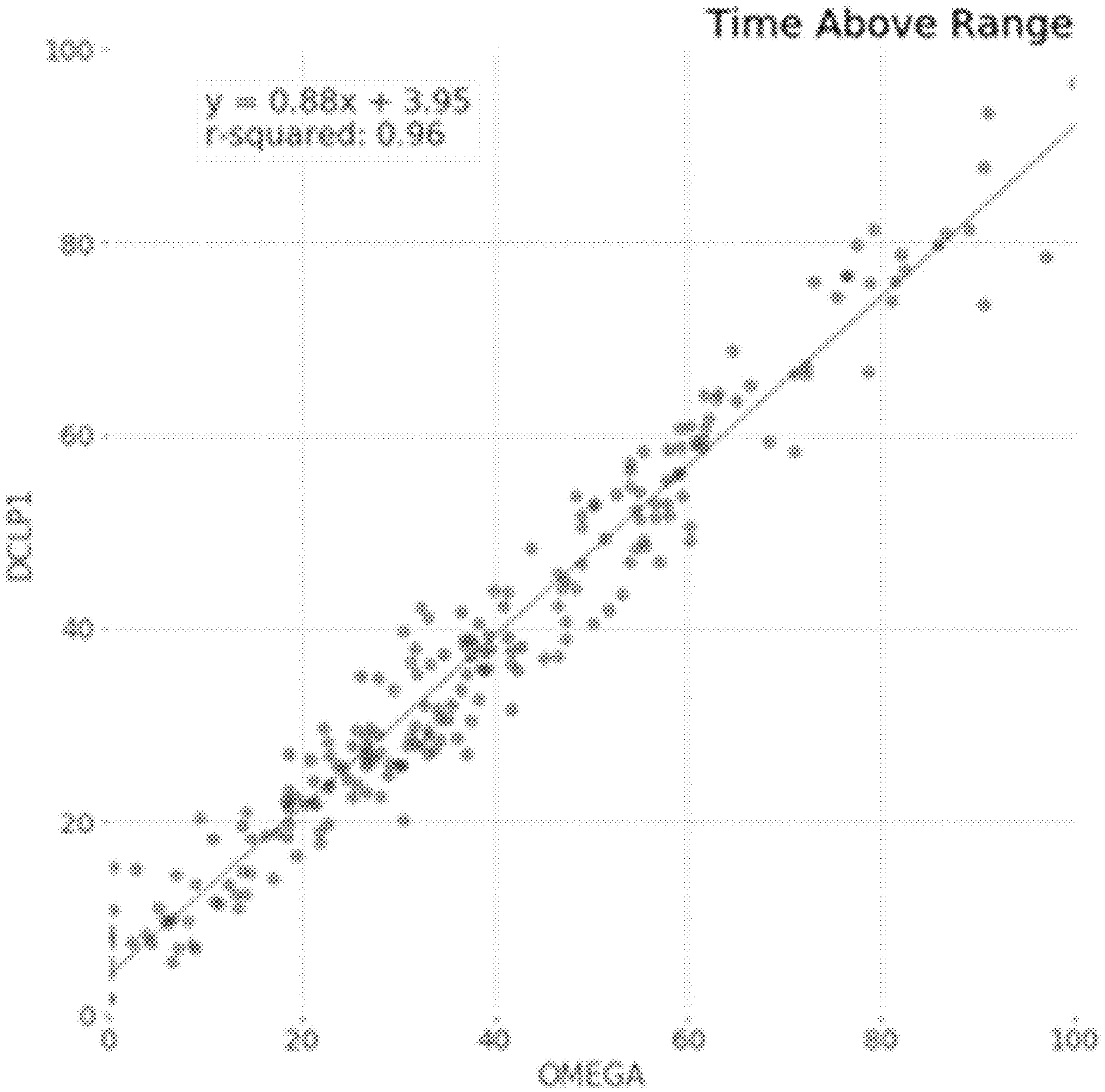
Figure 11F:
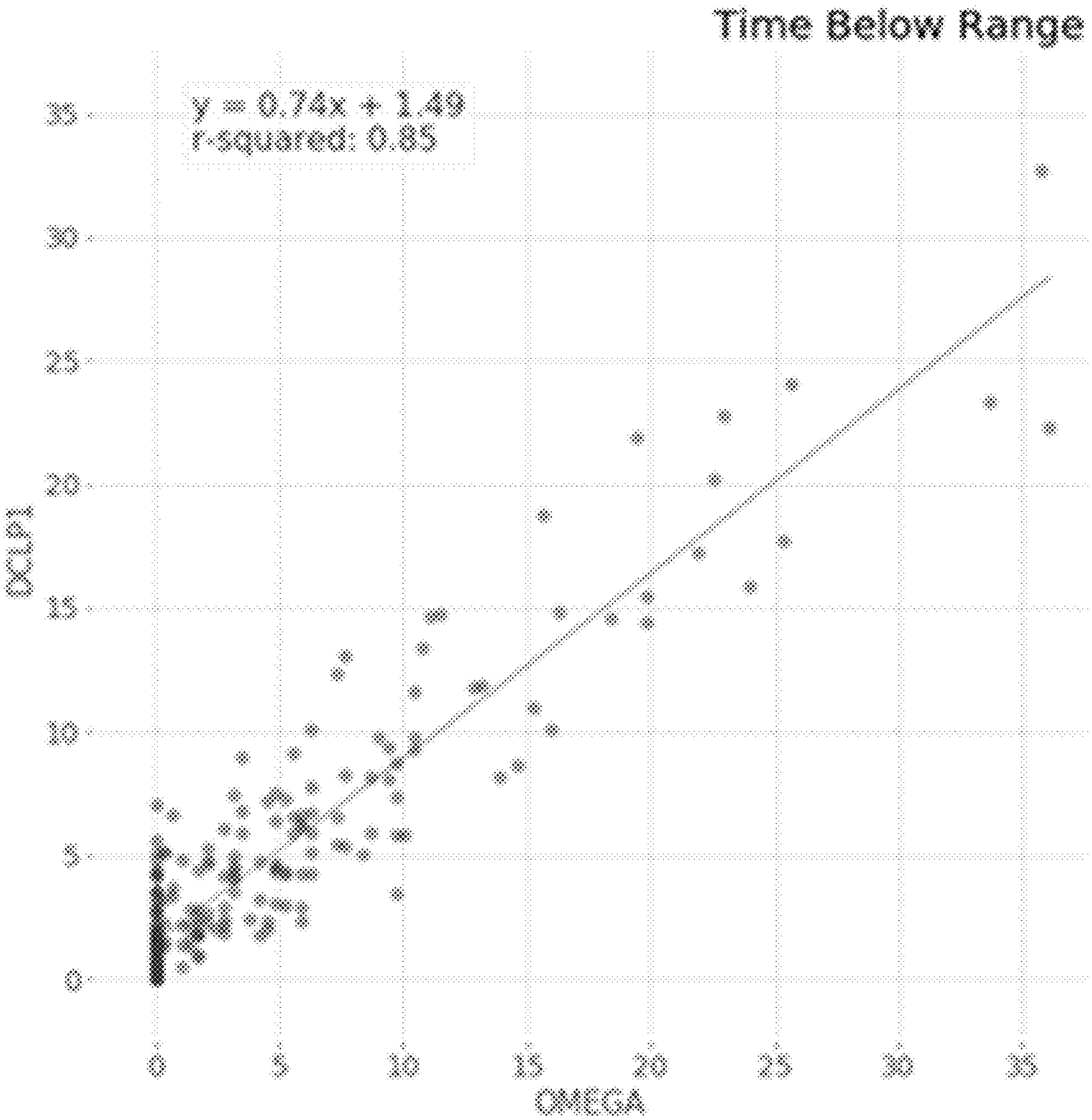
Figure 12A:
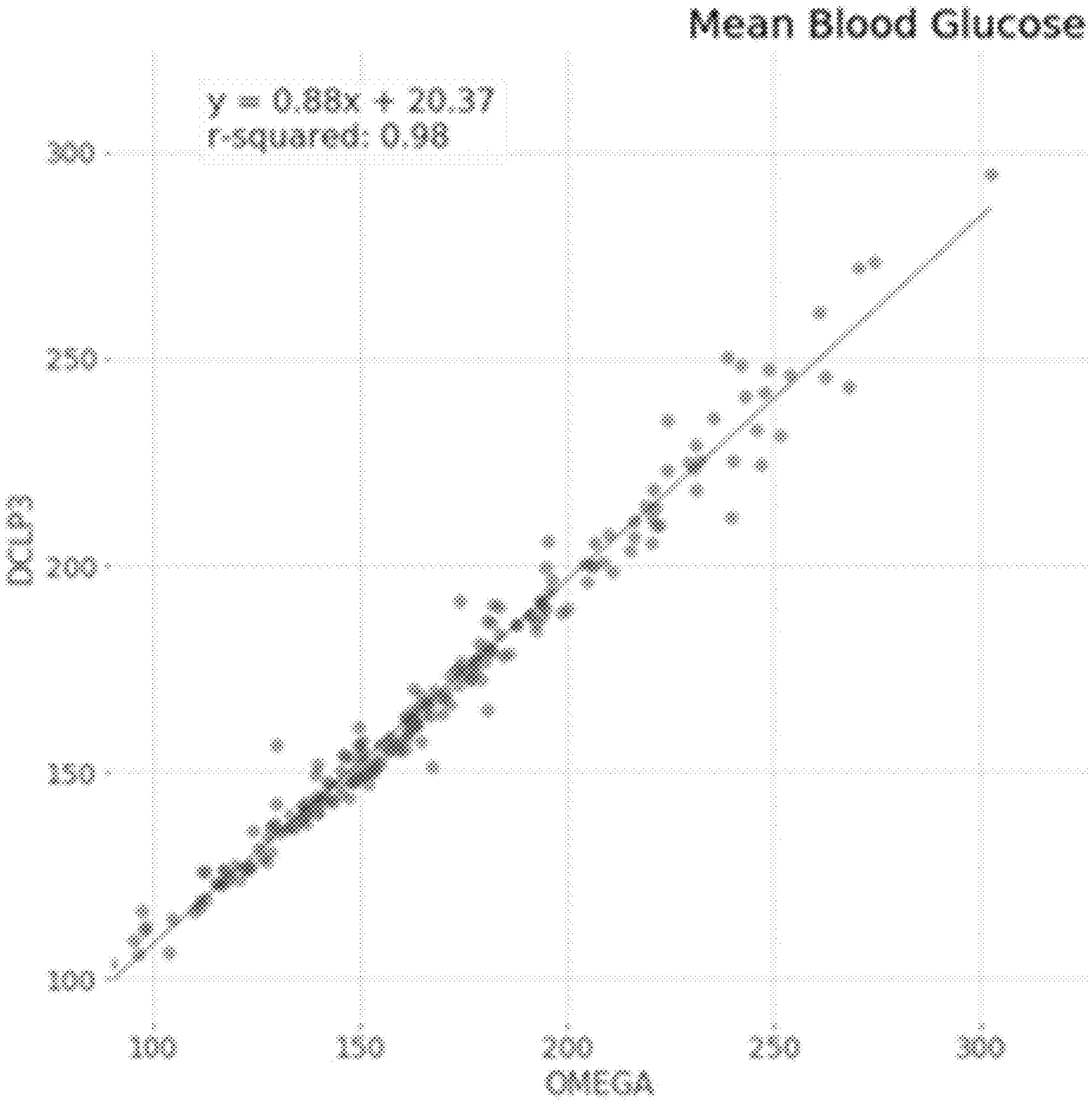
FIGS. 12A, 12B, 12C, 12D, 12E, and 12F show correlation scatter plots for Representative Daily Profiles in $\Omega$ versus the daily CGM profiles in DCLP3, for six clinically relevant metrics.
Figure 12B:
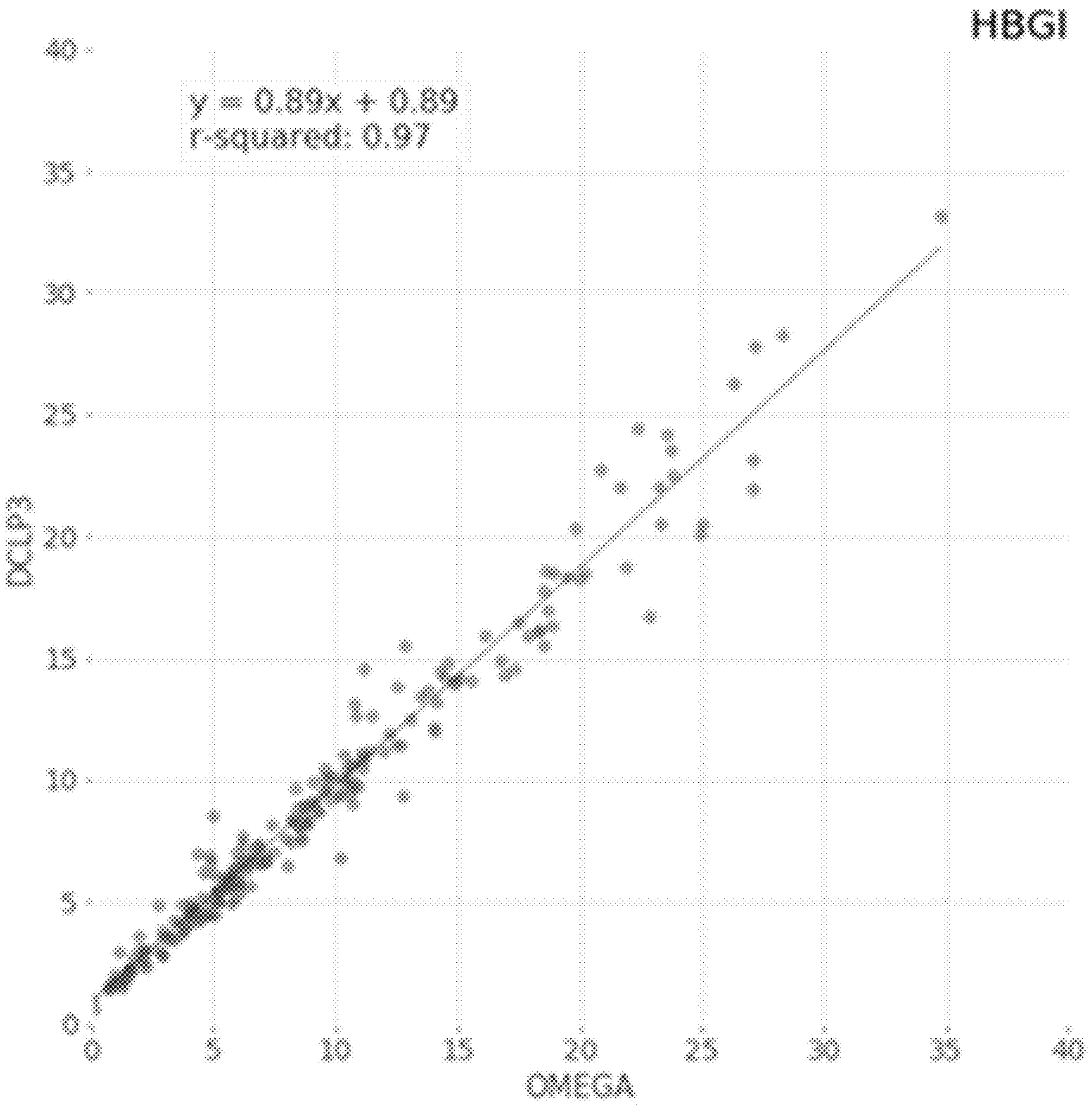
Figure 12C:
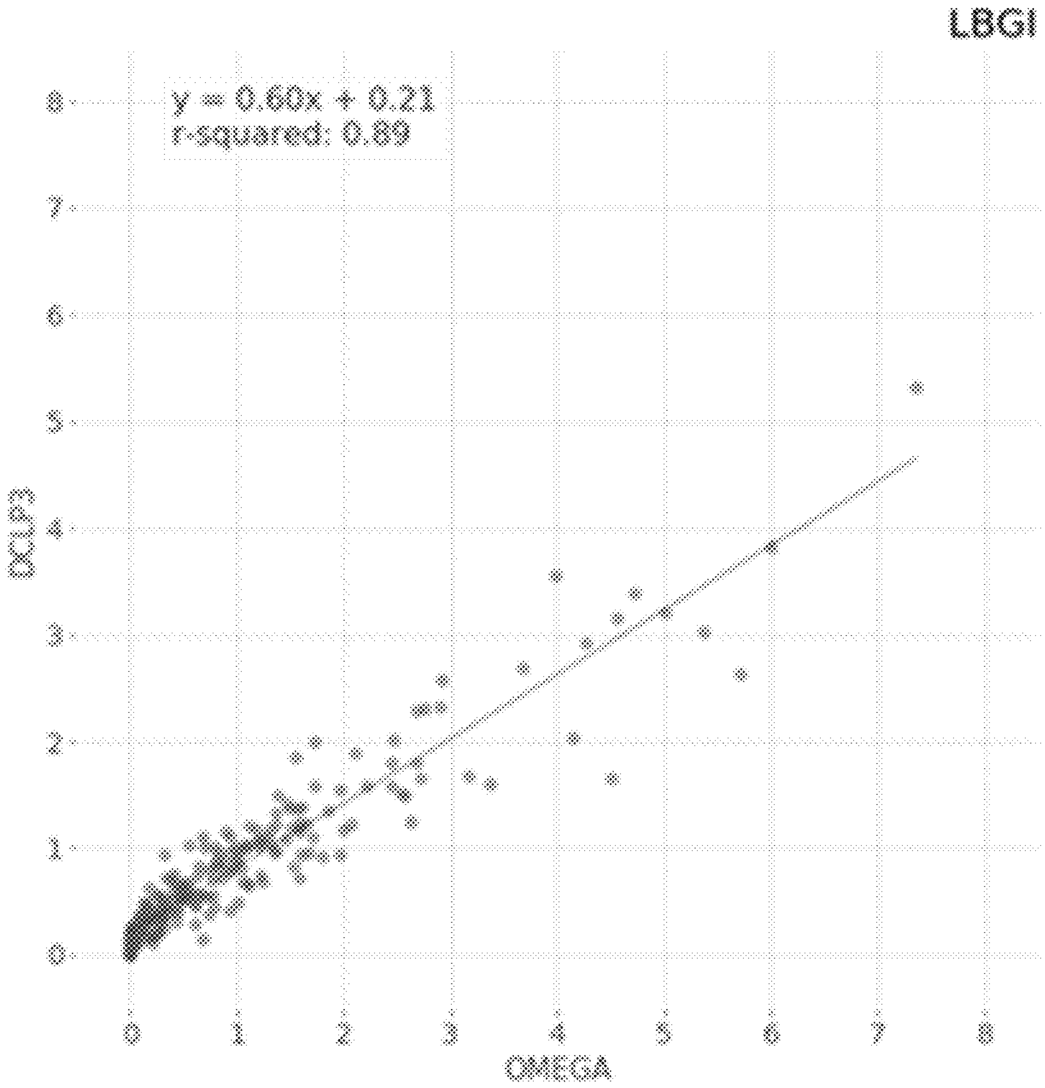
Figure 12D:
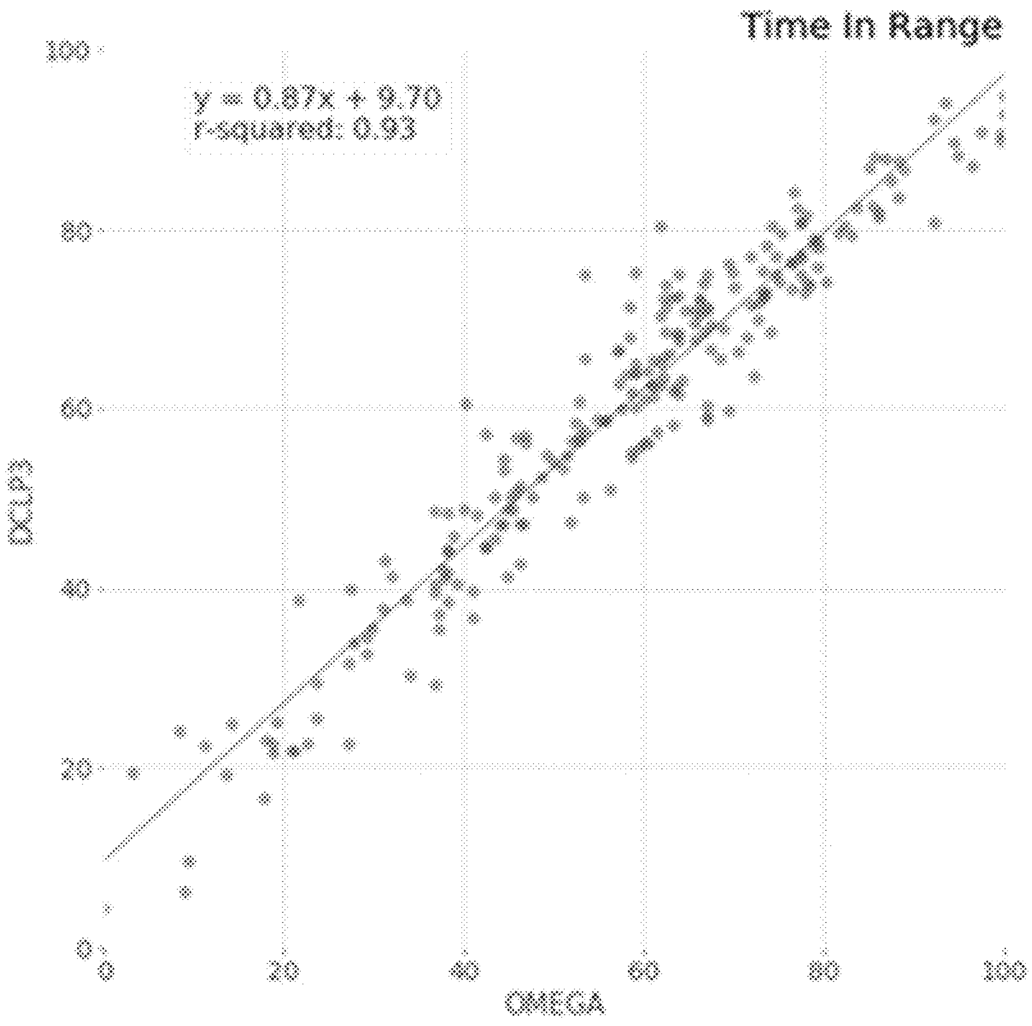
Figure 12E:
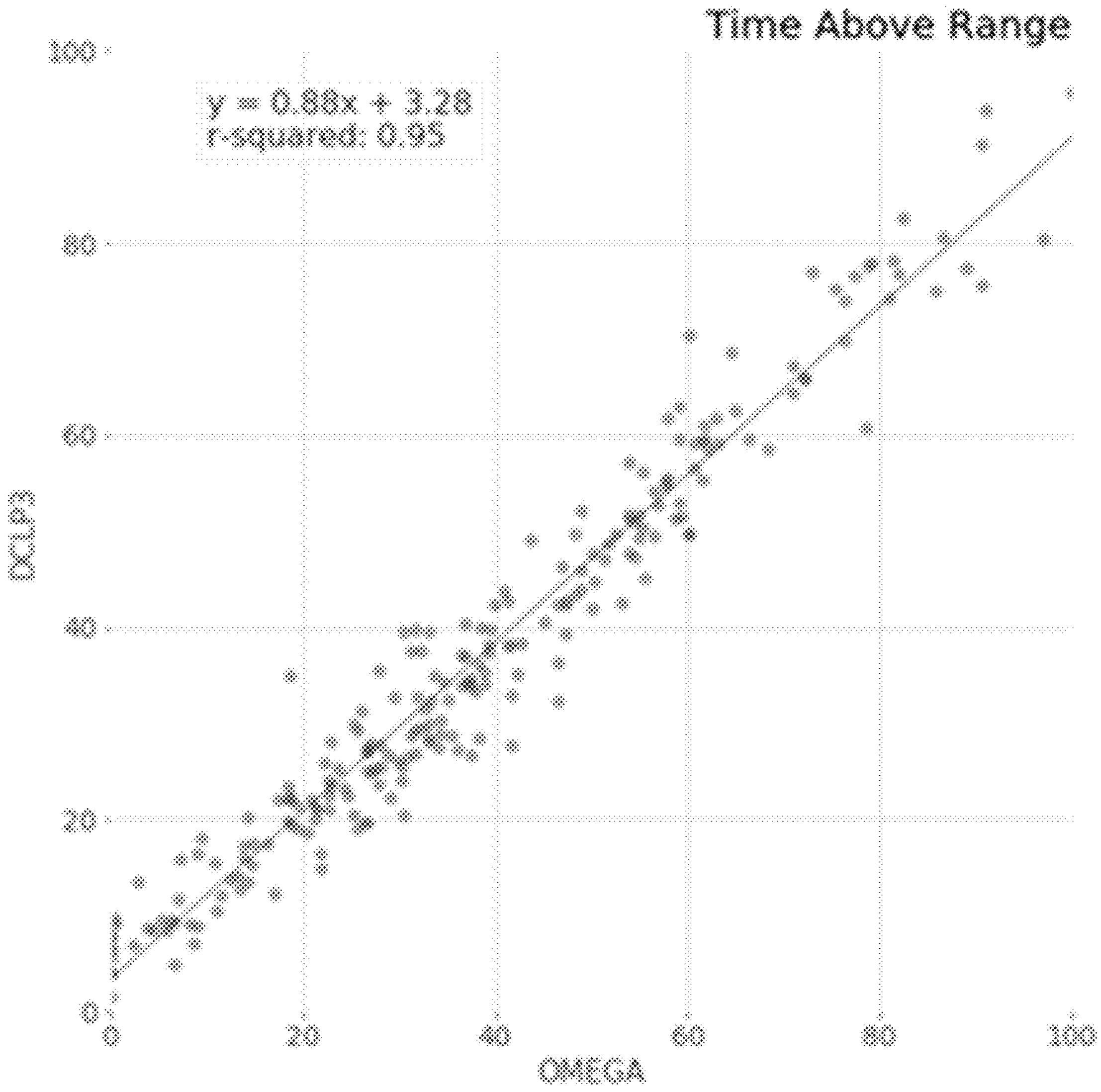
Figure 12F:
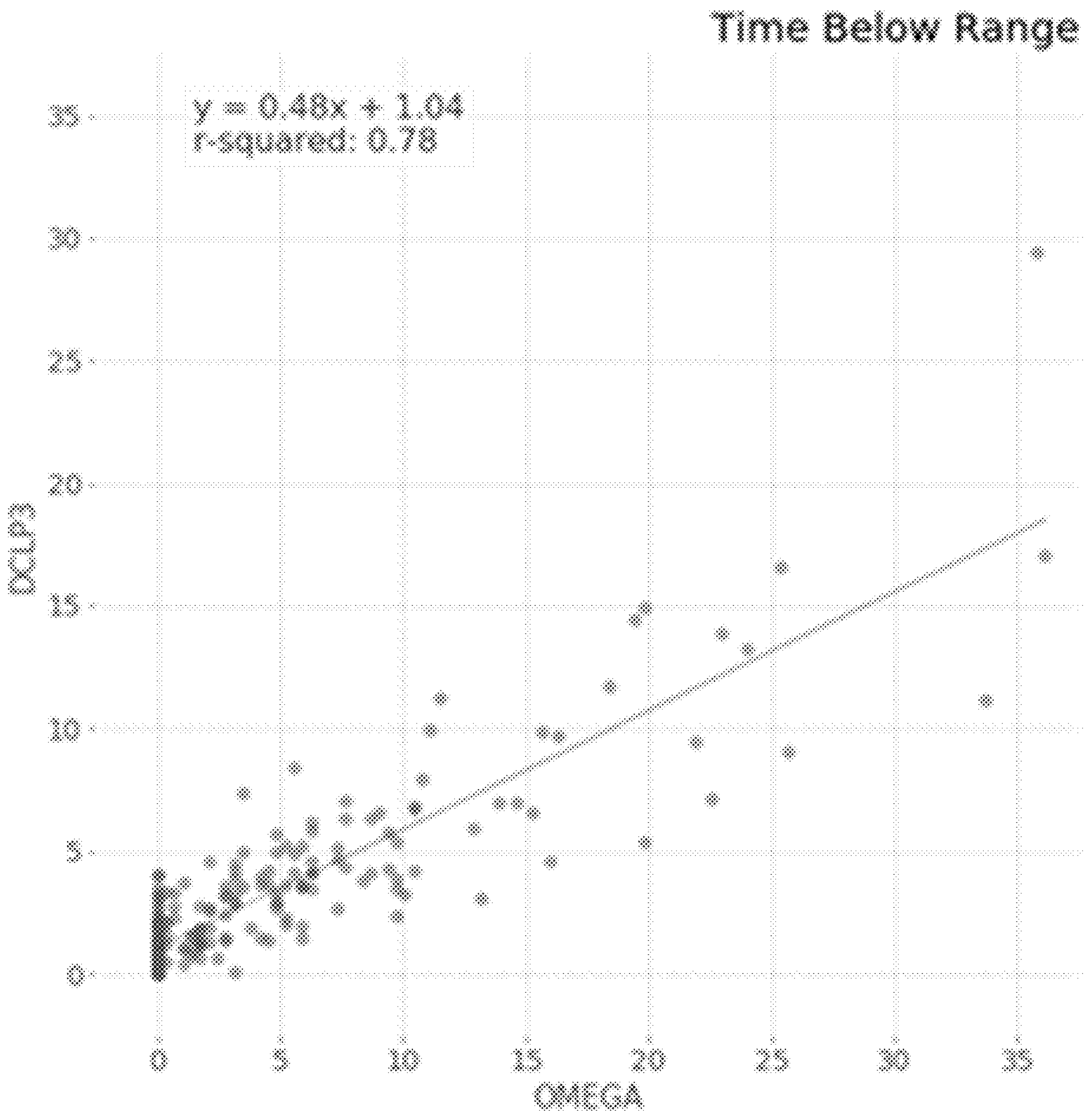
Figure 13A:
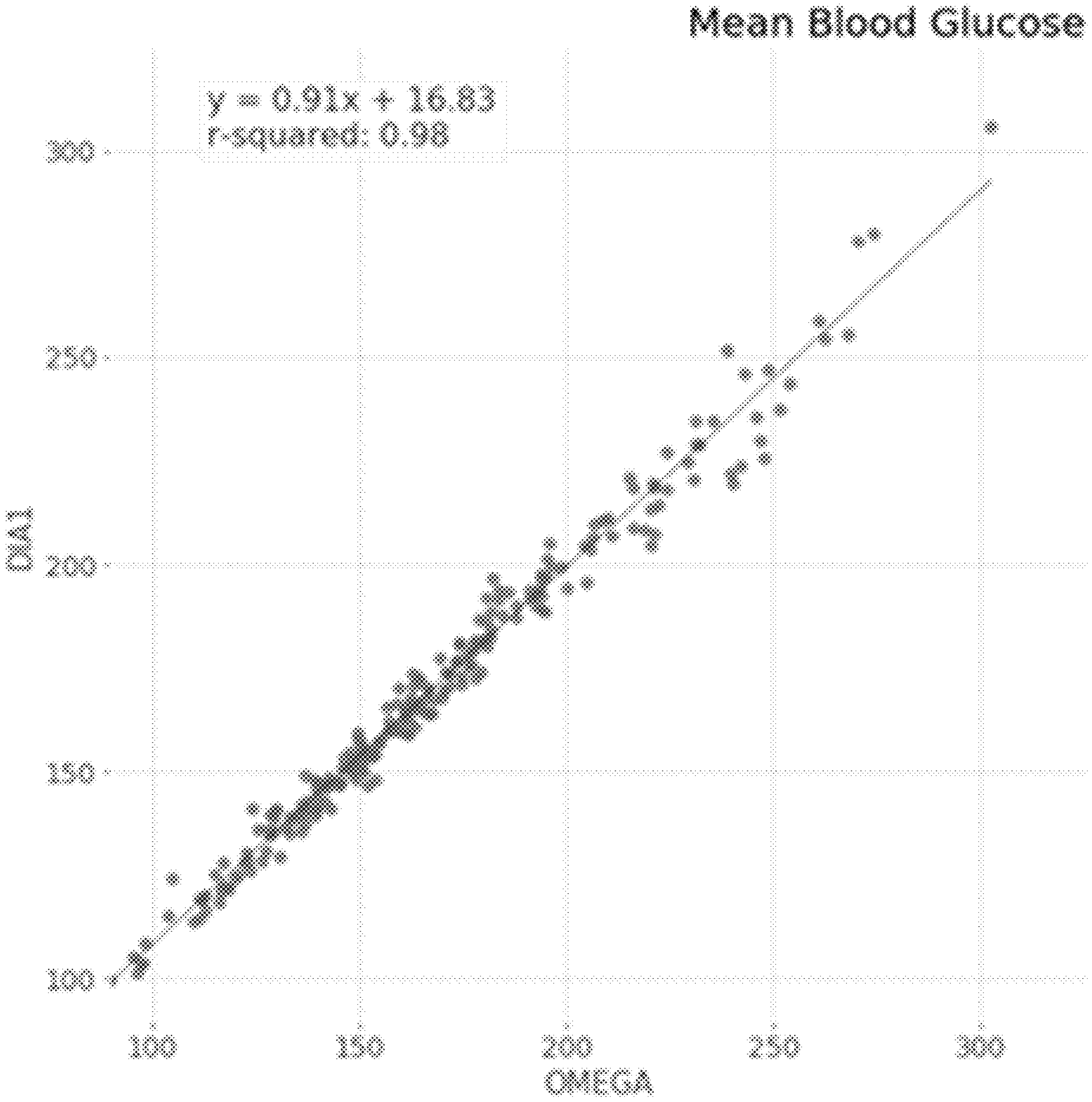
FIGS. 13A, 13B, 13C, 13D, 13E, and 13F show correlation scatter plots for Representative Daily Profiles in $\Omega$ versus the daily CGM profiles in DIA1, for six clinically relevant metrics.
Figure 13B:
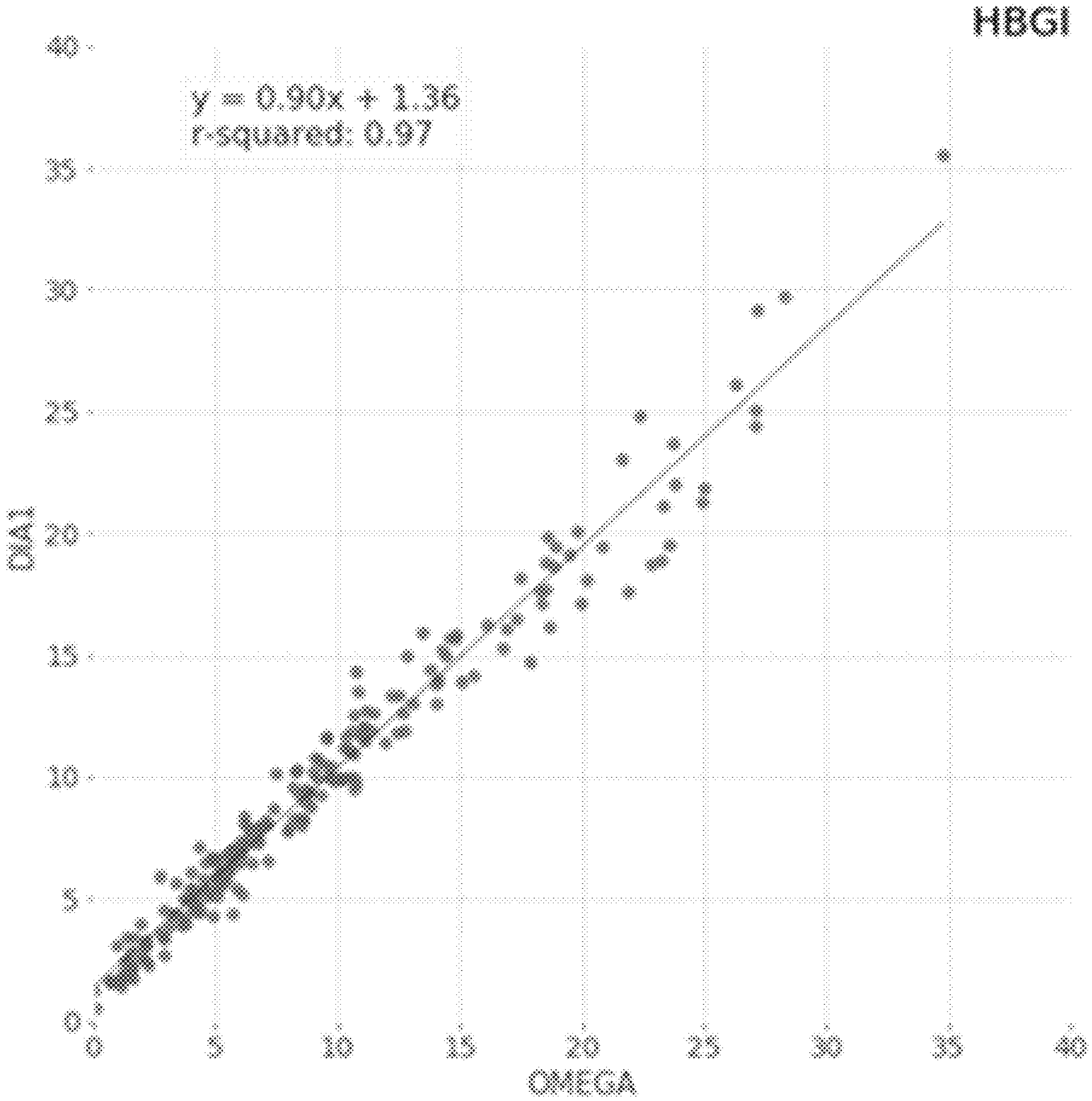
Figure 13C:
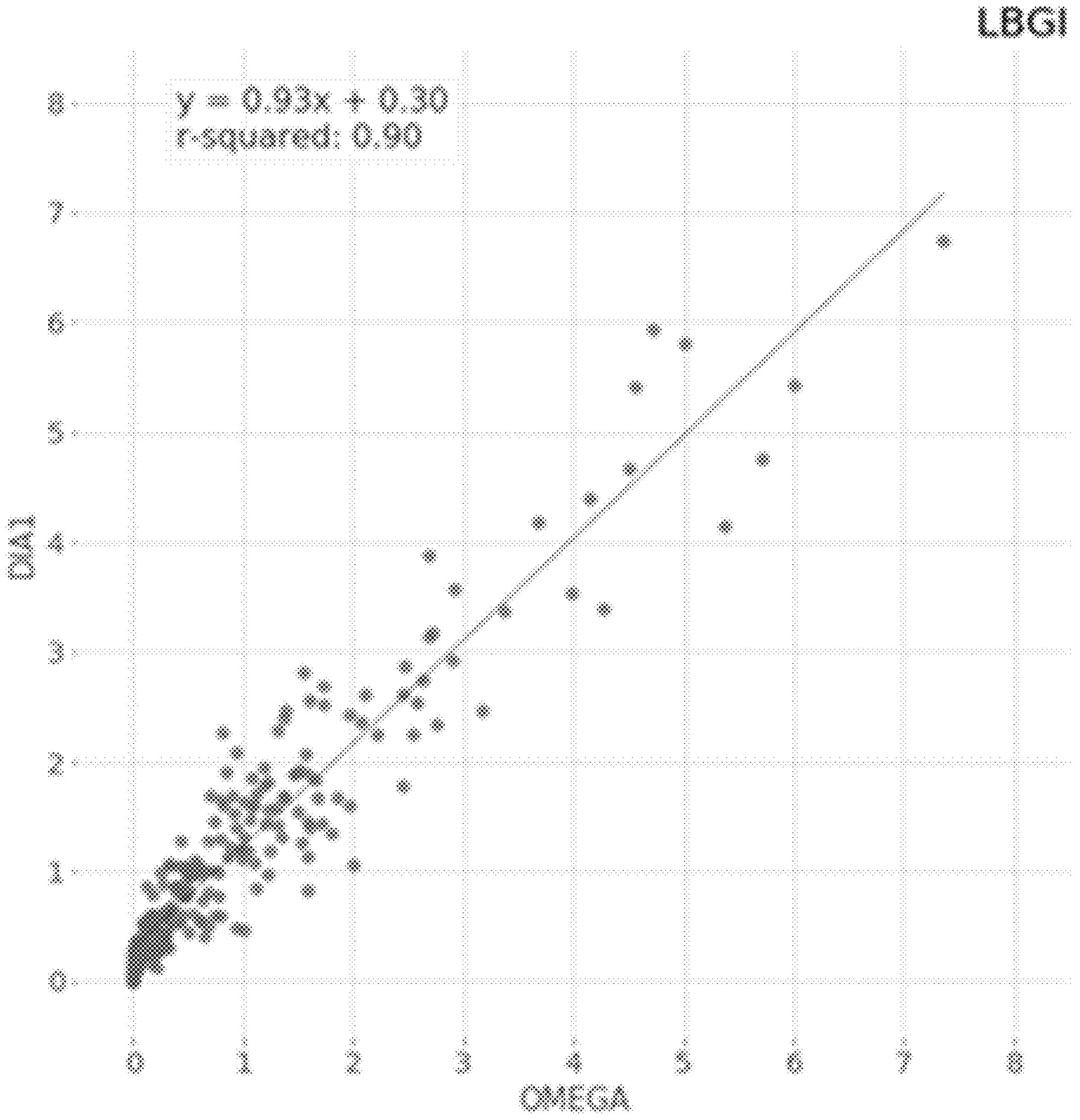
Figure 13D:
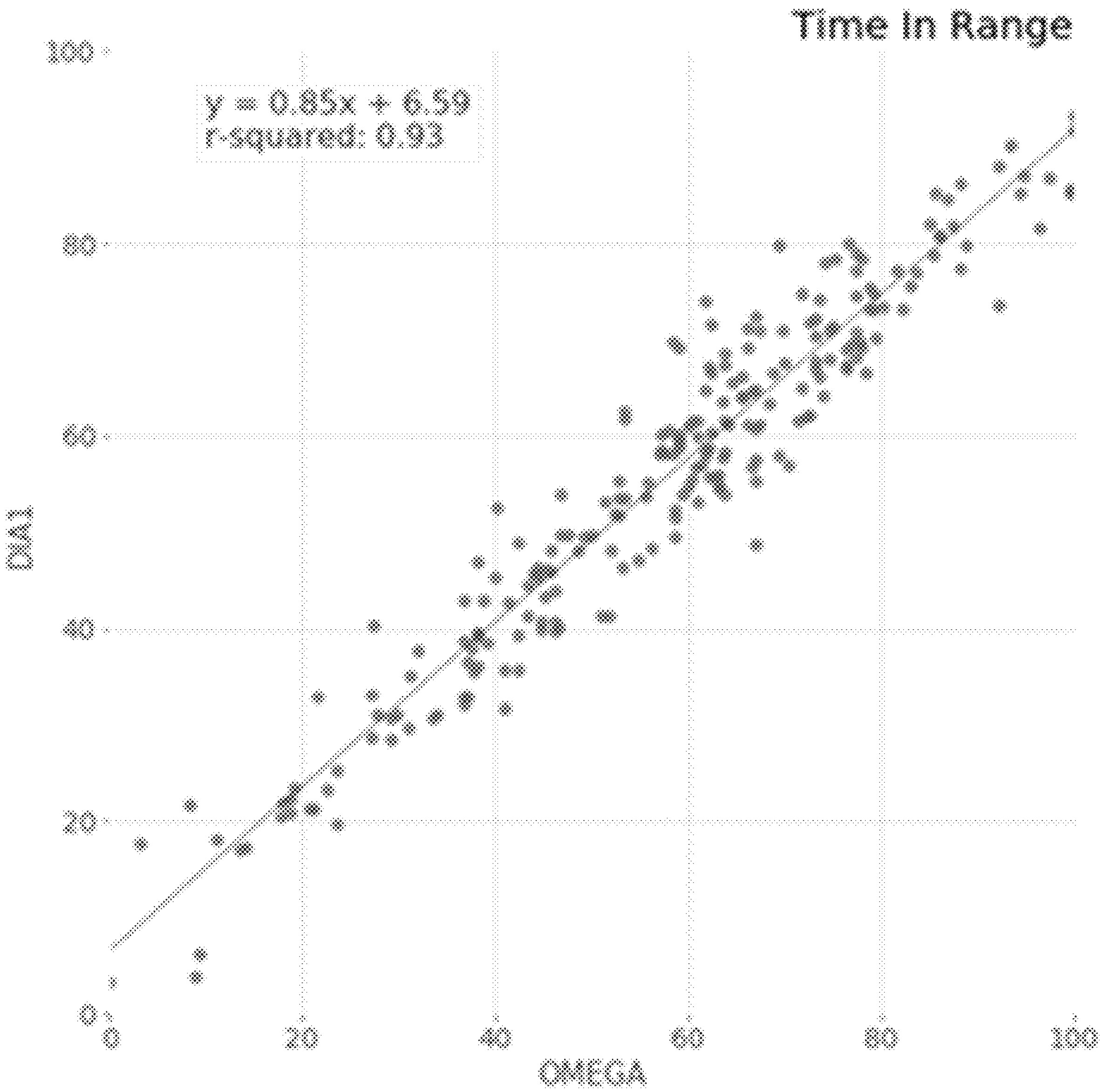
Figure 13E:
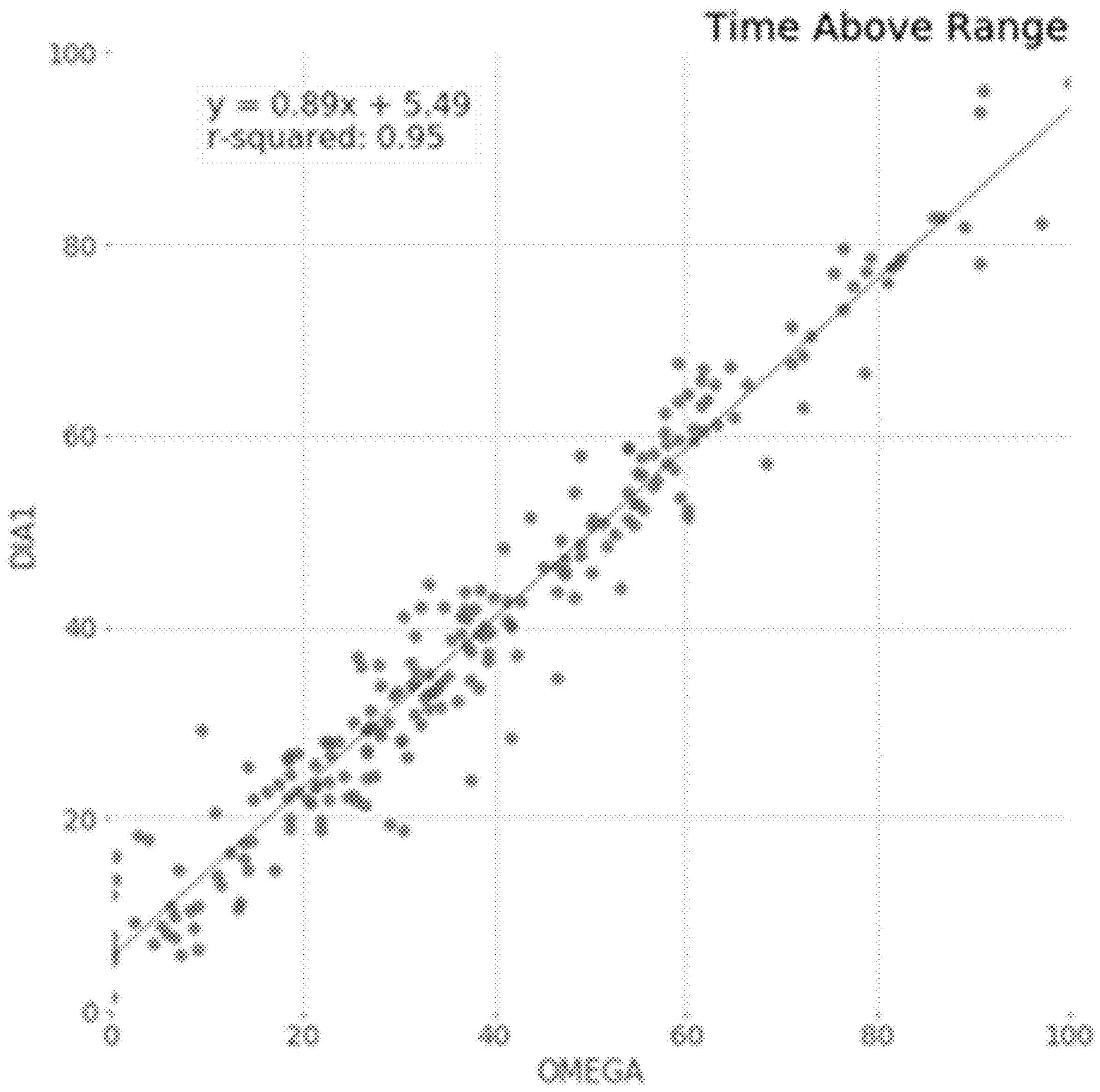
Figure 13F:
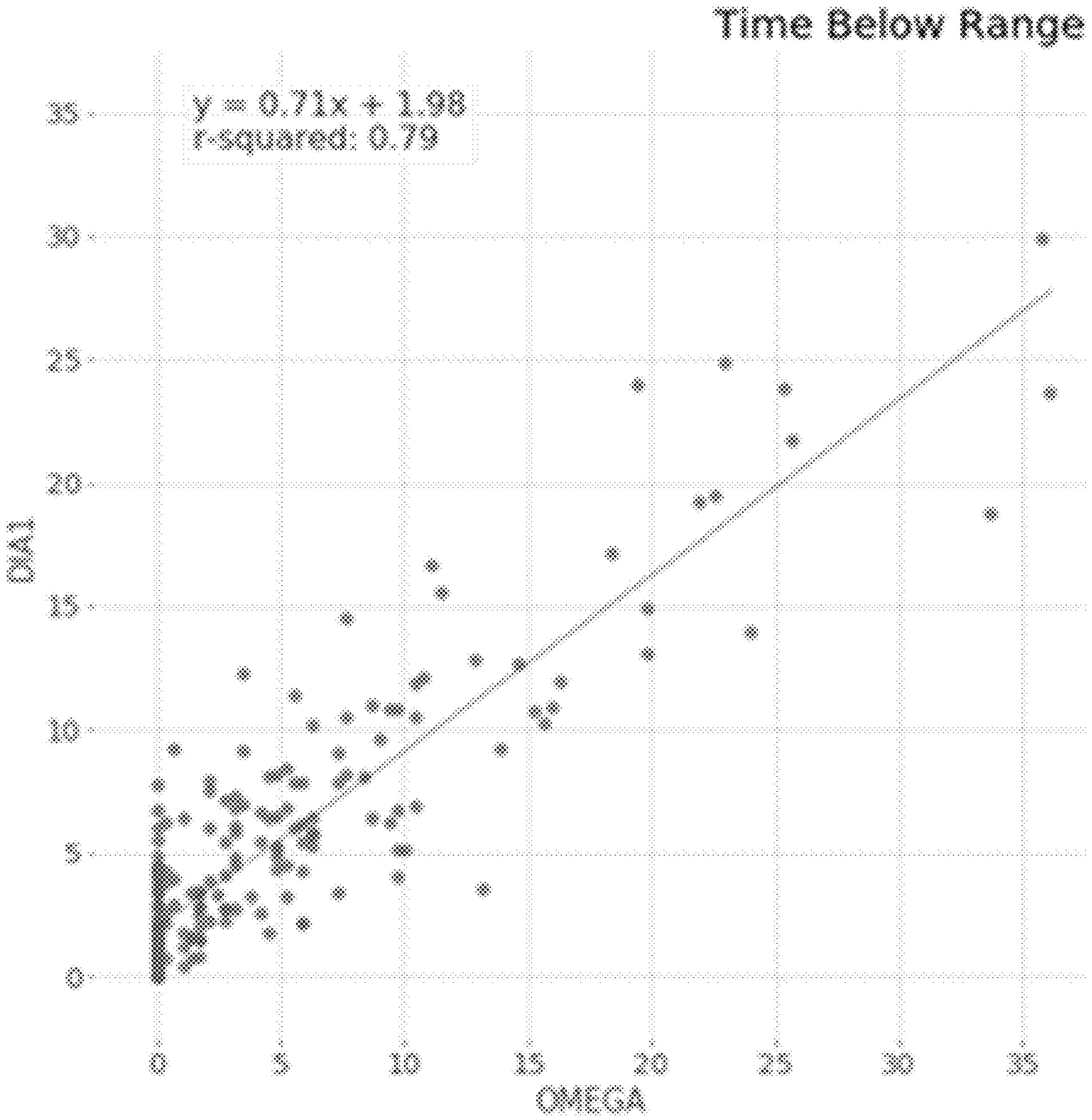
Figure 14A:
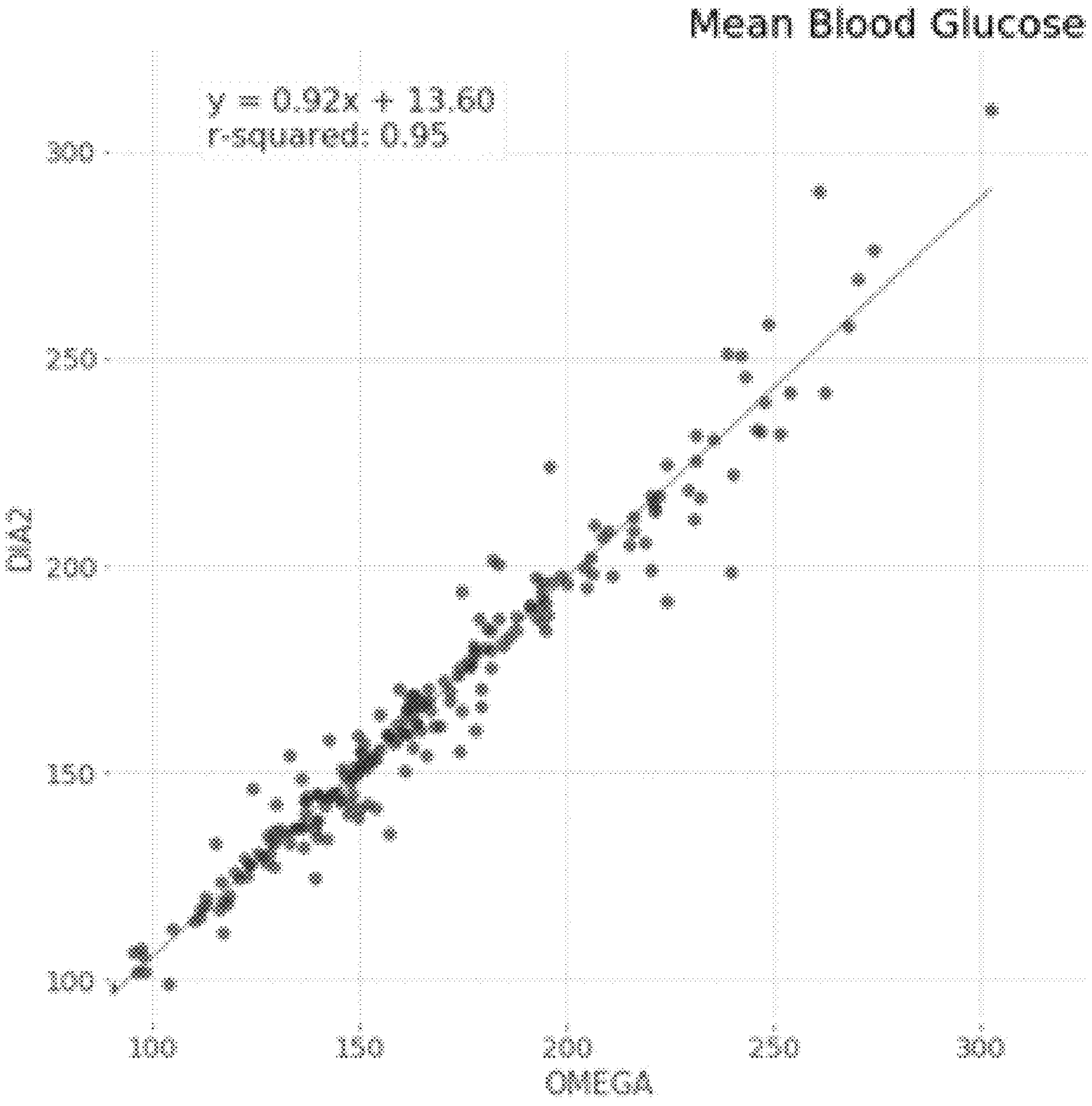
FIGS. 14A, 14B, 14C, 14D, 14E, and 14F show correlation scatter plots for Representative Daily Profiles in $\Omega$ versus the daily CGM profiles in DIA2, for six clinically relevant metrics.
Figure 14B:
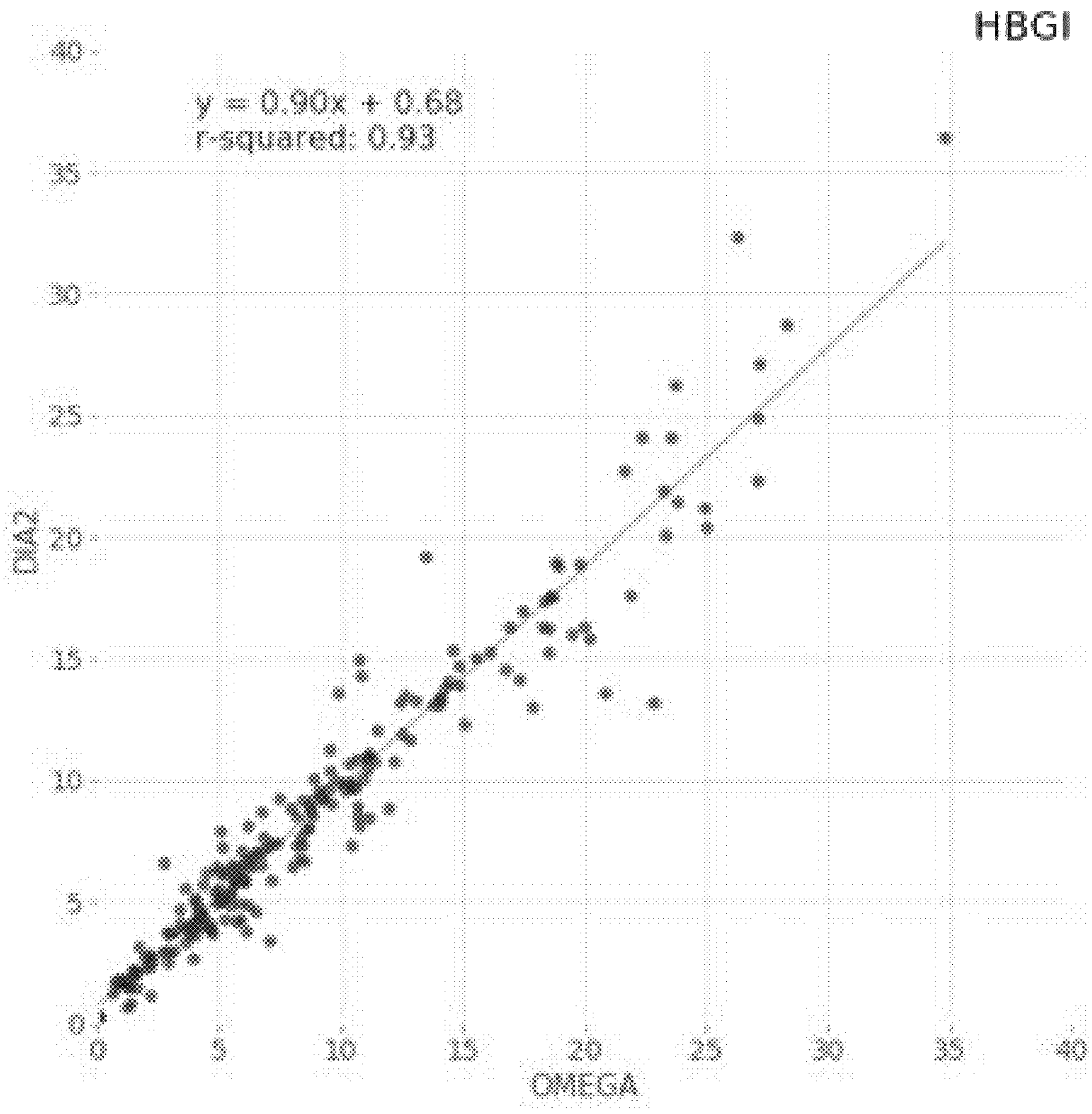
Figure 14C:
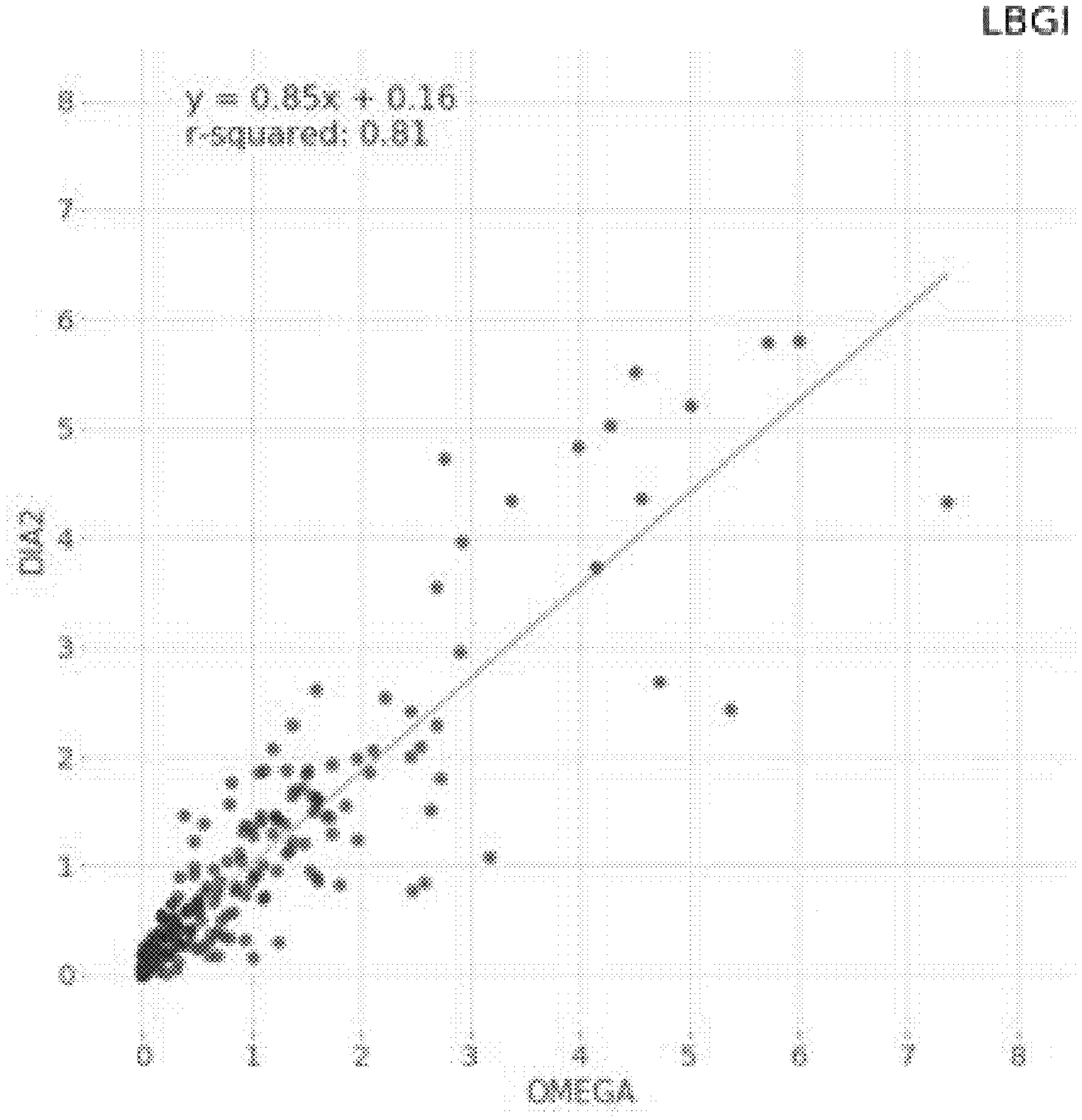
Figure 14D:
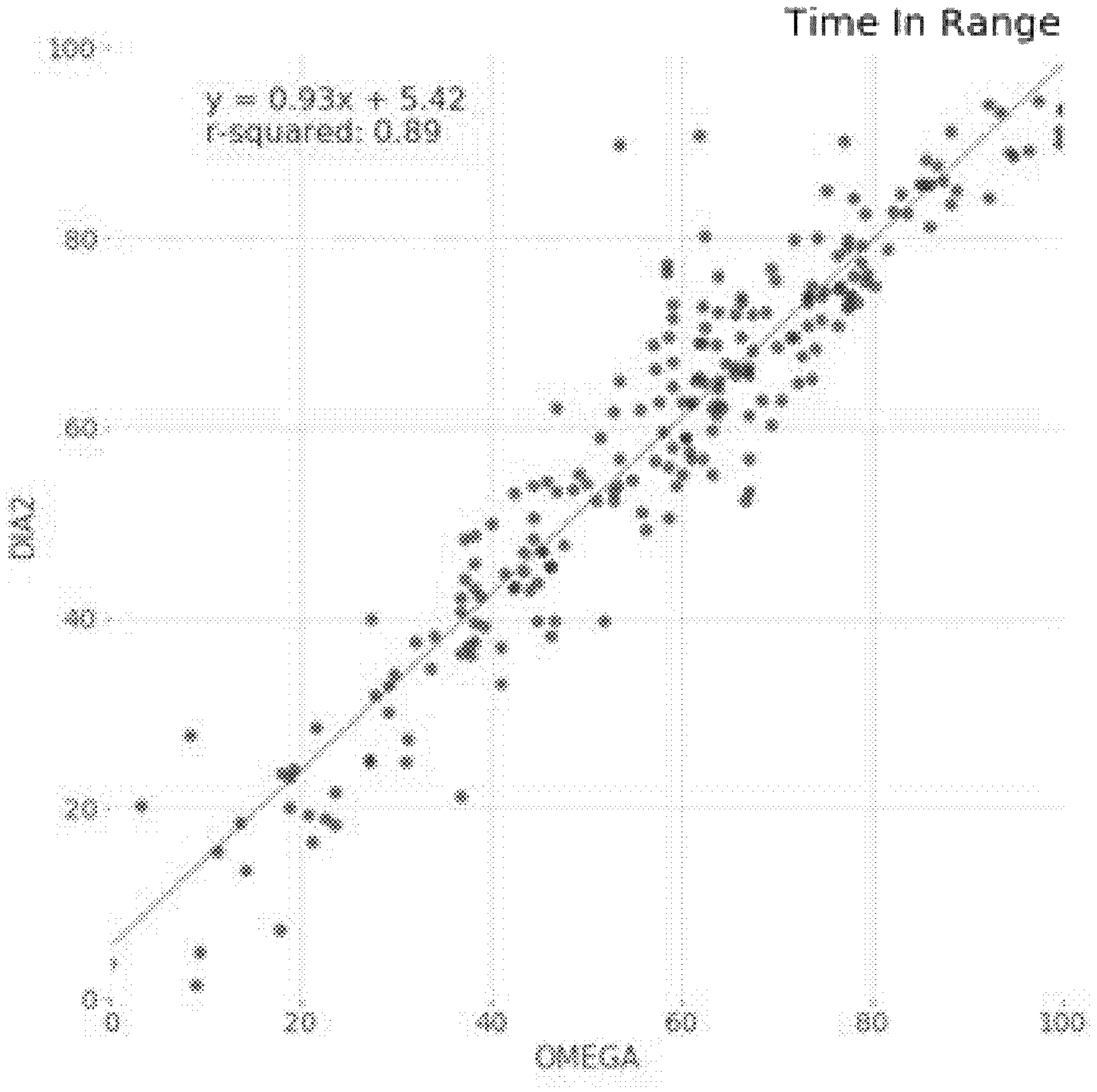
Figure 14E:
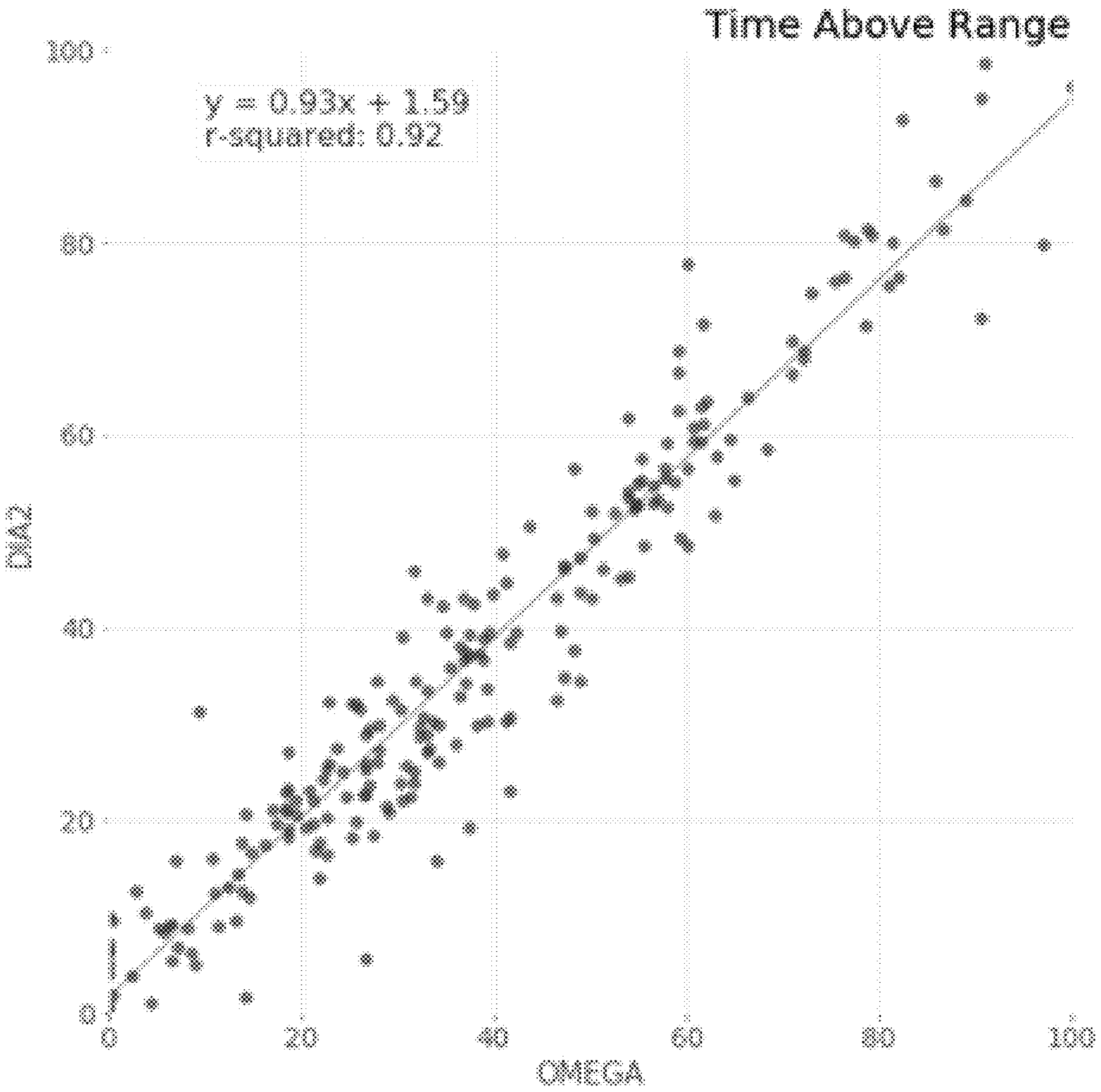
Figure 14F:
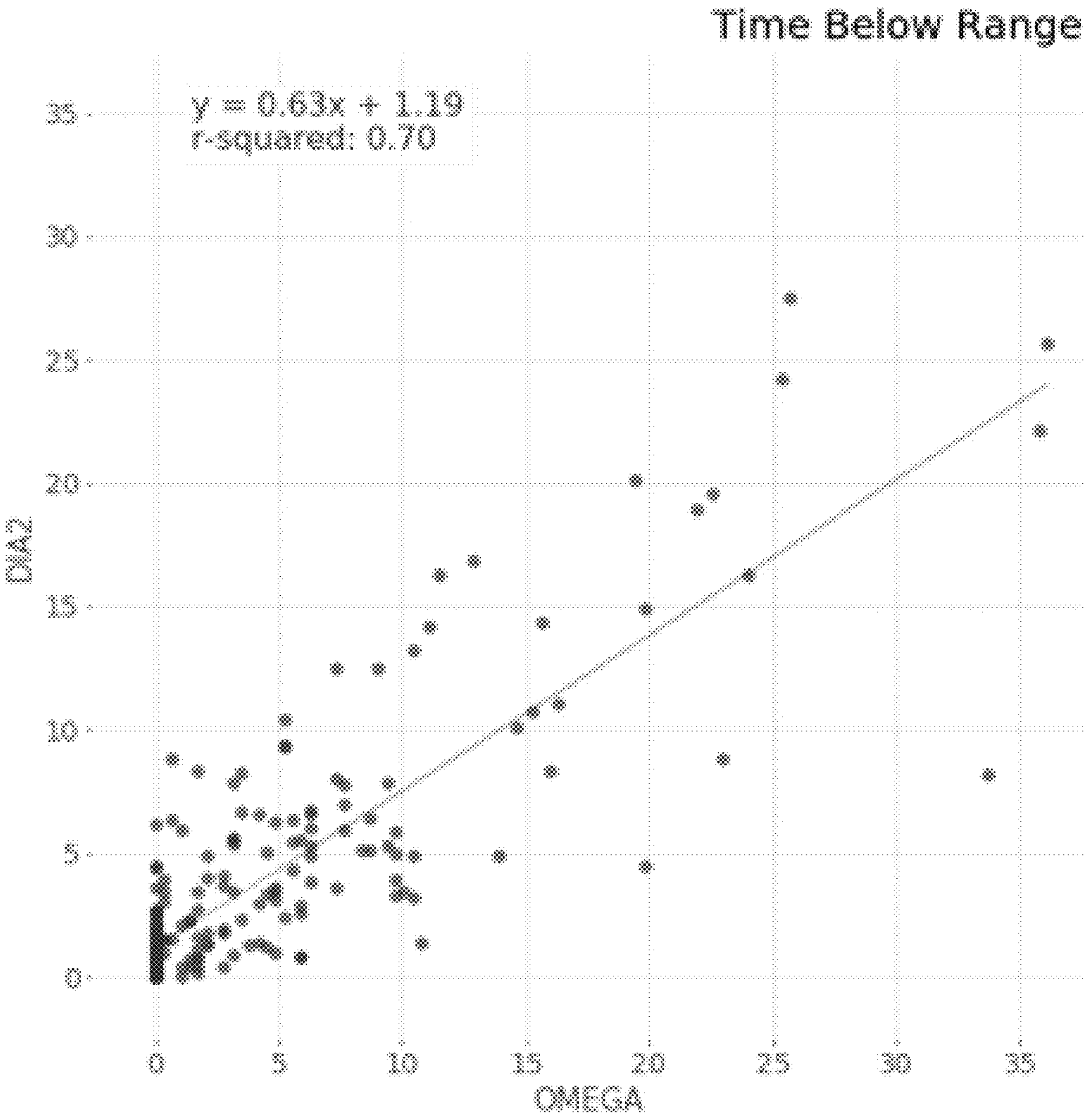

FIG. 10 is a block diagram illustrating an example of a machine upon which one or more aspects of embodiments of the present invention can be implemented.

An aspect of an embodiment of the present invention includes, but not limited thereto, a system, method, and computer readable medium that provides a means for building a model for classifying CGM data and a means for implementing the model to classify patent CGM data. FIG. 10 illustrates a block diagram of an example machine 1000' upon which one or more embodiments (e.g., discussed methodologies) can be implemented (e.g., run). The machine 1000' may be an exemplary system 100, for example.

Examples of machine 1000' can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium (e.g., non-transitory, non-volatile memory) or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time.

For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs)).

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a standalone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 1000') and software architectures that can be deployed in example embodiments.

In an example, the machine 1000' can operate as a standalone device or the machine 1000' can be connected (e.g., networked) to other machines.

In a networked deployment, the machine 1000' can operate in the capacity of either a server or a client machine in server-client network environments. In an example, machine 1000' can act as a peer machine in peer-to-peer (or other distributed) network environments. The machine 1000' can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 1000'. Further, while only a single machine 1000' is illustrated, the term "machine" shall also be taken to include any collection of machines that individually or jointly execute a set (or multiple sets) of instructions to perform any one or more of the methodologies discussed herein.

Example machine (e.g., computer system) 1000 can include a processor 1002 (e.g., a central processing unit (CPU), a graphics processing unit (GPU) or both), a main memory 1004 and a static memory 1006, some or all of which can communicate with each other via a bus 1008.

The machine 1000' can further include a display unit 1010, an alphanumeric input device 1012 (e.g., a keyboard), and a user interface (UI) navigation device 1014 (e.g., a mouse). In an example, the display unit 1010, input device 1017 and UI navigation device 1014 can be a touch screen display. The machine 1000' can additionally include a storage device (e.g., drive unit) 1016, a signal generation device 1018 (e.g., a speaker), a network interface device 1020, and one or more sensors 1021, such as a global positioning system (GPS) sensor, compass, accelerometer, or other sensor.

The storage device 1016 can include a machine readable medium 1022 on which is stored one or more sets of data structures or instructions 1024 (e.g., software) embodying or utilized by any one or more of the methodologies or functions described herein. The instructions 1024 can also reside, completely or at least partially, within the main memory 1004, within static memory 1006, or within the processor 1002 during execution thereof by the machine 1000'. In an example, one or any combination of the processor 1002, the main memory 1004, the static memory 1006, or the storage device 1016 can constitute machine readable media. While the machine readable medium 1022 is illustrated as a single medium, the term "machine readable medium" can include a single medium or multiple media (e.g., a centralized or distributed database, and/or associated caches and servers) that configured to store the one or more instructions 1024. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1024 can further be transmitted or received over a communications network 1126 using a transmission medium via the network interface device 1020 utilizing any one of a number of transfer protocols (e.g., frame relay, IP, TCP, UDP, HTTP, etc.).

Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

REFERENCES

The entire contents of each of the following references are incorporated herein by reference.

1. S. Aghabozorgi, A. Shirkhorshidi, and T. Wah. Time-series clustering—a decade review. *Information Systems,* 53:16-38, 2015.
2. P. Augstein, P. Heinke, L. Vogt, C. Rackow, K.-D. Kohnert, and E. Salzsieder. Q-score: development of a new metric for continuous glucose monitoring that enables stratification of antihyperglycaemic therapies. *BMC Endocrine Disorders,* 22 (15), 2015.
3. T. Battelino, Danne T, Bergenstal R M, Amiel S A, Beck R, Biester T, Bosi E, Buckingham B A, Cefalu W T, Close K L, Cobelli C, Dassau E, DeVries J H, Donaghue K C, Dovc K, Doyle F J, Garg S, Grunberger G, Heller S, Heinemann L, Hirsch I B, Hovorka R, Jia W, Kordonouri O, Kovatchev B, Kowalski A, Laffel L, Levine B, Mayorov A, Mathieu C, Murphy H R, Nimri R, Nørgaard K, Parkin C G, Renard E, Rodbard D, Saboo B, Schatz D, Stoner K, Urakami T, Weinzimer S A, and Phillip M. Clinical Targets for Continuous Glucose Monitoring Data Interpretation: Recommendations from the International Consensus on Time in Range. Diabetes Care 42:1593-1603, 2019.
4. R. Beck, T. Riddlesworth, K. Ruedy, A. Ahmann, R. Bergenstal, S. Haller, C. Kollman, D. Kruger, J. McGill, W. Polonsky, E. Toschi, H. Wolpert, and D. Price for the DIAMOND Study Group. Effect of Continuous Glucose Monitoring on Glycemic Control in Adults With Type 1 Diabetes Using Insulin Injections: The DIAMOND Randomized Clinical Trial. *JAMA,* 317 (4):371-378, 01 2017a.
5. R. Beck, T. Riddlesworth, K. Ruedy, A. Ahmann, S. Haller, D. Kruger, J. McGill, W. Polonsky, D. Price, S. Aronoff, R. Aronson, E. Toschi, C. Kollman, and R. Bergenstal for the DIAMOND Study Group. Continuous glucose monitoring versus usual care in patients with type 2 diabetes receiving multiple daily insulin injections. *Annals of Internal Medicine,* 167(6):365-374, 2017b.
6. Bergenstal. Understanding continuous glucose monitoring data. In *Role of Continuous Glucose Monitoring in diabetes treatment*, chapter 20, pages 20-23. American Diabetes Association, Arlington, VA, 2018.
7. Brown, B. Kovatchev, D. Raghinaru, J. Lum, B. Buckingham, Y. Kudva, L. Laffel, C. Levy, J. Pinsker, P. Wadwa, E. Dassau,
8. F. Doyle, S. Anderson, M. M. Church, V. Dadlani, L. Ekhlaspour, G. Forlenza, E. Isganaitis, D. Lam, C. Kollman, and R. Beck. Six-month randomized, multicenter trial of closed-loop control in type 1 diabetes. *New England Journal of Medicine,* 381(18):1707-1717, 2019.
9. T. Calin'ski and J. Harabasz. A dendrite method for cluster analysis. *Communications in Statistics,* 3(1):1-27, 1974.
10. D. L. Davies and D. W. Bouldin. A cluster separation measure. *IEEE Transactions on Pattern Analysis and Machine Intelligence*, PAMI-1(2):224-227, 1979.
11. N. Foster, R. Beck, K. Miller, M. Clements, M. Rickels, L. DiMeglio, D. Maahs, W. Tamborlane, R. Bergenstal, E. Smith, B. Olson, and S. Garg for the T1D Exchange Clinic Network. State of type 1 diabetes management and outcomes from the t1d exchange in 2016-2018. *Diabetes Technology & Therapeutics,* 21(2): 66-72, 2019.
12. H. Hall, D. Perelman, A. Breschi, P. Limcaoco, R. Kellogg, T. McLaughlin, and M. Snyder. Glucotypes reveal new patterns of glucose dysregulation. *PLoS Biology,* 16(7):e2005143, 2018.

13. J. Han, M. Kamber, and J. Pei. *Data mining: Concepts and techniques*. Morgan Kaufmann Publisher, Waltham, MA, 3 edition, 2011.
14. A. Kahkoska, L. Adair, A. Aiello, K. Burger, J. Buse, J. Crandell, D. Maahs, C. Nguyen, M. Kosorok, and E. Mayer-Davis. Identification of clinically relevant dysglycemia phenotypes based on continuous glucose monitoring data from youth with type 1 diabetes and elevated hemoglobin a1c. *Pediatric Diabetes,* 20(5):556-566, 2019.
15. K. Kamgar, S. Gharghabi, and E. Keogh. Matrix Profile XV: Exploiting time series consensus motifs to find structure in time series sets. In 2019 *IEEE International Conference on Data Mining* (*ICDM*), pages 1156-1161, 2019.
16. B. Kovatchev B P, Cox D J, Gonder-Frederick L A, W L Clarke. Symmetrization of the Blood Glucose Measurement Scale and Its Applications. Diabetes Care, 20: 1655-1658, 1997.
17. B. Kovatchev. Metrics for glycaemic control—from HbA1c to continuous glucose monitoring. *Nature Reviews Endocrinology,* 13:425-436, 2017.
18. B. Kovatchev. Diabetes technology: Monitoring, analytics, and optimal control. *Cold Spring Harbor Perspectives in Medicine,* 9: a034389, 2019.
19. B. Kovatchev, S. Anderson, D. Raghinaru, Y. Kudva, L. Laffel, C. Levy, J. Pinsker, R. Wadwa, B. Buckingham, F. Doyle, S. Brown, M. M. Church, V. Dadlani, E. Dassau, L. Ekhlaspour, G. Forlenza, E. Isganaitis, D. Lam, J. Lum, and R. Beck.
20. Randomized controlled trial of mobile closed-loop control. *Diabetes Care,* 43(3):607-615, 2020. T. Liao. Clustering of time series data—a survey. *Pattern Recognition,* 38:1857-1874, 2005.
21. W. McKinney. Data structures for statistical computing in python. In St'efan van der Walt and Jarrod Millman, editors, *Proceedings of the 9th Python in Science Conference*, pages 51-56, 2010.
22. R. Nimri, A. Ochs, J. Pinsker, M. Phillip, and E. Dassau. Decision support systems and closed loop. *Diabetes Technology & Therapeutics,* 21(S1):S-42-S-56, 2019.
23. P. Rousseeuw. Silhouettes: A graphical aid to the interpretation and validation of cluster analysis. *Journal of Computational and Applied Mathematics,* 20:53-65, 1987.
24. V. Shah, S. DuBose, Z. Li, R. Beck, A. Peters, R. Weinstock, D. Kruger, M. Tansey, D. Sparling, S. Woerner, F. Vendrame, R. Bergenstal, W. Tamborlane, S. Watson, and J. Sherr. Continuous Glucose Monitoring Profiles in Healthy Nondiabetic Participants: A Multicenter Prospective Study. *The Journal of Clinical Endocrinology & Metabolism,* 104(10):4356-4364, 2019.
25. P. Virtanen, R. Gommers, T. Oliphant, M. Haberland, T. Reddy, D. Cournapeau, E. Burovski, P. Peterson, W. Weckesser,
26. J. Bright, S. van der Walt, M. Brett, J. Wilson, K. Jarrod Millman, N. Mayorov, A. Nelson, E. Jones, R. Kern, E. Larson, C. Carey, I. Polat, Y. Feng, E. Moore, J. VanderPlas, D. Laxalde, J. Perktold, R. Cimrman, I. Henriksen, E. A. Quintero,
27. C. Harris, A. Archibald, A. Ribeiro, F. Pedregosa, P. van Mulbregt, and SciPy 1.0 Contributors. SciPy 1.0: Fundamental Algorithms for Scientific Computing in Python. *Nature Methods,* 17:261-272, 2020.
28. F. Wilcoxon. Individual comparisons by ranking methods. *Biometrics Bulletin,* 1(6):80-83, 1945.
29. A. Woldaregay, E. °Arsand, T. Botsis, D. Albers, L. Mamykina, and G. Hartvigsen. Data-driven blood glucose pattern classification and anomalies detection: Machine-learning applications in type 1 diabetes. *Journal of Medical Internet Research,* 21(5):e11030, 2019a.
30. A. Woldaregay, E. °Arsand, S. Walderhaug, D. Albers, L. Mamykina, and G. Botsis, T. Hartvigsen. Data-driven modeling and prediction of blood glucose dynamics: Machine learning applications in type 1 diabetes. *Artificial Intelligence in Medicine,* 98:109-134, 2019b.
31. World Health Organization. Diabetes fact sheet, 2020. URL https://www.who.int/news-room/fact-sheets/detail/diabetes. C. M. Yeh, Y. Zhu, L. Ulanova, N. Begum, Y. Ding, H. A. Dau, D. F. Silva, A. Mueen, and E. Keogh. Matrix Profile I: All pairs similarity joins for time series: A unifying view that includes motifs, discords and shapelets. In 2016 *IEEE 16th International Conference on Data Mining* (*ICDM*), pages 1317-1322, 2016.
32. World Health Organization. (2020) Diabetes fact sheet. [Online]. Available: https://www.who.int/news-room/fact-sheets/detail/diabetes.
33. B. Kovatchev, "Diabetes technology: Monitoring, analytics, and optimal control," *Cold Spring Harbor Perspectives in Medicine*, vol. 9, p. a034389, 2019.
34. R. Bergenstal, "Understanding continuous glucose monitoring data," in *Role of Continuous Glucose Monitoring in diabetes treatment*. Arlington, VA: American Diabetes Association, 2018, ch. 20, pp. 20-23.
35. R. Nimri, A. Ochs, J. Pinsker, M. Phillip, and E. Dassau, "Decision support systems and closed loop," *Diabetes Technology & Therapeutics*, vol. 21, no. S1, pp. S-42-S-56, 2019.
36. A. Woldaregay, E. Årsand, S. Walderhaug, D. Albers, L. Mamykina, and G. Botsis, T. Hartvigsen, "Data-driven modeling and prediction of blood glucose dynamics: Machine learning applications in type 1 diabetes," *Artificial Intelligence in Medicine*, vol. 98, pp. 109-134, 2019.
37. Kahkoska, L. Adair, A. Aiello, K. Burger, J. Buse, J. Crandell, D. Maahs, C. Nguyen, M. Kosorok, and E. Mayer-Davis, "Identification of clinically relevant dysglycemia phenotypes based on continuous glucose monitoring data from youth with type 1 diabetes and elevated hemoglobin a1c," *Pediatric Diabetes, vol.* 20, no. 5, pp. 556-566, 2019.
38. P. Augstein, P. Heinke, L. Vogt, C. Rackow, K.-D. Kohnert, and E. Salzsieder, "Q-score: development of a new metric for continuous glucose monitoring that enables stratification of antihyperglycaemic therapies," *BMC Endocrine Disorders*, vol. 22, no. 15, 2015.
39. A. Woldaregay, E. Årsand, T. Botsis, D. Albers, L. Mamykina, and G. Hartvigsen, "Data-driven blood glucose pattern classification and anomalies detection: Machine-learning applications in type 1 diabetes," *Journal of Medical Internet Research*, vol. 21, no. 5, p. e11030, 2019.
40. V. Shah, S. DuBose, Z. Li, R. Beck, A. Peters, R. Weinstock, D. Kruger, M. Tansey, D. Sparling, S. Woerner, F. Vendrame, R. Bergenstal, W. Tamborlane, S. Watson, and J. Sherr, "Continuous Glucose Monitoring Profiles in Healthy Nondiabetic Participants: Multicenter Prospective Study," *The Journal of Clinical Endocrinology & Metabolism*, vol. 104, no. 10, pp. 4356-4364, 2019.
41. N. Foster, R. Beck, K. Miller, M. Clements, M. Rickels, L. DiMeglio, D. Maahs, W. Tamborlane, R. Bergenstal, E. Smith, B. Olson, and S. Garg for the T1D Exchange Clinic Network, "State of type 1 diabetes management and outcomes from the t1d exchange in 2016-2018," *Diabetes Technology & Therapeutics*, vol. 21, no. 2, pp. 66-72, 2019.

42. B. Kovatchev, "Metrics for glycaemic control—from HbA1c to continuous glucose monitoring," *Nature Reviews Endocrinology*, vol. 13, pp. 425-436, 2017.
43. J. Han, M. Kamber, and J. Pei, *Data mining: Concepts and techniques,* 3rd ed. Waltham, MA: Morgan Kaufmann Publisher, 2011.
44. S. Aghabozorgi, A. Shirkhorshidi, and T. Wah, "Time-series clustering—a decade review," *Information Systems*, vol. 53, pp. 16-38, 2015.
45. T. Liao, "Clustering of time series data—a survey," *Pattern Recognition*, vol. 38, pp. 1857-1874, 2005.
46. H. Hall, D. Perelman, A. Breschi, P. Limcaoco, R. Kellogg, T. McLaughlin, and M. Snyder, "Glucotypes reveal new patterns of glucose dysregulation," *PLoS Biology*, vol. 16, no. 7, p. e2005143, 2018.
47. C. M. Yeh, Y. Zhu, L. Ulanova, N. Begum, Y. Ding, H. A. Dau, D. F. Silva, A. Mueen, and E. Keogh, "Matrix Profile I: All pairs similarity joins for time series: A unifying view that includes motifs, discords and shapelets," in 2016 *IEEE 16th International Conference on Data Mining (ICDM)*, 2016, pp. 1317-1322.
48. K. Kamgar, S. Gharghabi, and E. Keogh, "Matrix Profile XV: Exploiting time series consensus motifs to find structure in time series sets," in 2019 *IEEE International Conference on Data Mining (ICDM)*, 2019, pp. 1156-1161.
49. B. Kovatchev, D. Cox, L. Gonder-Frederick, and W. Clarke, "Symmetrization of the blood glucose measurement scale and its applications," *Diabetes Care*, vol. 20, no. 11, pp. 1655-1658, 1997.
50. B. Kovatchev, S. Anderson, D. Raghinaru, Y. Kudva, L. Laffel, C. Levy, J. Pinsker, R. Wadwa, B. Buckingham, F. Doyle, S. Brown, M. M. Church, V. Dadlani, E. Dassau, L. Ekhlaspour, G. Forlenza, E. Isganaitis, D. Lam, J. Lum, and R. Beck, "Randomized controlled trial of mobile closed-loop control," *Diabetes Care*, vol. 43, no. 3, pp. 607-615, 2020.
51. S. Brown, B. Kovatchev, D. Raghinaru, J. Lum, B. Buckingham, Y. Kudva, L. Laffel, C. Levy, J. Pinsker, P. Wadwa, E. Dassau, F. Doyle, S. Anderson, M. M. Church, V. Dadlani, L. Ekhlaspour, G. Forlenza, E. Isganaitis, D. Lam, C. Kollman, and R. Beck, "Six-month randomized, multicenter trial of closed-loop control in type 1 diabetes," *New England Journal of Medicine*, vol. 381, no. 18, pp. 1707-1717, 2019.
52. R. Beck, T. Riddlesworth, K. Ruedy, A. Ahmann, R. Bergenstal, S. Haller, C. Kollman, D. Kruger, J. McGill, W. Polonsky, E. Toschi, H. Wolpert, and D. Price for the DIAMOND Study Group, "Effect of Continuous Glucose Monitoring on Glycemic Control in Adults With Type 1 Diabetes Using Insulin Injections: The DIAMOND Randomized Clinical Trial," *Journal of the American Medical Association*, vol. 317, no. 4, pp. 371-378, 01 2017.
53. R. Beck, T. Riddlesworth, K. Ruedy, A. Ahmann, S. Haller, D. Kruger, J. McGill, W. Polonsky, D. Price, S. Aronoff, R. Aronson, E. Toschi, C. Kollman, and R. Bergenstal for the DIAMOND Study Group, "Continuous glucose monitoring versus usual care in patients with type 2 diabetes receiving multiple daily insulin injections," *Annals of Internal Medicine*, vol. 167, no. 6, pp. 365-374, 2017.
54. A. Bisio, S. Anderson, L. Norlander, G. O'Malley, J. Robic, S. Ogyaadu, L. Hsu, C. Levister, L. Ekhalaspour, D. Lam, C. Levy, B. Buckingham, and M. Breton, "Impact of a novel diabetes support system on a cohort of people with type 1 diabetes treated with multiple daily injections: a multi-center randomized study," 2021, working paper.
55. B. Kovatchev, L. Kollar, S. Anderson, C. Barnett, M. Breton, K. Carr, R. Gildersleeve, M. Oliveri, C. Wakeman, and S. Brown, "Evening and overnight closed-loop control versus 24/7 continuous closed-loop control for type 1 diabetes: a randomised crossover trial," *The Lancet Digital Health*, vol. 2, no. 2, pp. e64-e73, 2020
56. P. Virtanen, R. Gommers, T. Oliphant, M. Haberland, T. Reddy, D. Cournapeau, E. Burovski, P. Peterson, W. Weckesser, J. Bright, S. van der Walt, M. Brett, J. Wilson, K. Jarrod Millman, N. Mayorov, A. Nelson, E. Jones, R. Kern, E. Larson, C. Carey, İ. Polat, Y. Feng, E. Moore, J. VanderPlas, D. Laxalde, J. Perktold, R. Cimrman, I. Henriksen, E. A. Quintero, C. Harris, A. Archibald, A. Ribeiro, F. Pedregosa, P. van Mulbregt, and S . . . Contributors, "SciPy 1.0: Fundamental Algorithms for Scientific Computing in Python," *Nature Methods*, vol. 17, pp. 261-272, 2020.
57. W. McKinney, "Data structures for statistical computing in python," in Proceedings of the 9th Python in Science Conference, S. van der Walt and J. Millman, Eds., 2010, pp. 51-56.
58. F. Pedregosa, G. Varoquaux, A. Gramfort, V. Michel, B. Thirion, O. Grisel, M. Blondel, P. Prettenhofer, R. Weiss, V. Dubourg, J. Vanderplas, A. Passos, D. Cournapeau, M. Brucher, M. Perrot, and E. Duchesnay, "Scikit-learn: Machine learning in Python," *Journal of Machine Learning Research*, vol. 12, pp. 2825-2830, 2011.
59. L. van der Maaten and G. Hinton, "Visualizing data using t-sne," *Journal of Machine Learning Research*, vol. 9, pp. 2579-2605, 2008.
60. F. Wilcoxon, "Individual comparisons by ranking methods," *Biometrics Bulletin*, vol. 1, no. 6, pp. 80-83, 1945.
61. M. Breton and B. Kovatchev, "One Year Real-World Use of the Control-IQ Advanced Hybrid Closed-Loop Technology," *Diabetes Technology & Therapeutics*, vol. 23, no. 9, pp. 1-8, 2021.
62. *"Metrics for glycaemic control—from HbA1c to continuous glucose monitoring"*, Kovatchev, et al. Nature Reviews Endrocrinology, 2017.

It will be understood that modifications to the embodiments disclosed herein can be made to meet a particular set of design criteria. For instance, any of the components, features, or steps of the system o method can be any suitable number or type of each to meet a particular objective. Therefore, while certain exemplary embodiments of the systems and methods disclosed herein have been discussed and illustrated, it is to be distinctly understood that the invention is not limited thereto but can be otherwise variously embodied and practiced within the scope of the following claims.

It will be appreciated that some components, features, and/or configurations can be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiments. Thus, the components, features, and/or configurations of the various embodiments can be combined in any manner and such combinations are expressly contemplated and disclosed by this statement.

It will be appreciated by those skilled in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description and all changes that come within the meaning, range, and equivalence thereof are intended to be embraced therein. Additionally, the disclosure of a range of values is a disclosure of every numerical value within that range, including the end points.

What is claimed is:

1. A system for developing a model to classify continuous glucose monitoring (CGM) data, the system comprising:
- a processor;
- computer memory having instructions stored thereon that when executed will cause the processor to:
  - determine whether two CGM profiles match based on a similarity of shapes of the two CGM profiles, each CGM profile including a data set of CGM measurements;
  - designate two matching CGM profiles as a CGM profile pair;
  - transform the CGM profile pair into a motif, the motif being a representation of the CGM profile pair as a single data point;
  - label the motif as a labelled motif based on a clinical characteristic;
  - recursively repeat the determine, designate and transform steps of a CGM profile pairing process until a finite set of motifs is created, which includes the labelled motif as a classified data point;
  - monitor or analyze a concentration of glucose levels of a patient using the labelled motif, wherein monitoring or analyzing comprises comparing the glucose levels of the patient to the labelled motif; and
  - generate a signal that includes a command signal to an automated control system requiring, based on the comparing the glucose levels of the patient to the labelled motif: a determination of risk of hypo- or hyper-glycemia, change in a determination of a risk of hypo- or hyper-glycemia, a notification to check a glucose level, a modification of an insulin dosage, a modification of a basal insulin, a modification of a basal insulin rate, a modification of an insulin infusion rate, and/or a modification of patient nutritional administration.

2. The system of claim 1, wherein the instructions will cause the processor to:
- designate plural CGM profile pairs;
- transform the plural CGM profile pairs into one or more motifs;
- label the one or more motifs with one or more labels; and
- create the finite set of motifs which includes each individually labelled motif as a data point.

3. The system of claim 1, wherein:
- monitoring or analyzing a concentration of glucose levels in blood using the data point.

4. The system of claim 1, wherein the instructions will cause the processor to:
- obtain the two CGM profiles from a database of CGM profiles.

5. The system of claim 1, comprising:
- obtaining the CGM measurements from a CGM device.

6. The system of claim 1, wherein:
- at least one CGM profile is a daily CGM profile of CGM measurements pertaining to a 24 hours period.

7. The system of claim 1, wherein the instructions will cause the processor to:
- perform linear interpolation, cubic splines, backward propagation, and/or forward propagation when a CGM profile includes a number of CGM measurements that is less than a predetermined number.

8. The system of claim 1, wherein the instructions will cause the processor to:
- determine whether the two CGM profiles match by calculating a distance in risk space between two CGM profiles.

9. The system of claim 8, wherein the instructions will cause the processor to:
- calculate the distance in risk space between two CGM profiles by calculating a root mean squared (RMSE) between two CGM profiles.

10. The system of claim 1, wherein the clinical characteristic includes at least one or more of:
- a time in range measure in which a predetermined number of blood glucose values of a CGM profile is within a predetermined range;
- a time above range measure in which a predetermined number of blood glucose values of a CGM profile is greater than a predetermined value;
- a time below range measure in which a predetermined number of blood glucose values of a CGM profile is less than a predetermined value;
- a coefficient of variability measure of blood glucose values of a CGM profile; and/or
- a standard deviation measure of blood glucose values of a CGM profile.

11. The system of claim 1, wherein the processor is configured to be a component of, used in combination with, or in communication with:
- the automated control system.

12. A method for developing a model to classify continuous glucose monitoring (CGM) data, the method comprising:
- determining whether the two CGM profiles match based on a similarity of shapes of the two CGM profiles, each CGM profile including a data set of CGM measurements;
- designating two matching CGM profiles as a CGM profile pair;
- transforming the CGM profile pair into a motif, the motif being a representation of the CGM profile pair as a single data point;
- labeling the motif as a labelled motif based on a clinical characteristic; and
- recursively repeating the determining, designating and transforming steps of a CGM profile pairing process until a finite set of motifs is created, which includes the labelled motif as a classified data point;
- monitoring or analyzing a concentration of glucose levels of a patient using the labelled motif, wherein monitoring or analyzing comprises comparing the glucose levels of the patient to the labelled motif; and
- generating a signal that includes a command signal to an automated control system requiring, based on the comparing the glucose levels of the patient to the labelled motif: a determination of risk of hypo- or hyperglycemia, change in a determination of a risk of hypo- or hyper-glycemia, a notification to check a glucose level, a modification of an insulin dosage, a modification of a basal insulin, a modification of a basal insulin rate, a modification of an insulin infusion rate, and/or a modification of patient nutritional administration.

13. The method of claim 12, comprising:

designating plural CGM profile pairs;

transforming the plural CGM profile pairs to form one or more motifs;

labelling the one or more motifs with one or more labels; and creating the finite set of motifs which includes each individual labelled motif as a data point.

14. The method of claim 12, wherein:

monitoring or analyzing a concentration of glucose levels in blood using the data point.

15. The method of claim 12, wherein:

determining whether the two CGM profiles match involves calculating a distance in risk space between two CGM profiles.

16. The method of claim 12, wherein the clinical characteristic includes at least one or more of:

a time in range measure in which a predetermined number of blood glucose values of a CGM profile is within a predetermined range;

a time above range measure in which a predetermined number of blood glucose values of a CGM profile is greater than a predetermined value;

a time below range measure in which a predetermined number of blood glucose values of a CGM profile is less than a predetermined value;

a coefficient of variability measure of blood glucose values of a CGM profile; and/or a standard deviation measure of blood glucose values of a CGM profile.

17. A system for classifying patient continuous glucose monitoring (CGM) data, the system comprising:

a processor;

computer memory having instructions stored thereon that when executed will cause the processor to:

obtain a patient CGM profile including a data set of patient CGM measurements;

compare the patient CGM profile to a finite set of motifs, the finite set of motifs including CGM profile pairs that have been transformed into labelled motifs, each labelled motif being a representation of a corresponding CGM profile pair as a single data point;

classify the patient CGM profile into one or more clinical characteristics based on a match between the patient CGM profile and a CGM profile pair of a labelled motif;

monitor or analyze a concentration of glucose levels of a patient based on the classification of the patient CGM profile; and generate a signal that includes a command signal to an automated control system requiring, based on the classification of the patient CGM profile: a determination of risk of hypo- or hyper-glycemia, change in a determination of a risk of hypo- or hyper-glycemia, a notification to check a glucose level, a modification of an insulin dosage, a modification of a basal insulin, a modification of a basal insulin rate, a modification of an insulin infusion rate, and/or a modification of patient nutritional administration.

18. The system of claim 17, wherein the instructions will cause the processor to:

obtain the patient CGM profile from a CGM device; and obtain the finite set of motifs from a database.

19. The system of claim 17, wherein the instructions will cause the processor to:

identify a match between the patient CGM profile and a CGM profile pair of a labelled motif based on a similarity of shapes of the patient CGM profile and the CGM profile pair of the labelled motif.

20. The system of claim 17, wherein the processor is configured to be a component of, used in combination with, or in communication with:

the automated control system.

* * * * *